US012773460B2

(12) United States Patent
Schibli et al.

(10) Patent No.: US 12,773,460 B2
(45) Date of Patent: Oct. 27, 2026

(54) TRANSGLUTAMINASE CONJUGATION METHOD WITH A GLYCINE BASED LINKER

(71) Applicant: PAUL SCHERRER INSTITUT, Villigen PSI (CH)

(72) Inventors: Roger Schibli, Baden (CH); Martin Behe, Gelterkinden (CH); Philipp Spycher, Zürich (CH); Julia Frei, Brugg (CH); Jöri Wehrmüller, Zürich (CH)

(73) Assignee: PAUL SCHERRER INSTITUT, Villigen PSI (CH)

( * ) Notice: Subject to any disclaimer, the term of this patent is extended or adjusted under 35 U.S.C. 154(b) by 1323 days.

(21) Appl. No.: 17/435,356

(22) PCT Filed: Mar. 19, 2020

(86) PCT No.: PCT/EP2020/057697
§ 371 (c)(1),
(2) Date: Aug. 31, 2021

(87) PCT Pub. No.: WO2020/188061
PCT Pub. Date: Sep. 24, 2020

(65) Prior Publication Data

US 2022/0133904 A1 May 5, 2022

(30) Foreign Application Priority Data

Mar. 19, 2019 (EP) .................................... 19163810

(51) Int. Cl.
*A61K 47/68* (2017.01)
*A61K 47/65* (2017.01)
(Continued)

(52) U.S. Cl.
CPC .......... *A61K 47/6855* (2017.08); *A61K 47/65* (2017.08); *A61K 47/68033* (2023.08);
(Continued)

(58) Field of Classification Search
None
See application file for complete search history.

(56) References Cited

U.S. PATENT DOCUMENTS

| | | | |
|---|---|---|---|
| 4,137,230 | A | 1/1979 | Hashimoto et al. |
| 4,151,042 | A | 4/1979 | Higashide et al. |

(Continued)

FOREIGN PATENT DOCUMENTS

| | | | | |
|---|---|---|---|---|
| EP | 2287317 | A2 | 2/2011 | |
| EP | 2777714 | A1 * | 9/2014 | ............. A61K 47/65 |

(Continued)

OTHER PUBLICATIONS

Database Registry, Chemical Abstracts Service, Columbus, Ohio, US; Database Registry No. 57281-78-4, Glycyl-L-cysteine, entered Nov. 16, 1984 (Year: 1984).*

(Continued)

*Primary Examiner* — Karl J Puttlitz
(74) *Attorney, Agent, or Firm* — LATHROP GPM LLP; James H. Velema, Esq.

(57) ABSTRACT

The present invention relates to a method for generating an antibody-payload conjugate by means of a microbial transglutaminase (MTG). The method comprises a step of conjugating a linker comprising or having the peptide structure (shown in N->C direction) Gly-$(Aax)_m$-B-$(Aax)_n$ via the N-terminal primary amine of the N-terminal glycine (Gly) residue to a glutamine (Gln) residue comprised in the heavy or light chain of an antibody.

37 Claims, 23 Drawing Sheets

Specification includes a Sequence Listing.

(51) Int. Cl.

| | |
|---|---|
| ***A61K 49/00*** | (2006.01) |
| ***A61K 51/10*** | (2006.01) |
| ***A61P 35/00*** | (2006.01) |

(52) U.S. Cl.

CPC ...... *A61K 47/6889* (2017.08); *A61K 49/0058* (2013.01); *A61K 51/10* (2013.01); *A61P 35/00* (2018.01)

(56) References Cited

U.S. PATENT DOCUMENTS

| | | | |
|---|---|---|---|
| 4,248,870 | A | 2/1981 | Miyashita et al. |
| 4,260,608 | A | 4/1981 | Miyashita et al. |
| 4,265,814 | A | 5/1981 | Hashimoto et al. |
| 4,308,268 | A | 12/1981 | Miyashita et al. |
| 4,308,269 | A | 12/1981 | Miyashita et al. |
| 4,309,428 | A | 1/1982 | Miyashita et al. |
| 4,317,821 | A | 3/1982 | Miyashita et al. |
| 4,322,348 | A | 3/1982 | Asai et al. |
| 4,331,598 | A | 5/1982 | Hasegawa et al. |
| 5,416,064 | A | 5/1995 | Chari et al. |
| 6,660,510 | B2 | 12/2003 | Lin et al. |
| 7,989,434 | B2 | 8/2011 | Feng |
| 8,211,912 | B2 | 7/2012 | Roulston et al. |
| 9,427,478 | B2 | 8/2016 | Bregeon et al. |
| 9,676,721 | B2 | 6/2017 | Bair et al. |
| 9,717,803 | B2 | 8/2017 | Bregeon et al. |
| 9,764,038 | B2 | 9/2017 | Dennler et al. |
| 10,132,799 | B2 | 11/2018 | Belmant et al. |
| 10,434,180 | B2 | 10/2019 | Bregeon et al. |
| 10,639,291 | B2 | 5/2020 | Hu et al. |
| 10,675,359 | B2 | 6/2020 | Dennler et al. |
| 11,396,649 | B2 | 7/2022 | Spycher et al. |
| 12,076,412 | B2 | 9/2024 | Spycher et al. |
| 12,128,110 | B2 | 10/2024 | Spycher et al. |
| 2005/0256030 | A1 | 11/2005 | Feng |
| 2005/0260186 | A1 | 11/2005 | Bookbinder et al. |
| 2006/0104968 | A1 | 5/2006 | Bookbinder et al. |
| 2008/0063783 | A1 | 3/2008 | Kreij et al. |
| 2010/0143970 | A1 | 6/2010 | Yokoyama et al. |
| 2012/0270810 | A1 | 10/2012 | Preiss-Bloom et al. |
| 2014/0356385 | A1 | 12/2014 | Dennler et al. |
| 2017/0043033 | A1 | 2/2017 | Strop et al. |
| 2017/0151341 | A1 | 6/2017 | Ma et al. |
| 2018/0071402 | A1 | 3/2018 | Bregeon et al. |
| 2018/0078656 | A1 | 3/2018 | Steinkuhler et al. |
| 2018/0134766 | A1 | 5/2018 | Larson et al. |
| 2018/0193476 | A1 | 7/2018 | Dennler et al. |
| 2019/0194641 | A1 | 6/2019 | Spycher et al. |
| 2021/0128743 | A1 | 5/2021 | Spycher et al. |
| 2021/0163458 | A1 | 6/2021 | Bigot et al. |
| 2021/0228726 | A1 | 7/2021 | Bouchard et al. |
| 2021/0308277 | A1 | 10/2021 | Zhao et al. |
| 2022/0333093 | A1 | 10/2022 | Spycher et al. |
| 2023/0372525 | A1 | 11/2023 | Bertrand et al. |
| 2024/0036672 | A1 | 2/2024 | Shim et al. |
| 2024/0279634 | A1 | 8/2024 | Spycher et al. |
| 2024/0350656 | A1 | 10/2024 | Spycher et al. |
| 2024/0398972 | A1 | 12/2024 | Attinger-Toller et al. |
| 2025/0049943 | A1 | 2/2025 | Spycher et al. |
| 2025/0082774 | A1 | 3/2025 | Bertrand et al. |
| 2025/0161479 | A1 | 5/2025 | Spycher et al. |

FOREIGN PATENT DOCUMENTS

| | | | | |
|---|---|---|---|---|
| JP | 2006-524037 | A | 10/2006 | |
| JP | 2015-209426 | A | 11/2015 | |
| WO | WO 1994/012520 | A1 | 6/1994 | |
| WO | WO 1998/006692 | A1 | 2/1998 | |
| WO | WO 1999/005536 | A1 | 2/1999 | |
| WO | WO 2001/039806 | A1 | 6/2001 | |
| WO | WO 2002/083180 | A1 | 10/2002 | |
| WO | WO 2003/012068 | A2 | 2/2003 | |
| WO | WO 2003/087131 | A2 | 10/2003 | |
| WO | WO 2004/043493 | A1 | 5/2004 | |
| WO | WO 2008/102007 | A1 | 8/2008 | |
| WO | WO 2009/012268 | A1 | 1/2009 | |
| WO | WO 2009/099728 | A1 | 8/2009 | |
| WO | WO 2010/115629 | A2 | 10/2010 | |
| WO | WO 2010/115630 | A2 | 10/2010 | |
| WO | WO 2011/119484 | A1 | 9/2011 | |
| WO | WO 2012/041504 | A1 | 4/2012 | |
| WO | WO 2012/047724 | A1 | 4/2012 | |
| WO | WO 2012/059882 | A2 | 5/2012 | |
| WO | WO 2012/119787 | A1 | 9/2012 | |
| WO | WO 2013/040142 | A2 | 3/2013 | |
| WO | WO 2013/049830 | A2 | 4/2013 | |
| WO | WO 2013/092983 | A2 | 6/2013 | |
| WO | WO 2013/092998 | A1 | 6/2013 | |
| WO | WO 2014/135282 | A1 | 9/2014 | |
| WO | WO 2014/140300 | A1 | 9/2014 | |
| WO | WO 2014/202775 | A1 | 12/2014 | |
| WO | WO 2015/015448 | A2 | 2/2015 | |
| WO | WO 2015/054060 | A1 | 4/2015 | |
| WO | WO 2015/097267 | A1 | 7/2015 | |
| WO | WO 2015/162563 | A1 | 10/2015 | |
| WO | WO 2015/191883 | A1 | 12/2015 | |
| WO | WO 2016/030791 | A1 | 3/2016 | |
| WO | WO 2016/100735 | A1 | 6/2016 | |
| WO | WO-2016128410 | A1 * | 8/2016 | ....... A61K 47/48384 |
| WO | WO 2016/144608 | A1 | 9/2016 | |
| WO | WO 2016/207090 | A2 | 12/2016 | |
| WO | WO 2017/025179 | A1 | 2/2017 | |
| WO | WO 2017/025179 | A8 | 2/2017 | |
| WO | WO 2017/106643 | A1 | 6/2017 | |
| WO | WO 2018/154517 | A1 | 8/2018 | |
| WO | WO 2019/030223 | A1 | 2/2019 | |
| WO | WO 2019/057772 | A1 | 3/2019 | |
| WO | WO 2019/082020 | A1 | 5/2019 | |
| WO | WO 2019/096867 | A1 | 5/2019 | |
| WO | WO 2020/188061 | A1 | 9/2020 | |
| WO | WO 2022/058395 | A1 | 3/2022 | |
| WO | WO 2022/084560 | A1 | 4/2022 | |
| WO | WO 2023/137026 | A1 | 7/2023 | |
| WO | WO 2023/161291 | A1 | 8/2023 | |
| WO | WO 2023/192961 | A2 | 10/2023 | |

OTHER PUBLICATIONS

A New Site Specific Antibody Conjugation Using Bacterial Transglutaminase, Innate Pharma, 2013, downloaded from https://www.innate-pharma.com/sites/default/files/iph_adc_summit_2013_0.pdf, Sep. 10, 2025 (Year: 2013).*

International Search Report and Written Opinion for PCT International Patent Application No. PCT/EP2020/057697, mailed Jun. 16, 2020.

Tanaka et al., "N-terminal glycine-specific protein conjugation catalyzed by microbial transglutaminase", FEBS Letters, 579(10): 2092-2096.

U.S. Appl. No. 16/319,502 2019/0194641 U.S. Pat. No. 11,396,649, filed Jan. 22, 2019 Jun. 27, 2019 Jul. 26, 2022, Philipp Rene Spycher, Site-Specific Conjugation To Antibody Lysine Residues With Solid-Phase Immobilized Microbial Transglutaminase MTG And MTG In Solution.

U.S. Appl. No. 17/704,960 2022/0333093, filed Mar. 25, 2022 Oct. 20, 2022, Philipp Rene Spycher, Site-Specific Conjugation To Antibody Lysine Residues With Solid-Phase Immobilized Microbial Transglutaminase MTG And MTG In Solution.

U.S. Appl. No. 16/648,636 2021/0128743, filed Mar. 18, 2020 May 6, 2021, Philipp Spycher, Transglutaminase Conjugation Method And Linker.

U.S. Appl. No. 17/435,356 2022/0133904, filed Mar. 19, 2020 May 5, 2022, Roger Schibli, Transglutaminase Conjugation Method With A Glycine Based Linker.

De Young et al., "Transglutaminase Activity in Human and Rabbit Ear Comedogenesis: A Histochemical Study", Journal of Investigative Dermatology, 1984, 82(3): 275-279.

Dennler, "Microbial Transglutaminase as a Versatile Tool for Site-Specific Protein Modification", Doctoral Thesis, 2015, ETH Zürich, Dissertation No. 22512.

(56) References Cited

OTHER PUBLICATIONS

Dorywalska et al., "Molecular Basis of Valine-Citrulline-PABC Linker Instability in Site-Specific ADCs and Its Mitigation by Linker Design", Mol Cancer Ther., May 2016, 15(5): 958-970.
Fornera et al., "Immobilization of Peroxidase on SiO2 Surfaces with the Help of a Dendronized Polymer and the Avidin-Biotin System", Macromolecular Bioscience, Aug. 2011, 11(8): 1052-1067.
GB Search Report for GB Patent Application No. 1800878.9, dated Oct. 9, 2018.
International Search Report and Written Opinion for PCT International Patent Application No. PCT/EP2018/075350, mailed Jan. 28, 2019.
International Search Report and Written Opinion for PCT International Patent Application No. PCT/EP2014/067403, dated Oct. 25, 2017.
Jeger et al., "Site-specific and stoichiometric modification of antibodies by bacterial transglutaminase", Agnew Chem Int Ed Engl., Dec. 17, 2010, 49(51): 9995-9997.
Kato et al. "Peptide-binding assessment using mass spectrometry as a new screening method for skin sensitization", J Toxicol Sci., Feb. 2003, 28(1): 19-24.
Khew et al., "Characterization of amine donor and acceptor sites for tissue type transglutaminase using a sequence from the C-terminus of human fibrillin-1 and the N-terminus of osteonectin", Biomaterials, Jun. 2010, 31(16): 4600-4608.
Lhospice et al., "Site-Specific Conjugation of Monomethyl Auristatin E to Anti-CD30 Antibodies Improves Their Pharmacokinetics and Therapeutic Index in Rodent Models", Mol Pharm., Jun. 2015, 12(6): 1863-1871.
Maude et al., "Peptide Synthesis and Self-Assembly", Peptide-Based Materials, Topics in Current Chemistry 310, Jan. 10, 2012, p. 62.
Mindt et al., "Modification of Different IgG1 Antibodies via Glutamine and Lysine using Bacterial and Human Tissue Transglutaminase", Bioconjugate Chem., 2008, 19(1): 271-278.
New Zealand Search and Examination Report for New Zealand Patent Application No. 762376, dated Feb. 1, 2022.
Oh et al., "Characteristics of an immobilized form of transglutaminase: A possible increase in substrate specificity by selective interaction with a protein spacer", Journ Agric Food Chem., 1993, 41(8): 1337-1342.
Roig et al., "Biotechnology and applied biology section applications of immobilized enzymes", Biochemical Education, Oct. 1987, 15(4): 198-208.
Spycher et al., "Dual, Site-Specific Modification of Antibodies by Using Solid-Phase Immobilized Microbial Transglutaminase", Chembiochem., Oct. 5, 2017, 18(19): 1923-1927.
Strop et al., "Location Matters: Site of Conjugation Modulates Stability and Pharmacokinetics of Antibody Drug Conjugates", Chemistry & Biology, Feb. 21, 2013, 20: pp. 161-167.
Yuan et al. "Tissue transglutaminase 2 inhibition promotes cell death and chemosensitivity in glioblastomas", Mol. Cancer Ther., Sep. 2005, 4(9): 1293-1302.
Zhang et al., "A Rigid, Chiral, Dendronized Polymer with a Thermally Stable, Right-Handed Helical Conformation", Chemistry A European Journal, Aug. 8, 2008, 14(23): 6924-6934.
Zhou et al., "The microbial transglutaminase immobilization on carboxylated poly(N-isopropylacrylamide) for thermo-responsivity", Enzyme and Microbial Technology, 2016, vol. 87-88, pp. 44-51.
Agard et al., "A Comparative Study of Bioorthogonal Reactions with Azides", ACS Chem. Biol., 2006, 1: 644-648.
Amant et al., "A Reactive Antibody Platform for One-Step Production of Antibody-Drug Conjugates through a Diels-Alder Reaction with Maleimide", Bioconjugate Chem, 2019, 30(9): 2340-2348.
Amant et al., "Tuning the Diels-Alder Reaction for Bioconjugation to Maleimide Drug-Linkers", Bioconjugate Chem., 2018, 29(7): 2406 2414.
Amsberry et al., "The lactonization of 2'-hydroxyhydrocinnamic acid amides: a potential prodrug for amines", J. Org. Chem., 1990, 55: 5867.
Azhdarinia et al., "Dual-Labeling Strategies for Nuclear and Fluorescence Molecular Imaging: A Review and Analysis", Mol Imaging Biol., 2011, 14(3): 261-276.
Balhorn et al., "Hexa-arginine enhanced uptake and residualization of selective high affinity ligands by Raji lymphoma cells", Molecular Cancer, 2009, 8(25): 1-9.
Bargh et al., "Cleavable linkers in antibody-drug conjugates", Chem Soc Rev., Aug. 12, 2019, 48(16): 4361-4374.
Baskin et al., "Copper-free click chemistry for dynamic in vivo imaging", PNAS, 2007, 104(43): 16793-16797.
Benjamin et al., "Thiolation of Q295: Site-Specific Conjugation of Hydrophobic Payloads without the Need for Genetic Engineering", Mol. Pharmaceutics, 2019, 16: 2795-2807.
Blackman et al., "The Tetrazine Ligation: Fast Bioconjugation based on Inverse-electron-demand Diels-Alder Reactivity", Journal of the American Chemical Society, 2008, 130(41): 13518-13519.
Bodero et al., "Synthesis and biological evaluation of RGD and isoDGR peptidomimetic-a-amanitin conjugates for tumor-targeting", Beilstein J. Org. Chem., 2018, 14: 407 415.
Costoplus et al., "Peptide-Cleavable Self-immolative Maytansinoid Antibody-Drug Conjugates Designed To Provide Improved Bystander Killing", ACS Med. Chem. Lett., 2019, 10(10): 1393-1399.
Dal Corso et al., "Innovative Linker Strategies for Tumor-Targeted Drug Conjugates", Chemistry, 2019, 25(65): 14740-14757.
Dickgiesser et al., "Site-Specific Conjugation of Native Antibodies Using Engineered Microbial Transglutaminases", Bioconjug Chem., Mar. 12, 2020, 31(4): 1070-1076.
Dokter et al., "Preclinical profile of the HER2-targeting ADC SYD983/SYD985: introduction of a new duocarmycin-based linker-drug platform", Mol Cancer Ther., Nov. 2014, 13(11): 2618-2629.
Doronina et al., "Enhanced activity of monomethylauristatin F through monoclonal antibody delivery: effects of linker technology on efficacy and toxicity", Bioconjug Chem., Jan. 2006, 17(1): 114-124.
Dorywalska et al., "Site-Dependent Degradation of a Non-Cleavable Auristatin-Based Linker-Payload in Rodent Plasma and Its Effect on ADC Efficacy", PLoS ONE, 2015, 10(7): e0132282.
Dubowchik et al., "Cathepsin B-labile dipeptide linkers for lysosomal release of doxorubicin from internalizing immunoconjugates: model studies of enzymatic drug release and antigen-specific in vitro anticancer activity", Bioconjug Chem, 2002, 13(4): 855-869.
Great Britain Search Report for Great Britain Patent Application No. GB1800878.9, mailed Oct. 9, 2018.
Hay et al., "A 2-nitroimidazole carbamate prodrug of 5-amino-1-(chloromethyl)-3-[(5,6,7-trimethoxyindol-2-yl)carbonyl]-1,2-dihydro-3H-benz[e]indole (amino-seco-CBI-TMI) for use with ADEPT and GDEPT", Bioorg. Med. Chem. Lett., 1999, 9(15): 2237-2242.
Higashide et al., "Ansamitocin, a group of novel maytansinoid antibiotics with antitumour properties from Nocardia", Nature, 1977, 270: 721-722.
Houghton et al., "Site-specifically labeled CA19.9-targeted immunoconjugates for the PET, NIRF, and multimodal PET/NIRF imaging of pancreatic cancer", PNAS USA, Dec. 29, 2015, 112(52): 15850-15855.
Huang et al., "Characterization of antibody-drug conjugates by mass spectrometry: advances and future trends", Drug Discover Today, 2016, 21(5): 850-855.
Huggins et al., "Site Selective Antibody-Oligonucleotide Conjugation via Microbial Transglutaminase", Molecules, Sep. 10, 2019, 24(18): 3287.
International Search Report and Written Opinion for PCT International Patent Application No. PCT/EP2021/075831, dated Dec. 14, 2021.
International Search Report and Written Opinion for PCT International Patent Application No. PCT/EP2021/079560, dated Feb. 8, 2022.
International Search Report and Written Opinion for PCT International Patent Application No. PCT/EP2022/079787, dated Feb. 13, 2023.

(56) References Cited

OTHER PUBLICATIONS

Kawai et al., "Chemical Modification of Ansamitocins. III. Synthesis and Biological Effects of 3-Acyl Esters of Maytansinol", Chem. Pharm Bull., 1984, vol. 32(9): 3441-3451.
Kehrer et al., "Modulation of camptothecin analogs in the treatment of cancer: a review", Anticancer Drugs, 2001, 12(2): 89-105.
Kieliszek, "Microbial transglutaminase and its application in the food industry. A review", Folia Microbiol (Praha), 2014, 59(3): 241-250.
Kingsbury et al., "A novel peptide delivery system involving peptidase activated prodrugs as antimicrobial agents. Synthesis and biological activity of peptidyl derivatives of 5-fluorouracil", J. Med. Chem., 1984, 27(11): 1447-1451.
Kolb et al., "The growing impact of click chemistry on drug discovery", Drug Discov Today, Dec. 15, 2003, 8(24): 1128-1137.
Kontermann et al., "Bispecific antibodies", Drug Discov Today, 2015, 20(7): 838-847.
Kupchan et al., "Tumor inhibitors. 124. Structural requirements for antileukemic activity among the naturally occurring and semisynthetic maytansinoids", J. Med. Chem., 1978, 21(1): 31-37.
Lambert et al., "Antibody—Drug Conjugates for Cancer Treatment", Annu. Rev. Med., 2018, 69: 191 207.
Levengood et al., "Orthogonal Cysteine Protection Enables Homogeneous Multi-Drug Antibody-Drug Conjugates", Angewandte Chem Int Ed Engl., Jan. 16, 2017, 56(3): 733-737.
Li et al., "Synthesis and Evaluation of Camptothecin Antibody—Drug Conjugates", ACS Med Chem. Lett., 2019, 10(10): 1386-1392.
Lyon et al., "Reducing hydrophobicity of homogeneous antibody-drug conjugates improves pharmacokinetics and therapeutic index", Nat Biotechnol, 2015, 33: 733-735.
Mackenzie et al., "Strain-promoted cycloadditions involving nitrones and alkynes-rapid tunable reactions for bioorthogonal labeling", Curr Opin Chem Biol., 2014, 21: 81-88.
Nakada et al., "Novel antibody drug conjugates containing exatecan derivative-based cytotoxic payloads", Bioorg Med Chem Lett., Mar. 15, 2016, 26(6): 1542-1545.
Nicolaou et al., "Chemistry and biology of natural and designed enediynes", PNAS, 1993, 90(13): 5881-5888.
Ning et al., "Protein Modification by Strain-Promoted Alkyne-Nitrone Cycloaddition", Angewandte Chemie International Edition, 2010, 49(17): 3065-3068.
Nunes et al., "Use of a next generation maleimide in combination with THIOMABTM antibody technology delivers a highly stable, potent and near homogeneous THIOMABTM antibody-drug conjugate (TDC)", RSC Adv., 2017, 7: 24828-24832.
Park et al., "Aryl Sulfate is a Useful Motif for Conjugating and Releasing Phenolic Molecules: Sulfur Fluorine Exchange Click Chemistry Enables Discovery of Ortho-Hydroxy-Protected Aryl Sulfate Linker", Bioconjugate Chem, 2019, 30(7): 1957-1968.
Rodrigues et al., "Synthesis and p-lactamase-mediated activation of a cephalosporin-taxol prodrug", Chemistry Biology, 1995, 2: p. 223.
Salomon et al., "Optimizing Lysosomal Activation of Antibody—Drug Conjugates (ADCs) by Incorporation of Novel Cleavable Dipeptide Linkers", Mol Pharm., 2019, 16(12): 4817-4825.
Sletten et al., "A Bioorthogonal Quadricyclane Ligation", J Am Chem Soc, 2011, 133(44): 17570-17573.
Smith et al., "The Enediyne Antibiotics", J. Med. Chem., 1996, 39(11): 2103-2117.
Sonzini et al., "Improved Physical Stability of an Antibody—Drug Conjugate Using Host-Guest Chemistry", Bioconjug Chem., Jan. 15, 2020, 31(1): 123-129.
Staben et al., "Targeted drug delivery through the traceless release of tertiary and heteroaryl amines from antibody—drug conjugates", Nature Chemistry, Oct. 17, 2016, 8: 1112-1119.
Stockmann et al., "Exploring isonitrile-based click chemistry for ligation with biomolecules", Organic & Biomolecular Chemistry, 2011, 21: 7303-7305.
Strop et al., "RN927C, a Site-Specific Trop-2 Antibody-Drug Conjugate (ADC) with Enhanced Stability, Is Highly Efficacious in Preclinical Solid Tumor Models", Molecular Cancer Therapeutics, Aug. 31, 2016, 15(11): 2698-2708.
Strop et al., "Versatility of Microbial Transglutaminase", Bioconjugate Chemistry, 2014, 25(5): 855-862.
Su et al., "Modulating Antibody—Drug Conjugate Payload Metabolism by Conjugation Site and Linker Modification", Bioconjugate Chem., 2018, 29(4): 1155-1167.
Subedi et al., "The Structural Role of Antibody N-Glycosylation in Receptor Interactions", Structure, 2015, 23(9): 1573-1583.
Tsesmetzis et al., "Nucleobase and Nucleoside Analogues: Resistance and Re-Sensitisation at the Level of Pharmacokinetics, Pharmacodynamics and Metabolism", Cancers, 2018, 10(7): 240.
Walker et al., "Cleavage behavior of calicheamicin gamma 1 and calicheamicin T", PNAS USA, 1992, 89(10): 4608-4612.
Yarema et al., "Metabolic Delivery of Ketone Groups to Sialic Acid Residues. Application To Cell Surface Glycoform Engineering", Journal of Biological Chemistry, Nov. 1998, 273(47): 31168-31179.
Zhang et al., "Multifunctional Tumor-Targeting Cathepsin B-Sensitive Gemcitabine Prodrug Covalently Targets Albumin in Situ and Improves Cancer Therapy", Bioconjugate Chem., 2018, 29(6): 1852-1858.
Zhao et al., "Recent advances of antibody drug conjugates for clinical applications", Acta Pharmaceutica Sinica B, 2020, 10(9): 1589-1600.
Zheng et al., "The impact of glycosylation on monoclonal antibody conformation and stability", Mabs-Austin, 2011, 3(6): 568-576.
Borders et al., "Enediyne antibiotics as antitumor agents", J. Carbohydrate Chemistry, 1996, 15(5): 649-650.
Degruyter et al., "Residue-Specific Peptide Modification: A Chemist's Guide", Biochemistry, Aug. 1, 2017, 56(30): 3863-3873. Epub Jul. 17, 2017.
European Examination Report for European Patent Application No. 17742684.8, mailed Nov. 6, 2023.
Heckl et al., "The influence of 2,4,6-tribromophenyl isocyanate on the cellular and nuclear uptake of the SV 40 T antigen nuclear localization sequence", Eur. J. Pharmacol., Mar. 31, 2008, 583(1): 32-36. Epub Dec. 23, 2007.
International Search Report and Written Opinion for PCT International Patent Application No. PCT/EP2023/054455, dated May 22, 2023.
Jin et al., "Purification and characterization of a high-salt-resistant microbial transglutaminase from Streptomyces mobaraensis", J. Molecular Catalysis B: Enzymatic, Nov. 2016, 133: 6-11.
Kamiya et al., "S-peptide as a potent peptidyl linker for protein cross-linking by microbial transglutaminase from Streptomyces mobaraensis," Bioconj Chem., Mar.-Apr. 2003, 14(2): 351-357.
Leurs et al., "GnRH-III based multifunctional drug delivery systems containing daunorubicin and methotrexate", Eur. J. Med. Chem., Jun. 2012, 52: 173-83. Epub Mar. 16, 2012.
Ogitani et al., "DS-8201a, A Novel HER2-Targeting ADC with a Novel DNA Topoisomerase I Inhibitor, Demonstrates a Promising Antitumor Efficacy with Differentiation from T-DM1", Clin. Cancer Res., Oct. 15, 2016, 22(20): 5097-5108. Epub Mar. 29, 2016.
Plagmann et al., "Transglutaminase-catalyzed covalent multimerization of Camelidae anti-human TNF single domain antibodies improves neutralizing activity," J Biotechnol., Jun. 15, 2009, 142(2): 170-178.
Takazawa et al., "Enzymatic labeling of a single chain variable fragment of an antibody with alkaline phosphatase by microbial transglutaminase," Biotechnol Bioeng., May 20, 2004, 86(4): 399-404.
Yamazaki et al. "Antibody-drug conjugates with dual payloads for combating breast tumor heterogeneity and drug resistance", Nat. Commun., Jun. 10, 2021, 12(1): 3528.
Agarwal et al., "Site-specific antibody-drug conjugates: the nexus of bioorthogonal chemistry, protein engineering, and drug development", Bioconjug. Chem., Feb. 18, 2015, 26(2): 176-192, Epublished Jan. 30, 2015.
CAS Database Registry; Chemical Abstracts Service, CAS Registry No. 1346452-25-2, Immunoglobulin G1, anti-(human nectin-4), AFS 22ME (Enfortumab vedotin), Entered Nov. 28, 2011.
Chen et al., "Determination of Drug-to-Antibody Ratio for Antibody-Drug Conjugates Purified from Serum", Agilent Technologies, 2016, pp. 1-9.

(56) References Cited

OTHER PUBLICATIONS

Han et al., "The Potential of Topoisomerase Inhibitor-Based Antibody-Drug Conjugates", Pharmaceutics, 2022, 14(8): 1707.
Innate Pharma, A New Site Specific Antibody Conjugation Using Bacterial Transglutaminase, Innate Pharma, ADC Summit, San Francisco, Oct. 15, 2013, Retrieved from url: <https://www.innate-pharma.com/sites/default/files/iph_adc_summit_2013_0.pdf>.
International Search Report and Written Opinion for PCT International Patent Application No. PCT/EP2024/065351, dated Aug. 26, 2024.
International Search Report and Written Opinion for PCT International Patent Application No. PCT/EP2024/079076, dated Jan. 30, 2025.
Liu et al., "Fc-Engineering for Modulated Effector Functions-Improving Antibodies for Cancer Treatment", Antibodies (Basel), Nov. 17, 2020, 9(4): 64.
Ogitani et al., "Bystander killing effect of DS-8201a, a novel anti-human epidermal growth factor receptor 2 antibody-drug conjugate, in tumors with human epidermal growth factor receptor 2 heterogeneity", Cancer Sci., Jul. 2016, 107(7): 1039-1046, Epublished Jun. 22, 2016.
Pommier et al., "DNA Topoisomerase I Inhibitors: Chemistry, Biology, and Interfacial Inhibition", Chem Review, May 29, 2009, 109(7): 2894-2902.
Sauter et al., "Improving antibody-based therapies by chemical engineering of antibodies with multimeric cell-penetrating peptides for elevated intracellular delivery", Journal of Controlled Release, Jun. 10, 2020, 322: 200-208, Epublished Mar. 14, 2020.
Vidarsson et al., "IgG subclasses and allotypes: from structure to effector functions", Frontiers in Immunol., Oct. 20, 2014, 5(520): 1-17.
Yamaguchi et al., "Chemical generation of small molecule-based bispecific antibody-drug conjugates for broadening the target scope", Bioorg Med Chem., Feb. 15, 2021, 32: 116013, Epublished Jan. 9, 2021.
Yang et al., "Antitumor activity of a folate receptor-targeted immunoglobulin G-doxorubicin conjugate", Int J Nanomedicine, Mar. 30, 2017, 12: 2505-2515.
Zong et al., "Generating a Bispecific Antibody Drug Conjugate Targeting PRLR and HER2 with Improving the Internalization", Pharmaceut Fronts, Jul. 4, 2022, 4(2): e113-e120.

* cited by examiner

G A R K($N_3$)

Fig.5
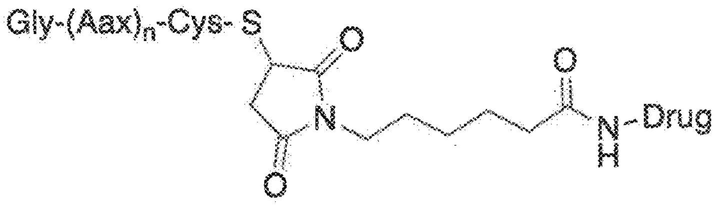
maleimidocaproyl (mc)
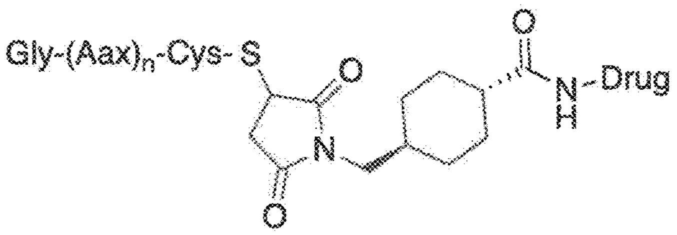
maleimidomethyl cyclohexane-1-carboxylate (mcc)
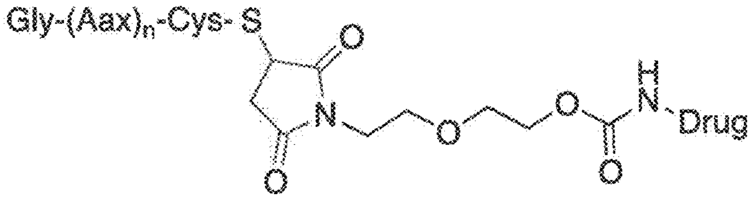
mc-like linker used in SYD985
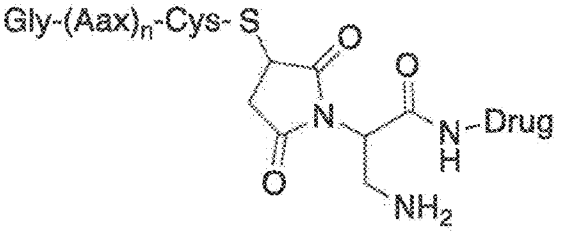
self-stabilizing maleimide Fig. 9
Structure 1
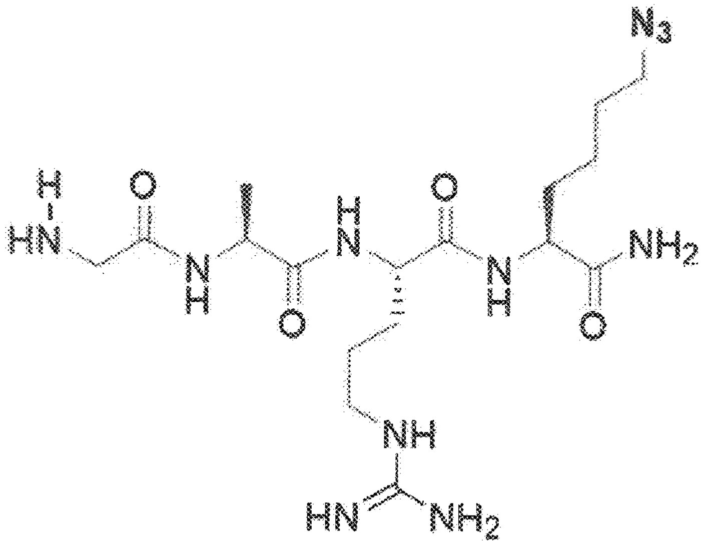
Structure 2
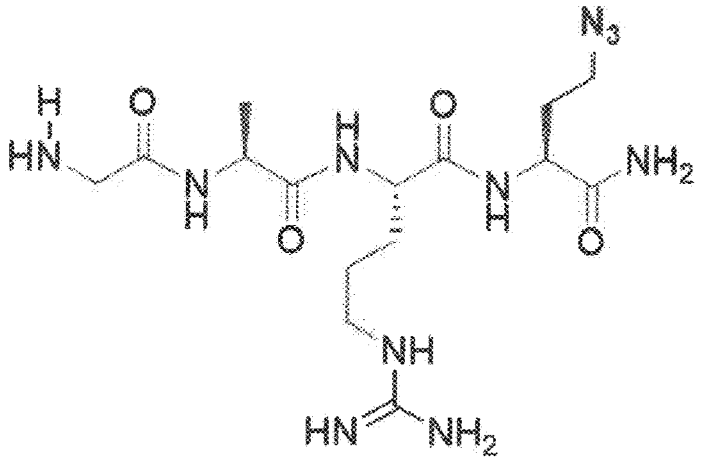

Fig. 9 ctd'
Structure 3
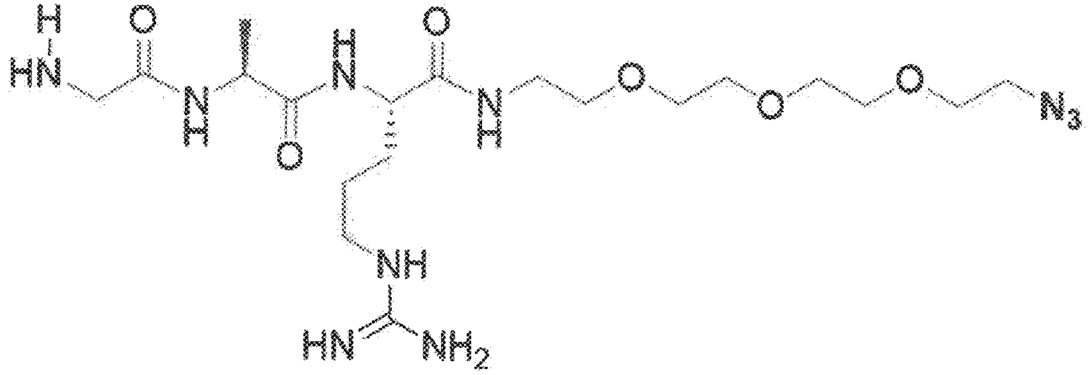
Structure 4
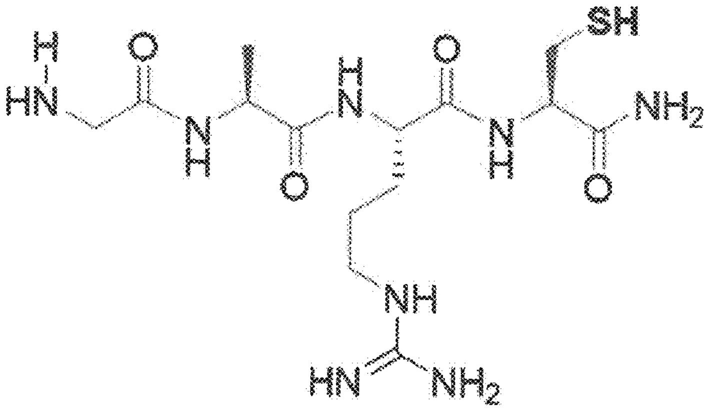

Fig. 9 ctd'
Structure 5
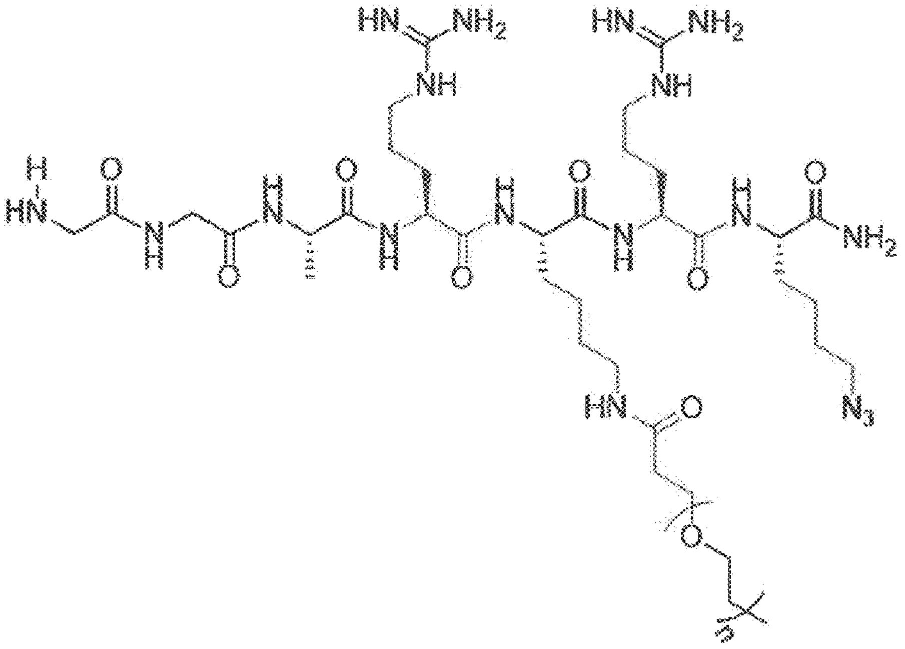

Fig. 13

| IMGT unique numbering for C-DOMAIN | CH2 IGHG1 amino acid translation J00228 (1) | IMGT exon numbering 1-110 | Eu numbering (1) (3) (110 aa) (2) 231-340 | Kabat numbering (2) | Strands, turns and loops for C-DOMAIN (5) |
|---|---|---|---|---|---|
| 1,8 | - | - | - | - | |
| 1,7 | - | - | - | - | |
| 1,6 | (A) | 1 | 231 | 244 | |
| 1,5 | P | 2 | 232 | 245 | |
| 1,4 | E | 3 | 233 | 246 | |
| 1,3 | L | 4 | 234 | 247 | |
| 1,2 | L | 5 | 235 | 248 | |
| 1,1 | G | 6 | 236 | 249 | |
| 1 | G | 7 | 237 | 250 | |
| 2 | P | 8 | 238 | 251 | |
| 3 | S | 9 | 239 | 252 | |
| 4 | V | 10 | 240 | 253 | |
| 5 | F | 11 | 241 | 254 | |
| 6 | L | 12 | 242 | 255 | |
| 7 | F | 13 | 243 | 256 | |
| 8 | P | 14 | 244 | 257 | A-STRAND |
| 9 | P | 15 | 245 | 258 | |
| 10 | K | 16 | 246 | 259 | |
| 11 | P | 17 | 247 | 260 | |
| 12 | K | 18 | 248 | 261 | |
| 13 | D | 19 | 249 | 262 | |
| 14 | T | 20 | 250 | 263 | |
| 15 | L | 21 | 251 | 264 | |
| 15,1 | M | 22 | 252 | 265 | |
| 15,2 | I | 23 | 253 | 266 | AB-TURN |
| 15,3 | - | - | - | - | |
| 16 | S | 24 | 254 | 267 | |
| 17 | R | 25 | 255 | 268 | |
| 18 | T | 26 | 256 | 269 | |
| 19 | P | 27 | 257 | 270 | |
| 20 | E | 28 | 258 | 271 | |
| 21 | V | 29 | 259 | 272 | B-STRAND |
| 22 | T | 30 | 260 | 273 | |
| 23 | C | 31 | 261 | 274 | |
| 24 | V | 32 | 262 | 275 | |
| 25 | V | 33 | 263 | 276 | |
| 26 | V | 34 | 264 | 277 | |
| 27 | D | 35 | 265 | 278 | |
| 28 | V | 36 | 266 | 279 | |
| 29 | S | 37 | 267 | 280 | |
| 30 | H | 38 | 268 | 281 | |
| 31 | E | 39 | 269 | 282 | BC-LOOP |
| 34 | D | 40 | 270 | 283 | |
| 35 | P | 41 | 271 | 284 | |
| 36 | E | 42 | 272 | 285 | |
| 37 | V | 43 | 273 | 286 | |
| 38 | K | 44 | 274 | 287 | |
| 39 | F | 45 | 275 | 288 | |
| 40 | N | 46 | 276 | 289 | |
| 41 | W | 47 | 277 | 290 | |
| 42 | Y | 48 | 278 | 291 | C-STRAND |
| 43 | V | 49 | 279 | 292 | |
| 44 | D | 50 | 280 | 295 | |
| 45 | G | 51 | 281 | 296 | |
| 45,1 | V | 52 | 282 | 299 | |
| 45,2 | E | 53 | 283 | 300 | |
| 45,3 | V | 54 | 284 | 301 | |
| 45,4 | H | 55 | 285 | 302 | CD-STRAND |
| 45,5 | - | - | - | - | |
| 45,6 | - | - | - | - | |
| 45,7 | - | - | - | - | |

| IMGT unique numbering for C-DOMAIN | CH2 IGHG1 amino acid translation J00228 (1) | IMGT exon numbering 1-110 | Eu numbering (1) (3) (110 aa) (2) 231-340 | Kabat numbering (2) | Strands, turns and loops for C-DOMAIN (5) |
|---|---|---|---|---|---|
| 77 | N | 56 | 286 | 303 | |
| 78 | A | 57 | 287 | 304 | |
| 79 | K | 58 | 288 | 305 | |
| 80 | T | 59 | 289 | 306 | D-STRAND |
| 81 | K | 60 | 290 | 307 | |
| 82 | P | 61 | 291 | 308 | |
| 83 | R | 62 | 292 | 309 | |
| 84 | E | 63 | 293 | 310 | |
| 84,1 | E | 64 | 294 | 311 | |
| 84,2 | Q | 65 | 295 | 312 | |
| 84,3 | Y | 66 | 296 | 313 | |
| 84,4 | N | 67 | 297 | 314 | |
| 84,5 | - | - | - | - | |
| 84.6 | - | - | - | - | |
| 84,7 | - | - | - | - | DE-TURN |
| 85,7 | - | - | - | - | |
| 85,6 | - | - | - | - | |
| 85.5 | - | - | - | - | |
| 85,4 | S | 68 | 298 | 317 | |
| 85,3 | T | 69 | 299 | 318 | |
| 85,2 | Y | 70 | 300 | 319 | |
| 85,1 | R | 71 | 301 | 320 | |
| 85 | V | 72 | 302 | 321 | |
| 86 | V | 73 | 303 | 322 | |
| 87 | S | 74 | 304 | 323 | |
| 88 | V | 75 | 305 | 324 | |
| 89 | L | 76 | 306 | 325 | |
| 90 | T | 77 | 307 | 326 | E-STRAND |
| 91 | V | 78 | 308 | 327 | |
| 92 | L | 79 | 309 | 328 | |
| 93 | H | 80 | 310 | 329 | |
| 94 | Q | 81 | 311 | 330 | |
| 95 | D | 82 | 312 | 331 | |
| 96 | W | 83 | 313 | 332 | |
| 96,1 | - | - | - | - | EF-TURN |
| 96,2 | - | - | - | - | |
| 97 | L | 84 | 314 | 333 | |
| 98 | N | 85 | 315 | 334 | |
| 99 | G | 86 | 316 | 335 | |
| 100 | K | 87 | 317 | 336 | F-STRAND |
| 101 | E | 88 | 318 | 337 | |
| 102 | Y | 89 | 319 | 338 | |
| 103 | K | 90 | 320 | 339 | |
| 104 | C | 91 | 321 | 340 | |
| 105 | K | 92 | 322 | 341 | |
| 106 | V | 93 | 323 | 342 | |
| 107 | S | 94 | 324 | 343 | |
| 108 | N | 95 | 325 | 344 | |
| 109 | K | 96 | 326 | 345 | |
| 110 | A | 97 | 327 | 346 | |
| 111 | - | - | - | - | FG-LOOP |
| 112 | - | - | - | - | |
| 113 | L | 98 | 328 | 347 | |
| 114 | P | 99 | 329 | 348 | |
| 115 | A | 100 | 330 | 349 | |
| 116 | P | 101 | 331 | 350 | |
| 117 | I | 102 | 332 | 351 | |
| 118 | E | 103 | 333 | 352 | |
| 119 | K | 104 | 334 | 353 | |
| 120 | T | 105 | 335 | 354 | |
| 121 | I | 106 | 336 | 355 | G-STRAND |
| 122 | S | 107 | 337 | 357 | |
| 123 | K | 108 | 338 | 358 | |
| 124 | A | 109 | 339 | 359 | |
| 125 | K | 110 | 340 | 360 | |

Antibody with Q295 having free primary amine ($NH_2$)

Oligopeptide having an N-terminal Gly residue

Formation of crosslinking isopeptidyl bond

Fig. 16
| | | |
|---|---|---|
| 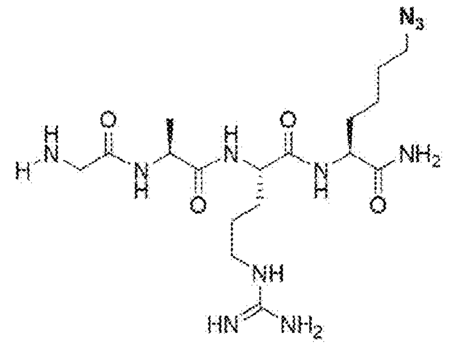 | GlyAlaArgLys(N3) | Lys(N3) comprises an Azide for click chemistry instead of a primary amine. |
| 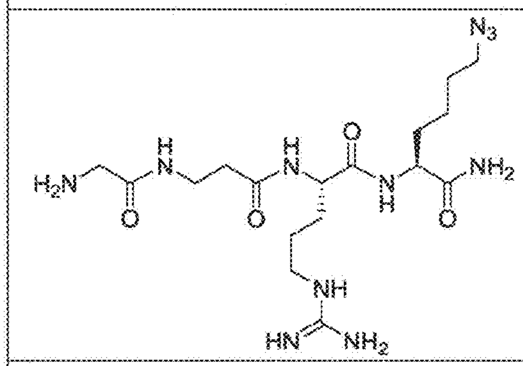 | GlyßAlaArgLys(N3) | ßAla does not make a peptide bond, hence this is an example for a peptidomimetic |
| 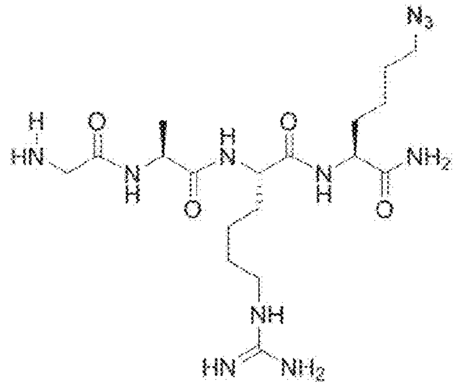 | GlyAla-homoArg-Lys(N3) | homoArg is a non naturally occurring amino acid |
| 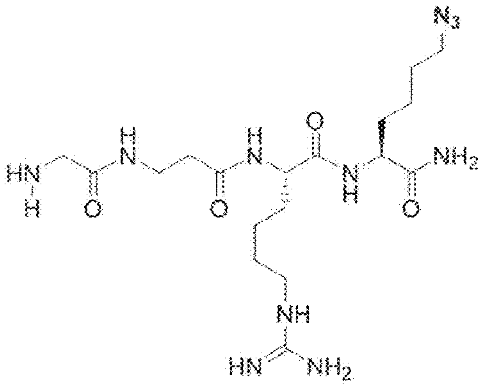 | GlyßAla-homoArg-Lys(N3) | Combination of the upper two |

SEQUENCE LISTING

```
<160> NUMBER OF SEQ ID NOS: 83

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: linker sequence
<220> FEATURE:
<221> NAME/KEY: MOD_RES
<222> LOCATION: (4)..(4)
<223> OTHER INFORMATION: 6-azido-L-lysine (Lys(N3))

<400> SEQUENCE: 1

Gly Ala Arg Lys
1


<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: linker sequence
<220> FEATURE:
```

-continued

<221> NAME/KEY: MOD_RES
<222> LOCATION: (4)..(4)
<223> OTHER INFORMATION: 6-azido-L-lysine (Lys(N3))
<220> FEATURE:
<221> NAME/KEY: MOD_RES
<222> LOCATION: (5)..(5)
<223> OTHER INFORMATION: Lys(tetrazine)

<400> SEQUENCE: 2

Gly Ala Arg Lys Lys
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: linker sequence
<220> FEATURE:
<221> NAME/KEY: MOD_RES
<222> LOCATION: (4)..(4)
<223> OTHER INFORMATION: 6-azido-L-lysine (Lys(N3))

<400> SEQUENCE: 3

Gly Ala Arg Lys Cys
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: linker sequence
<220> FEATURE:
<221> NAME/KEY: MOD_RES
<222> LOCATION: (5)..(5)
<223> OTHER INFORMATION: 6-azido-L-lysine (Lys(N3))
<220> FEATURE:
<221> NAME/KEY: MOD_RES
<222> LOCATION: (6)..(6)
<223> OTHER INFORMATION: 6-azido-L-lysine (Lys(N3))

<400> SEQUENCE: 4

Gly Gly Ala Arg Lys Lys
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: linker sequence
<220> FEATURE:
<221> NAME/KEY: MOD_RES
<222> LOCATION: (5)..(5)
<223> OTHER INFORMATION: 6-azido-L-lysine (Lys(N3))
<220> FEATURE:
<221> NAME/KEY: MOD_RES
<222> LOCATION: (7)..(7)
<223> OTHER INFORMATION: 6-azido-L-lysine (Lys(N3))

```
<400> SEQUENCE: 5

Gly Gly Ala Arg Lys Arg Lys
1               5


<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: linker sequence
<220> FEATURE:
<221> NAME/KEY: MOD_RES
<222> LOCATION: (4)..(4)
<223> OTHER INFORMATION: 4-azido-L-homoalanine

<400> SEQUENCE: 6

Gly Ala Arg Ala
1


<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: linker sequence

<400> SEQUENCE: 7

Gly Ala Arg Cys
1


<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: linker sequence
<220> FEATURE:
<221> NAME/KEY: MOD_RES
<222> LOCATION: (2)..(2)
<223> OTHER INFORMATION: Beta-Alanine

<400> SEQUENCE: 8

Gly Ala Arg Lys
1


<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: linker sequence
<220> FEATURE:
<221> NAME/KEY: MOD_RES
<222> LOCATION: (3)..(3)
<223> OTHER INFORMATION: homoarginine
<220> FEATURE:
<221> NAME/KEY: MOD_RES
<222> LOCATION: (4)..(4)
```

<223> OTHER INFORMATION: 6-azido-L-lysine (Lys(N3))

<400> SEQUENCE: 9

Gly Ala Arg Lys
1

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: linker sequence
<220> FEATURE:
<221> NAME/KEY: MOD_RES
<222> LOCATION: (2)..(2)
<223> OTHER INFORMATION: Beta-Alanine
<220> FEATURE:
<221> NAME/KEY: MOD_RES
<222> LOCATION: (3)..(3)
<223> OTHER INFORMATION: Homoarginine
<220> FEATURE:
<221> NAME/KEY: MOD_RES
<222> LOCATION: (4)..(4)
<223> OTHER INFORMATION: 6-azido-L-lysine (Lys(N3))

<400> SEQUENCE: 10

Gly Ala Arg Lys
1

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: linker sequence

<400> SEQUENCE: 11

Gly Gly Ala Arg Arg
1 5

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: linker sequence
<220> FEATURE:
<221> NAME/KEY: MOD_RES
<222> LOCATION: (4)..(4)
<223> OTHER INFORMATION: 6-azido-L-lysine (Lys(N3))

<400> SEQUENCE: 12

Gly Arg Ala Lys
1

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
peptide <220> FEATURE:
<223> OTHER INFORMATION: linker sequence

<400> SEQUENCE: 13

Gly Arg Ala Cys
1

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: linker sequence
<220> FEATURE:
<221> NAME/KEY: MOD_RES
<222> LOCATION: (4)..(4)
<223> OTHER INFORMATION: 6-azido-L-lysine (Lys(N3))

<400> SEQUENCE: 14

Gly Gly Arg Lys
1

<210> SEQ ID NO 15
<211> LENGTH: 3
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: linker sequence
<220> FEATURE:
<221> NAME/KEY: MOD_RES
<222> LOCATION: (3)..(3)
<223> OTHER INFORMATION: 6-azido-L-lysine (Lys(N3))

<400> SEQUENCE: 15

Gly Arg Lys
1

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: linker sequence
<220> FEATURE:
<221> NAME/KEY: MOD_RES
<222> LOCATION: (4)..(4)
<223> OTHER INFORMATION: 6-azido-L-lysine (Lys(N3))

<400> SEQUENCE: 16

Gly Gly Arg Lys Arg
1 5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: linker sequence
<220> FEATURE:

<221> NAME/KEY: MOD_RES
<222> LOCATION: (3)..(3)
<223> OTHER INFORMATION: 6-azido-L-lysine (Lys(N3))

<400> SEQUENCE: 17

Gly Gly Lys Arg Cys
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: linker sequence
<220> FEATURE:
<221> NAME/KEY: MOD_RES
<222> LOCATION: (5)..(5)
<223> OTHER INFORMATION: 6-azido-L-lysine (Lys(N3))

<400> SEQUENCE: 18

Gly Gly Arg Arg Lys
1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: linker sequence
<220> FEATURE:
<221> NAME/KEY: MOD_RES
<222> LOCATION: (4)..(4)
<223> OTHER INFORMATION: 6-azido-L-lysine (Lys(N3))

<400> SEQUENCE: 19

Gly Gly Arg Lys Arg
1               5

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: linker sequence
<220> FEATURE:
<221> NAME/KEY: MOD_RES
<222> LOCATION: (4)..(4)
<223> OTHER INFORMATION: 6-azido-L-lysine (Lys(N3))

<400> SEQUENCE: 20

Gly Ala His Lys
1

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: linker sequence -continued
<220> FEATURE:
<221> NAME/KEY: MOD_RES
<222> LOCATION: (4)..(4)
<223> OTHER INFORMATION: 6-azido-L-lysine (Lys(N3))

<400> SEQUENCE: 21

Gly Gly His Lys
1

<210> SEQ ID NO 22
<211> LENGTH: 2
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: linker sequence

<400> SEQUENCE: 22

Gly Cys
1

<210> SEQ ID NO 23
<211> LENGTH: 4
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: linker sequence

<400> SEQUENCE: 23

Gly Gly Arg Cys
1

<210> SEQ ID NO 24
<211> LENGTH: 3
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: linker sequence

<400> SEQUENCE: 24

Gly Arg Cys
1

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: linker sequence
<220> FEATURE:
<221> NAME/KEY: MOD_RES
<222> LOCATION: (4)..(4)
<223> OTHER INFORMATION: 6-azido-L-lysine (Lys(N3))

<400> SEQUENCE: 25

Gly Gly Arg Lys
1

-continued

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: linker sequence
<220> FEATURE:
<221> NAME/KEY: MOD_RES
<222> LOCATION: (5)..(5)
<223> OTHER INFORMATION: 6-azido-L-lysine (Lys(N3))

<400> SEQUENCE: 26

```
Gly Gly Ala Lys Lys
1               5
```

<210> SEQ ID NO 27
<211> LENGTH: 395
<212> TYPE: PRT
<213> ORGANISM: Streptoverticillium ladakanum

<400> SEQUENCE: 27

```
Met His Arg Arg Ile His Ala Val Gly Gln Ala Arg Pro Pro Pro Thr
1               5                   10                  15

Met Ala Arg Gly Lys Glu Thr Lys Ser Tyr Ala Glu Thr Tyr Arg Leu
            20                  25                  30

Thr Ala Asp Asp Val Ala Asn Ile Asn Ala Leu Asn Glu Ser Ala Pro
        35                  40                  45

Ala Ala Ser Ser Ala Gly Pro Ser Phe Arg Ala Pro Asp Ser Asp Asp
    50                  55                  60

Arg Val Thr Pro Pro Ala Glu Pro Leu Asp Arg Met Pro Asp Pro Tyr
65                  70                  75                  80

Arg Pro Ser Tyr Gly Arg Ala Glu Thr Val Val Asn Asn Tyr Ile Arg
                85                  90                  95

Lys Trp Gln Gln Val Tyr Ser His Arg Asp Gly Arg Lys Gln Gln Met
            100                 105                 110

Thr Glu Glu Gln Arg Glu Trp Leu Ser Tyr Gly Cys Val Gly Val Thr
        115                 120                 125

Trp Val Asn Ser Gly Gln Tyr Pro Thr Asn Arg Leu Ala Phe Ala Ser
    130                 135                 140

Phe Asp Glu Asp Arg Phe Lys Asn Glu Leu Lys Asn Gly Arg Pro Arg
145                 150                 155                 160

Ser Gly Glu Thr Arg Ala Glu Phe Glu Gly Arg Val Ala Lys Glu Ser
                165                 170                 175

Phe Asp Glu Glu Lys Gly Phe Gln Arg Ala Arg Glu Val Ala Ser Val
            180                 185                 190

Met Asn Arg Ala Leu Glu Asn Ala His Asp Glu Ser Ala Tyr Leu Asp
        195                 200                 205

Asn Leu Lys Lys Glu Leu Ala Asn Gly Asn Asp Ala Leu Arg Asn Glu
    210                 215                 220

Asp Ala Arg Ser Pro Phe Tyr Ser Ala Leu Arg Asn Thr Pro Ser Phe
225                 230                 235                 240

Lys Glu Arg Asn Gly Gly Asn His Asp Pro Ser Arg Met Lys Ala Val
                245                 250                 255

Ile Tyr Ser Lys His Phe Trp Ser Gly Gln Asp Arg Ser Ser Ser Ala
            260                 265                 270
```

```
Asp Lys Arg Lys Tyr Gly Asp Pro Asp Ala Phe Arg Ser Ala Pro Gly
        275                 280                 285

Thr Gly Leu Val Asp Met Ser Arg Asp Arg Asn Ile Pro Arg Ser Pro
    290                 295                 300

Thr Ser Pro Gly Glu Gly Phe Val Asn Phe Asp Tyr Gly Trp Phe Gly
305                 310                 315                 320

Ala Gln Thr Glu Ala Asp Ala Asp Lys Thr Val Trp Thr His Gly Asn
                325                 330                 335

His Tyr His Ala Pro Asn Gly Ser Leu Gly Cys His Ala Cys Leu Thr
            340                 345                 350

Arg Ala Ser Ser Ala Thr Gly Ser Glu Gly Tyr Ser Asp Phe Asp Arg
        355                 360                 365

Gly Glu Pro Tyr Val Val Ser Pro Ser Pro Ser Pro Arg Met Leu Glu
    370                 375                 380

His Arg Pro Arg Gln Gly Lys Ala Gly Leu Ala
385                 390                 395
```

```
<210> SEQ ID NO 28
<211> LENGTH: 335
<212> TYPE: PRT
<213> ORGANISM: Streptomyces mobaraensis

<400> SEQUENCE: 28

Phe Arg Ala Pro Asp Ser Asp Glu Arg Val Thr Pro Pro Ala Glu Pro
1               5                   10                  15

Leu Asp Arg Met Pro Asp Pro Tyr Arg Pro Ser Tyr Gly Arg Ala Glu
            20                  25                  30

Thr Ile Val Asn Asn Tyr Ile Arg Lys Trp Gln Gln Val Tyr Ser His
        35                  40                  45

Arg Asp Gly Arg Lys Gln Gln Met Thr Glu Glu Gln Arg Glu Trp Leu
    50                  55                  60

Ser Tyr Gly Cys Val Gly Val Thr Trp Val Asn Ser Gly Gln Tyr Pro
65                  70                  75                  80

Thr Asn Arg Leu Ala Phe Ala Phe Phe Asp Glu Asp Lys Tyr Lys Asn
                85                  90                  95

Glu Leu Lys Asn Gly Arg Pro Arg Ser Gly Glu Thr Arg Ala Glu Phe
            100                 105                 110

Glu Gly Arg Val Ala Lys Asp Ser Phe Asp Glu Ala Lys Gly Phe Gln
        115                 120                 125

Arg Ala Arg Asp Val Ala Ser Val Met Asn Lys Ala Leu Glu Asn Ala
    130                 135                 140

His Asp Glu Gly Ala Tyr Leu Asp Asn Leu Lys Lys Glu Leu Ala Asn
145                 150                 155                 160

Gly Asn Asp Ala Leu Arg Asn Glu Asp Ala Arg Ser Pro Phe Tyr Ser
                165                 170                 175

Ala Leu Arg Asn Thr Pro Ser Phe Lys Asp Arg Asn Gly Gly Asn His
            180                 185                 190

Asp Pro Ser Lys Met Lys Ala Val Ile Tyr Ser Lys His Phe Trp Ser
        195                 200                 205

Gly Gln Asp Arg Ser Gly Ser Ser Asp Lys Arg Lys Tyr Gly Asp Pro
    210                 215                 220

Glu Ala Phe Arg Pro Asp Arg Gly Thr Gly Leu Val Asp Met Ser Arg
225                 230                 235                 240
```

Asp Arg Asn Ile Pro Arg Ser Pro Thr Ser Pro Gly Glu Ser Phe Val
245 250 255

Asn Phe Asp Tyr Gly Trp Phe Gly Ala Gln Thr Glu Ala Asp Ala Asp
260 265 270

Lys Thr Val Trp Thr His Gly Asn His Tyr His Ala Pro Asn Gly Ser
275 280 285

Leu Gly Ala Met His Val Tyr Glu Ser Lys Phe Arg Asn Trp Ser Asp
290 295 300

Gly Tyr Ser Asp Phe Asp Arg Gly Ala Tyr Val Val Thr Phe Val Pro
305 310 315 320

Lys Ser Trp Asn Thr Ala Pro Asp Lys Val Thr Gln Gly Trp Pro
325 330 335

<210> SEQ ID NO 29
<211> LENGTH: 3
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: linker sequence
<220> FEATURE:
<223> OTHER INFORMATION: C-Term [PEG]3N3

<400> SEQUENCE: 29

Gly Ala Arg
1

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: linker sequence
<220> FEATURE:
<221> NAME/KEY: MOD_RES
<222> LOCATION: (5)..(5)
<223> OTHER INFORMATION: Lys(PEG)n
<220> FEATURE:
<221> NAME/KEY: MOD_RES
<222> LOCATION: (7)..(7)
<223> OTHER INFORMATION: 6-azido-L-lysine (Lys(N3))

<400> SEQUENCE: 30

Gly Gly Ala Arg Lys Arg Lys
1 5

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: linker sequence
<220> FEATURE:
<221> NAME/KEY: MOD_RES
<222> LOCATION: (5)..(5)
<223> OTHER INFORMATION: 6-azido-L-lysine (Lys(N3))

<400> SEQUENCE: 31

Gly Gly Ala Arg Lys
1 5

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: linker sequence
<220> FEATURE:
<221> NAME/KEY: MOD_RES
<222> LOCATION: (1)..(1)
<223> OTHER INFORMATION: beta-alanine
<220> FEATURE:
<221> NAME/KEY: MOD_RES
<222> LOCATION: (5)..(5)
<223> OTHER INFORMATION: 6-azido-L-lysine (Lys(N3))

<400> SEQUENCE: 32

Ala Gly Ala Arg Lys
1 5

<210> SEQ ID NO 33
<211> LENGTH: 3
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: linker sequence

<400> SEQUENCE: 33

Gly Ala Arg
1

<210> SEQ ID NO 34
<211> LENGTH: 4
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: linker sequence

<400> SEQUENCE: 34

Gly Ala Arg Arg
1

<210> SEQ ID NO 35
<211> LENGTH: 4
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: linker sequence

<400> SEQUENCE: 35

Gly Gly Ala Arg
1

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: linker sequence

<400> SEQUENCE: 36

Gly Gly Ala Arg Arg
1 5

<210> SEQ ID NO 37
<211> LENGTH: 3
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: linker sequence

<400> SEQUENCE: 37

Gly Gly Gly
1

<210> SEQ ID NO 38
<211> LENGTH: 3
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: linker sequence

<400> SEQUENCE: 38

Gly Asp Cys
1

<210> SEQ ID NO 39
<211> LENGTH: 4
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: linker sequence

<400> SEQUENCE: 39

Gly Arg Cys Asp
1

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: linker sequence

<400> SEQUENCE: 40

Gly Arg Asp Cys
1

<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: linker sequence

<400> SEQUENCE: 41

Gly Gly Asp Cys
1

<210> SEQ ID NO 42
<211> LENGTH: 4
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: linker sequence

<400> SEQUENCE: 42

Gly Gly Cys Asp
1

<210> SEQ ID NO 43
<211> LENGTH: 4
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: linker sequence

<400> SEQUENCE: 43

Gly Gly Glu Cys
1

<210> SEQ ID NO 44
<211> LENGTH: 4
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: linker sequence
<220> FEATURE:
<221> NAME/KEY: MOD_RES
<222> LOCATION: (3)..(3)
<223> OTHER INFORMATION: 6-azido-L-lysine (Lys(N3))

<400> SEQUENCE: 44

Gly Gly Lys Asp
1

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: linker sequence

```
<400> SEQUENCE: 45

Gly Gly Arg Cys Asp
1               5


<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: linker sequence

<400> SEQUENCE: 46

Gly Gly Gly Asp Cys
1               5


<210> SEQ ID NO 47
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: linker sequence
<220> FEATURE:
<221> NAME/KEY: MOD_RES
<222> LOCATION: (4)..(4)
<223> OTHER INFORMATION: 6-azido-L-lysine (Lys(N3))

<400> SEQUENCE: 47

Gly Gly Gly Lys
1


<210> SEQ ID NO 48
<211> LENGTH: 335
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Streptomyces mobaraensis MTG Zedira

<400> SEQUENCE: 48

Phe Arg Ala Pro Asp Ser Asp Asp Arg Val Thr Pro Pro Ala Glu Pro
1               5                   10                  15

Leu Asp Arg Met Pro Asp Pro Tyr Arg Pro Ser Tyr Gly Arg Ala Glu
            20                  25                  30

Thr Val Val Asn Asn Tyr Ile Arg Lys Trp Gln Gln Val Tyr Ser His
        35                  40                  45

Arg Asp Gly Arg Lys Gln Gln Met Thr Glu Glu Gln Arg Glu Trp Leu
    50                  55                  60

Ser Tyr Gly Cys Val Gly Val Thr Trp Val Asn Ser Gly Gln Tyr Pro
65                  70                  75                  80

Thr Asn Arg Leu Ala Phe Ala Ser Phe Asp Glu Asp Arg Phe Lys Asn
                85                  90                  95

Glu Leu Lys Asn Gly Arg Pro Arg Ser Gly Glu Thr Arg Ala Glu Phe
            100                 105                 110

Glu Gly Arg Val Ala Lys Glu Ser Phe Asp Glu Glu Lys Gly Phe Gln
        115                 120                 125
```

-continued

```
Arg Ala Arg Glu Val Ala Ser Val Met Asn Arg Ala Leu Glu Asn Ala
    130                 135                 140

His Asp Glu Ser Ala Tyr Leu Asp Asn Leu Lys Lys Glu Leu Ala Asn
145                 150                 155                 160

Gly Asn Asp Ala Leu Arg Asn Glu Asp Ala Arg Ser Pro Phe Tyr Ser
                165                 170                 175

Ala Leu Arg Asn Thr Pro Ser Phe Lys Glu Arg Asn Gly Gly Asn His
            180                 185                 190

Asp Pro Ser Arg Met Lys Ala Val Ile Tyr Ser Lys His Phe Trp Ser
        195                 200                 205

Gly Gln Asp Arg Ser Ser Ser Ala Asp Lys Arg Lys Tyr Gly Asp Pro
    210                 215                 220

Asp Ala Phe Arg Pro Ala Pro Gly Thr Gly Leu Val Asp Met Ser Arg
225                 230                 235                 240

Asp Arg Asn Ile Pro Arg Ser Pro Thr Ser Pro Gly Glu Gly Phe Val
                245                 250                 255

Asn Phe Asp Tyr Gly Trp Phe Gly Ala Gln Thr Glu Ala Asp Ala Asp
            260                 265                 270

Lys Thr Val Trp Thr His Gly Asn His Tyr His Ala Pro Asn Gly Ser
        275                 280                 285

Leu Gly Ala Met His Val Tyr Glu Ser Lys Phe Arg Asn Trp Ser Glu
    290                 295                 300

Gly Tyr Ser Asp Phe Asp Arg Gly Ala Tyr Val Ile Thr Phe Ile Pro
305                 310                 315                 320

Lys Ser Trp Asn Thr Ala Pro Asp Lys Val Lys Gln Gly Trp Pro
                325                 330                 335


<210> SEQ ID NO 49
<211> LENGTH: 407
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Streptomyces mobaraensis MTG P81453

<400> SEQUENCE: 49

Met Arg Ile Arg Arg Arg Ala Leu Val Phe Ala Thr Met Ser Ala Val
1               5                   10                  15

Leu Cys Thr Ala Gly Phe Met Pro Ser Ala Gly Glu Ala Ala Ala Asp
            20                  25                  30

Asn Gly Ala Gly Glu Glu Thr Lys Ser Tyr Ala Glu Thr Tyr Arg Leu
        35                  40                  45

Thr Ala Asp Asp Val Ala Asn Ile Asn Ala Leu Asn Glu Ser Ala Pro
    50                  55                  60

Ala Ala Ser Ser Ala Gly Pro Ser Phe Arg Ala Pro Asp Ser Asp Asp
65                  70                  75                  80

Arg Val Thr Pro Pro Ala Glu Pro Leu Asp Arg Met Pro Asp Pro Tyr
                85                  90                  95

Arg Pro Ser Tyr Gly Arg Ala Glu Thr Val Val Asn Asn Tyr Ile Arg
            100                 105                 110

Lys Trp Gln Gln Val Tyr Ser His Arg Asp Gly Arg Lys Gln Gln Met
        115                 120                 125

Thr Glu Glu Gln Arg Glu Trp Leu Ser Tyr Gly Cys Val Gly Val Thr
    130                 135                 140
```

Trp Val Asn Ser Gly Gln Tyr Pro Thr Asn Arg Leu Ala Phe Ala Ser
145 150 155 160

Phe Asp Glu Asp Arg Phe Lys Asn Glu Leu Lys Asn Gly Arg Pro Arg
165 170 175

Ser Gly Glu Thr Arg Ala Glu Phe Glu Gly Arg Val Ala Lys Glu Ser
180 185 190

Phe Asp Glu Glu Lys Gly Phe Gln Arg Ala Arg Glu Val Ala Ser Val
195 200 205

Met Asn Arg Ala Leu Glu Asn Ala His Asp Glu Ser Ala Tyr Leu Asp
210 215 220

Asn Leu Lys Lys Glu Leu Ala Asn Gly Asn Asp Ala Leu Arg Asn Glu
225 230 235 240

Asp Ala Arg Ser Pro Phe Tyr Ser Ala Leu Arg Asn Thr Pro Ser Phe
245 250 255

Lys Glu Arg Asn Gly Gly Asn His Asp Pro Ser Arg Met Lys Ala Val
260 265 270

Ile Tyr Ser Lys His Phe Trp Ser Gly Gln Asp Arg Ser Ser Ser Ala
275 280 285

Asp Lys Arg Lys Tyr Gly Asp Pro Asp Ala Phe Arg Pro Ala Pro Gly
290 295 300

Thr Gly Leu Val Asp Met Ser Arg Asp Arg Asn Ile Pro Arg Ser Pro
305 310 315 320

Thr Ser Pro Gly Glu Gly Phe Val Asn Phe Asp Tyr Gly Trp Phe Gly
325 330 335

Ala Gln Thr Glu Ala Asp Ala Asp Lys Thr Val Trp Thr His Gly Asn
340 345 350

His Tyr His Ala Pro Asn Gly Ser Leu Gly Ala Met His Val Tyr Glu
355 360 365

Ser Lys Phe Arg Asn Trp Ser Glu Gly Tyr Ser Asp Phe Asp Arg Gly
370 375 380

Ala Tyr Val Ile Thr Phe Ile Pro Lys Ser Trp Asn Thr Ala Pro Asp
385 390 395 400

Lys Val Lys Gln Gly Trp Pro
405

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: Q-Tag 1

<400> SEQUENCE: 50

Leu Leu Gln Gly Gly
1 5

<210> SEQ ID NO 51
<211> LENGTH: 4
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: Q-Tag 2

<400> SEQUENCE: 51

Leu Leu Gln Gly
1

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Q-Tag 3

<400> SEQUENCE: 52

Leu Ser Leu Ser Gln Gly
1 5

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Q-Tag 4

<400> SEQUENCE: 53

Gly Gly Gly Leu Leu Gln Gly Gly
1 5

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Q-Tag 5

<400> SEQUENCE: 54

Gly Leu Leu Gln Gly
1 5

<210> SEQ ID NO 55
<211> LENGTH: 3
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Q-Tag 6

<400> SEQUENCE: 55

Leu Leu Gln
1

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Q-Tag 7

-continued

<400> SEQUENCE: 56

Gly Ser Pro Leu Ala Gln Ser His Gly Gly
1 5 10

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: Q-Tag 8

<400> SEQUENCE: 57

Gly Leu Leu Gln Gly Gly Gly
1 5

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: Q-Tag 9

<400> SEQUENCE: 58

Gly Leu Leu Gln Gly Gly
1 5

<210> SEQ ID NO 59
<211> LENGTH: 4
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: Q-Tag 10

<400> SEQUENCE: 59

Gly Leu Leu Gln
1

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: Q-Tag 11

<400> SEQUENCE: 60

Leu Leu Gln Leu Leu Gln Gly Ala
1 5

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic peptide
<220> FEATURE:

<223> OTHER INFORMATION: Q-Tag 12

<400> SEQUENCE: 61

Leu Leu Gln Gly Ala
1 5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Q-Tag 13

<400> SEQUENCE: 62

Leu Leu Gln Tyr Gln Gly Ala
1 5

<210> SEQ ID NO 63
<211> LENGTH: 6
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Q-Tag 14

<400> SEQUENCE: 63

Leu Leu Gln Gly Ser Gly
1 5

<210> SEQ ID NO 64
<211> LENGTH: 6
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Q-Tag 15

<400> SEQUENCE: 64

Leu Leu Gln Tyr Gln Gly
1 5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Q-Tag 16

<400> SEQUENCE: 65

Leu Leu Gln Leu Leu Gln Gly
1 5

<210> SEQ ID NO 66
<211> LENGTH: 5
<212> TYPE: PRT
<213> ORGANISM: Artificial Sequence
<220> FEATURE:
<223> OTHER INFORMATION: Description of Artificial Sequence: Synthetic
peptide -continued <220> FEATURE:
<223> OTHER INFORMATION: Q-Tag 17

<400> SEQUENCE: 66

Ser Leu Leu Gln Gly
1               5

<210> SEQ ID NO 67
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Q-Tag 18

<400> SEQUENCE: 67

Leu Leu Gln Leu Gln
1               5

<210> SEQ ID NO 68
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Q-Tag 19

<400> SEQUENCE: 68

Leu Leu Gln Leu Leu Gln
1               5

<210> SEQ ID NO 69
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Q-Tag 20

<400> SEQUENCE: 69

Leu Leu Gln Gly Arg
1               5

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Q-Tag 21

<400> SEQUENCE: 70

Glu Glu Gln Tyr Ala Ser Thr Tyr
1               5

<210> SEQ ID NO 71
<211> LENGTH: 8
<212> TYPE: PRT
<213> ORGANISM: Artificial Sequence -continued

```
<220> FEATURE:
<223> OTHER INFORMATION: Description of Artificial Sequence: Synthetic
      peptide
<220> FEATURE:
<223> OTHER INFORMATION: Q-Tag 22

<400> SEQUENCE: 71

Glu Glu Gln Tyr Gln Ser Thr Tyr
1               5


<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Q-Tag 23

<400> SEQUENCE: 72

Glu Glu Gln Tyr Asn Ser Thr Tyr
1               5


<210> SEQ ID NO 73
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Q-Tag 24

<400> SEQUENCE: 73

Glu Glu Gln Tyr Gln Ser
1               5


<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Q-Tag 25

<400> SEQUENCE: 74

Glu Glu Gln Tyr Gln Ser Thr
1               5


<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Q-Tag 26

<400> SEQUENCE: 75

Glu Gln Tyr Gln Ser Thr Tyr
1               5


<210> SEQ ID NO 76
<211> LENGTH: 4
<212> TYPE: PRT
```

<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Q-Tag 27

<400> SEQUENCE: 76

Gln Tyr Gln Ser
1

<210> SEQ ID NO 77
<211> LENGTH: 6
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Q-Tag 28

<400> SEQUENCE: 77

Gln Tyr Gln Ser Thr Tyr
1 5

<210> SEQ ID NO 78
<211> LENGTH: 5
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Q-Tag 29

<400> SEQUENCE: 78

Tyr Arg Tyr Arg Gln
1 5

<210> SEQ ID NO 79
<211> LENGTH: 5
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Q-Tag 30

<400> SEQUENCE: 79

Asp Tyr Ala Leu Gln
1 5

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: Q-Tag 31

<400> SEQUENCE: 80

Phe Gly Leu Gln Arg Pro Tyr
1 5

<210> SEQ ID NO 81
<211> LENGTH: 10

-continued

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Q-Tag 32

<400> SEQUENCE: 81

Glu Gln Lys Leu Ile Ser Glu Glu Asp Leu
1               5                   10


<210> SEQ ID NO 82
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Q-Tag 33

<400> SEQUENCE: 82

Leu Gln Arg
1


<210> SEQ ID NO 83
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Q-Tag 34

<400> SEQUENCE: 83

Tyr Gln Arg
1
```

TRANSGLUTAMINASE CONJUGATION METHOD WITH A GLYCINE BASED LINKER

RELATED APPLICATIONS

This application is a 35 U.S.C. § 371 filing of International Patent Application No. PCT/EP2020/057697, filed Mar. 19, 2020, which claims priority to European Application No. 19163810.5, filed Mar. 19, 2019, the entire disclosures of which are incorporated herein by reference.

SEQUENCE LISTING

The instant application contains a Sequence Listing which has been submitted electronically in ASCII format and is hereby incorporated by reference in its entirety. Said ASCII copy, created on Sep. 29, 2021, is named 721385_ARA9-003US_SL.txt and is 33,475 bytes in size.

FIELD OF THE INVENTION

The present invention relates to methods for generating an antibody-payload conjugate by means of a microbial transglutaminase. The invention further provides linkers, linker-payload constructs and/or antibody-payload constructs.

BACKGROUND OF THE INVENTION

Attaching highly potent payloads to antibodies finds increasing interest for the targeted treatment of cancer or inflammatory diseases. The constructs this produces are called antibody-payload conjugates, or antibody-drug conjugates (ADC).

Currently, seven ADCs have gained FDA-approval (Adcetris, Kadcyla, Besponsa, Mylotarg, Polivy, Padcev, Enhertu), all of which have their payload chemically attached to the antibody in a non-site specific manner. Hence, the resulting product is highly heterogeneous, both with respect to the stoichiometric relationship between antibody and payload (payload-antibody ratio, or drug-to-antibody ratio, DAR), as well concerning the conjugation sites on the antibody. Each of the resulting species, although in the same drug product, may have distinct properties that could potentially lead to a wide range of different in vivo pharmacokinetic properties and activities.

In a previous in vivo study (Lhospice et al., 2015), it was shown that a site-specific drug attachment led to a significant higher tumor uptake (~2×) and a decreased uptake in non-targeted tissues compared to the FDA-approved ADC, also the maximal tolerated dose was at least 3× higher. These data suggest that stoichiometrically well-defined ADCs display improved pharmacokinetics and better therapeutic indexes compared to chemically modified ADCs.

As a site-specific technology, enzymatic conjugation has gained great interest since these conjugation reactions are typically fast and can be performed under physiological conditions. Among the available enzymes, microbial transglutaminase (MTG) from the species *Streptomyces mobaraensis* has gained increasing interest as an attractive alternative to conventional chemical protein conjugation of functional moieties including antibodies. The MTG catalyzes under physiological conditions a transamidation reaction between a 'reactive' glutamine of a protein or peptide and a 'reactive' lysine residue of a protein or peptide, whereas the latter can also be a simple, low molecular weight primary amine such as a 5-aminopentyl group (Jeger et al., 2010, Strop et al., 2014).

The bond formed is an isopeptide bond which is an amide bond that does not form part of the peptide-bond backbone of the respective polypeptide or protein. It is formed between the γ-carboxamide of the glutamyl residue of the acyl glutamine-containing amino acid donor sequence and a primary (1°) amine of the amino donor-comprising substrate according to the invention.

From the inventor's experience as well as from others, it seems that only few glutamines are typically targeted by MTG, thus making the MTG an attractive tool for site-specific and stoichiometric protein modifications.

Previously, glutamine 295 (Q295) was identified as the only reactive glutamine on the heavy chain of different IgG types to be specifically targeted by MTG with low-molecular weight primary amine substrates (Jeger et al. 2010).

Quantitative conjugation to Q295, however, was only possible upon removal of the glycan moiety at the asparagine residue 297 (N297) with PNGase F, while glycosylated antibodies could not be conjugated efficiently (conjugation efficiency <20%). This finding is also supported by the studies of Mindt et al. (2008) and Jeger et al. (2010) and Dickgiesser et al. 2020

In order to obviate deglycosylation it is also possible to insert a point mutation at the residue N297 which results in the ablation of the glycosylation called aglycosylation.

However, both approaches come with significant disadvantages. An enzymatic deglycosylation step is undesired under GMP aspects, because it has to be made sure that both the deglycosylation enzyme (e.g., PNGase F) as well as the cleaved glycan are removed from the medium, to ensure a high purity product.

The substitution of N297 against another amino acid has unwanted effects, too, because it may affect the overall stability of the $C_H2$ domain, and the efficacy of the entire conjugate as a consequence. Further, the glycan that is present at N297 has important immunomodulatory effects, as it triggers antibody dependent cellular cytotoxicity (ADCC) and the like. These immunomodulatory effects would get lost upon deglycosylation or substitution of N297 against another amino acid.

Furthermore, the genetic engineering of an antibody for payload attachment may have disadvantages in that the sequence insertion may increase immunogenicity and decrease the overall stability of the antibody.

It is hence one object of the present invention to provide a transglutaminase based antibody conjugation approach which does not require prior deglycosylation of the antibody, in particular of N297.

It is another object of the present invention to provide a transglutaminase based antibody conjugation approach which does not require the substitution or modification of N297 in the $C_H2$ domain.

It is one further object of the present invention to provide an antibody conjugation technology that allows the manufacture of highly homogenous conjugation products, both as regards stoichiometry as well as site-specificity of the conjugation.

These and further objects are met with methods and means according to the independent claims of the present invention. The dependent claims are related to specific embodiments.

SUMMARY OF THE INVENTION

The present invention relates to methods and linker structures for generating an antibody-linker conjugate and/or an antibody-payload conjugate by means of a microbial transglutaminase (MTG). The invention and general advantages of its features will be discussed in detail below.

As discussed elsewhere herein, B/star can be or comprise a linking moiety, like e.g. a bio-orthogonal group (e.g., an azide/$N_3$-group) that is suitable for strain-promoted alkyne-azide cycloaddition (SPAAC) click-chemistry reaction to a DBCO-containing payload (e.g. a toxin or a fluorescent dye or a metal chelator, like DOTA or NODA-GA). This click-chemistry-based "two-step chemoenzymatic"-approach to attach the functional moiety to the antibody has the major advantage that it can be clicked at low molecular excess compared to the antibody, typically e.g. at 5 eq per conjugation site or lower (Dennler et al. 2014). This allows for a cost-effective generation of ADCs. In addition, virtually any probe can be clicked with this approach ranging from fluorescent dyes to metal chelators (cf. Spycher et al. 2017, Dennler et al. 2015).

B/star can also be the actual payload, e.g., a toxin. Such embodiment allows the rapid manufacture of the resulting compound in one step, facilitating purification and production.

Figure 1:
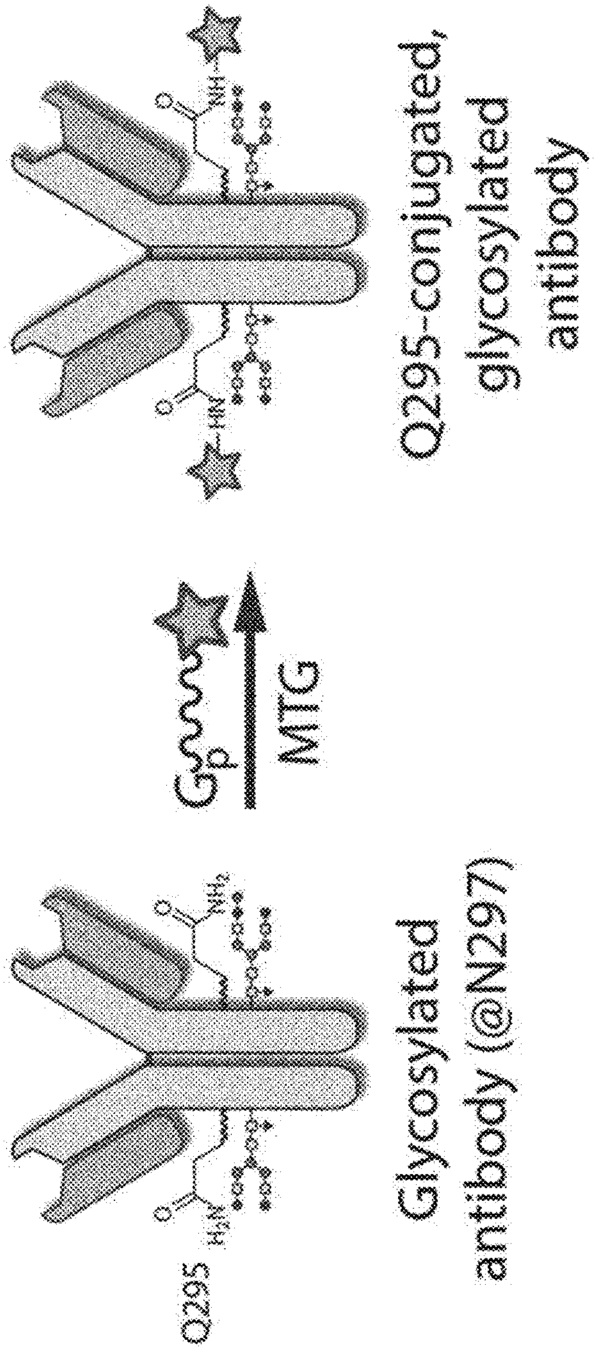
FIG. 1 shows an illustration of one aspect of the present invention. MTG=microbial transglutaminase. The star symbol illustrates the payload or linking moiety B. Gp is a Gly residue, which is N-terminally in a peptide, and which is the substrate for MTG. Note that this process allows to maintain the glycosylation at N297. Note that in case B/star is a linking moiety, the actual payload still has to be conjugated to this moiety.
Figure 2:
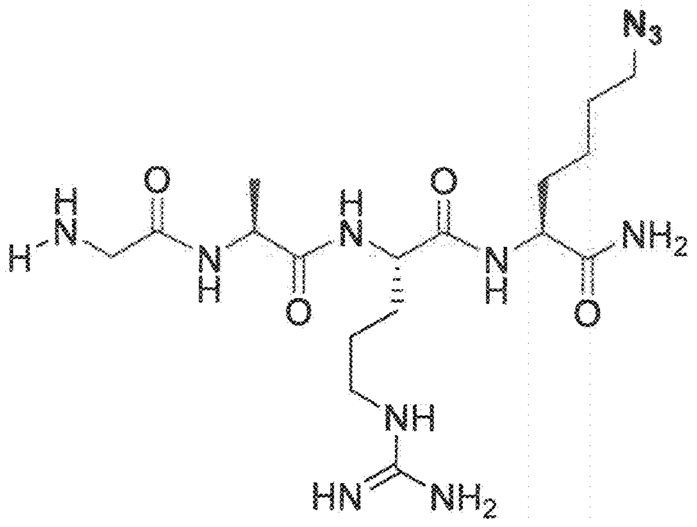

FIG. 2 shows an example of a linker peptide comprising an oligopeptide according to the invention. The sequence is GlyAlaArgLys($N_3$) (GARK$_1$ with $K_1$=Lys($N_3$)). Lys($N_3$) is a Lys residue in which the primary amine has been replaced by an azide group (—N—N≡N, or —$N_3$). According to the nomenclature of the present invention, either Lys($N_3$) or $N_3$ alone can be regarded as the linking moiety B (in this example, $N_3$ is suitable for click-chemistry).

The peptide efficiently conjugates to native IgG1 antibodies (~77.3% as estimated from LC-MS analysis under non-optimized conditions) at position Q295.

It is important to understand that in some linker peptides shown herein, the moiety at the C-terminus is simply designated as $N_3$. However, this should be understood as an abbreviation of Lys($N_3$). For example, GAR($N_3$) corresponds to the peptide GlyAlaArgLys($N_3$) or GARK($N_3$). That is, 6-azido-L-lysine may be abbreviated as Lys($N_3$) in three letter code or as K($N_3$) or ($N_3$) in single letter code. It is thus to be understood that K($N_3$) when part of a peptide always relates to the single amino acid residue Lys($N_3$) but not to the dipeptide Lys-Lys($N_3$). A dipeptide Lys-Lys($N_3$), on the other hand, would be designated KK($N_3$) in single letter code.

It is furthermore important to understand that in different linker peptides shown herein, the C-terminus or primary amines on side chains may or may not be protected, even if shown otherwise. Protection can be accomplished by, e.g., amidation of the former, and/or acetylation of the latter. In the context of the present invention, both the protected and unprotected linker peptides are encompassed.

For example, GARK(N3) does indeed encompass two variants, with the C-terminus protected or unprotected. The following figure shows a C-terminal Lys($N_3$) residue wherein the C-terminus is protected by amidation:

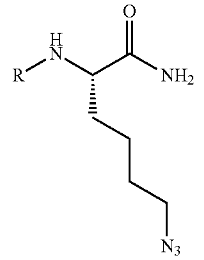

Figure 3:
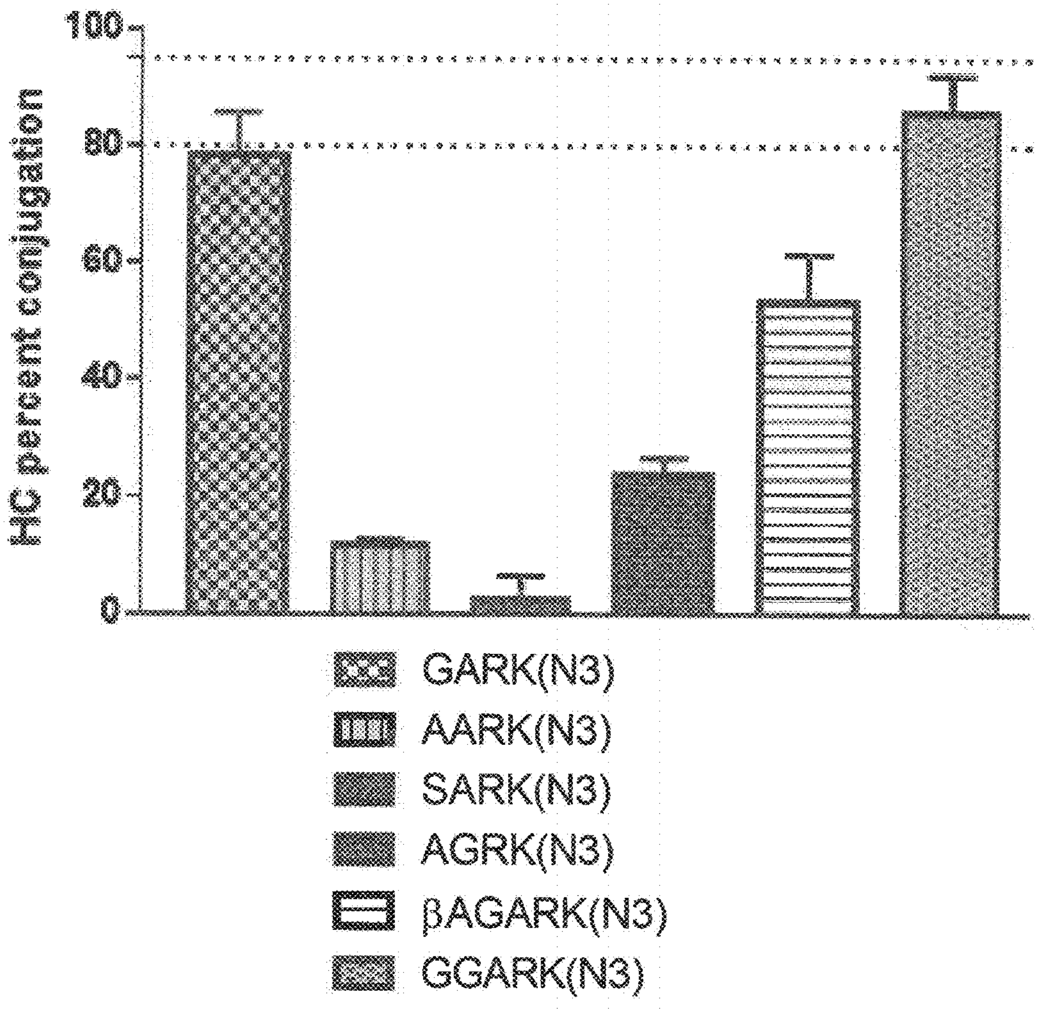

FIG. 3 shows results of the screening of a small given peptide library to native IgG1 antibody. Different peptides were screened that contained MTG-reactive N-terminal amino acid residues or derivatives (beta-alanine). As can be seen, single or double N-terminal glycine works most efficient. LC-MS was used for analysis.

Figure 4:
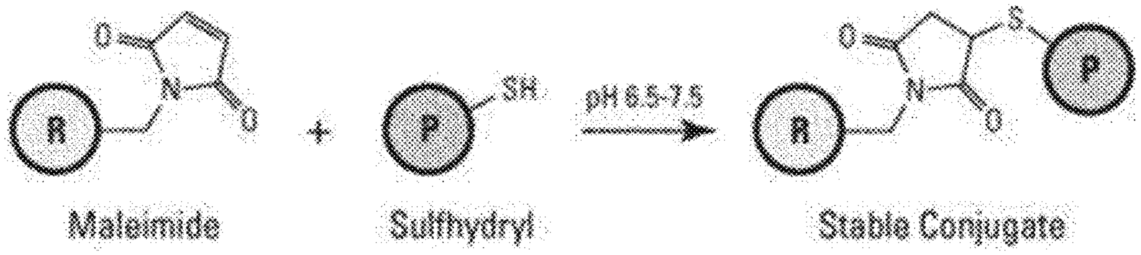

FIGS. 4 and 5 show an embodiment wherein the linker comprises a Cys residue with a free sulfhydryl group, suitable to conjugate a maleimide-comprising toxin linker construct thereto.

FIG. 4 shows the binding reaction, and FIG. 5 some potential linker constructs.

Figure 6A:
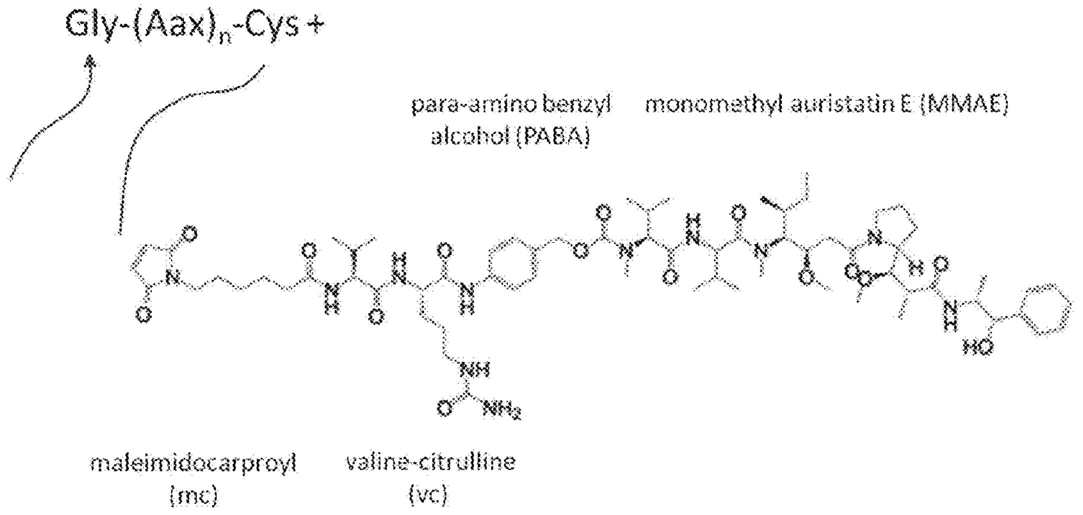
Figure 6B:
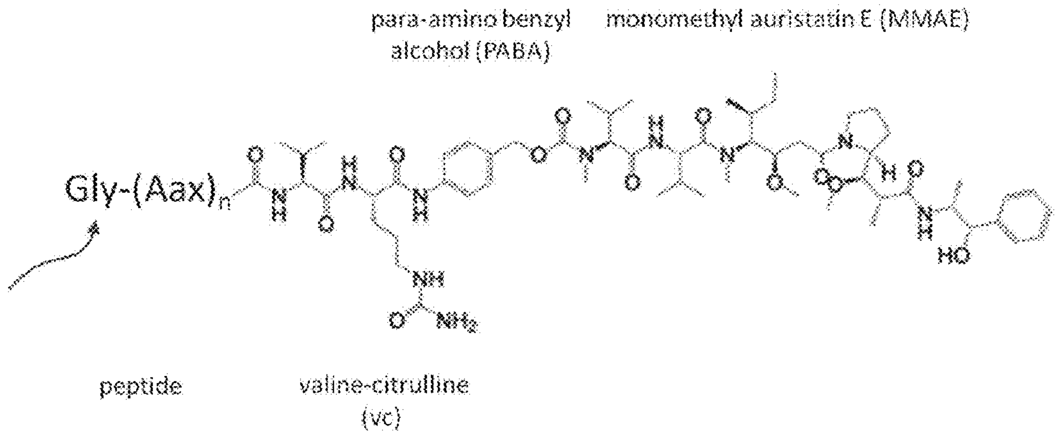

FIGS. 6A-6B show a two-step conjugation process (FIG. 6A) with the peptide being conjugated to the Gln of the antibody (e.g. Q295 of IgG or molecularly engineered) and a one-step conjugation process (FIG. 6B) according to the present invention. The following table 1 clarifies the two terms as used herein:

TABLE 1

| One- and two step conjugation | | |
|---|---|---|
| Linker peptide | Process type | Steps |
| Gly(Aax)$_m$-Payload | One-step conjugation | step 1: conjugation of linker comprising the payload to Gln residue in antibody |
| Gly(Aax)$_n$-Cys-Linking moiety | Two-step conjugation | step 1: conjugation of linker comprising the Cys-Linking moiety to Gln residue in antibody<br>step 2: conjugation of payload to Cys-Linking moiety |

In the two-step process, the linker peptide is Gly-(Aax)$_n$ -Cys-linking moiety. The Gly residue is conjugated to a Gln residue in the antibody via microbial transglutaminase, and the linking moiety—in this case a Cys residue with a free sulfhydryl group—is then conjugated to the payload, in this case a MMAE toxin carrying a MC/VC/PABDC linker structure, via the maleimide.

In the one-step process, the linker peptide Gly-(Aax)$_m$ is already conjugated to the payload. The Gly residue is conjugated to a Gln residue in the antibody, and the payload consists of an MMAE toxin carrying a VC/PABC structure. The valine residue of the VC structure is conjugated to the last amino acid of the linker peptide by means of a peptide bond.

Figure 7A:
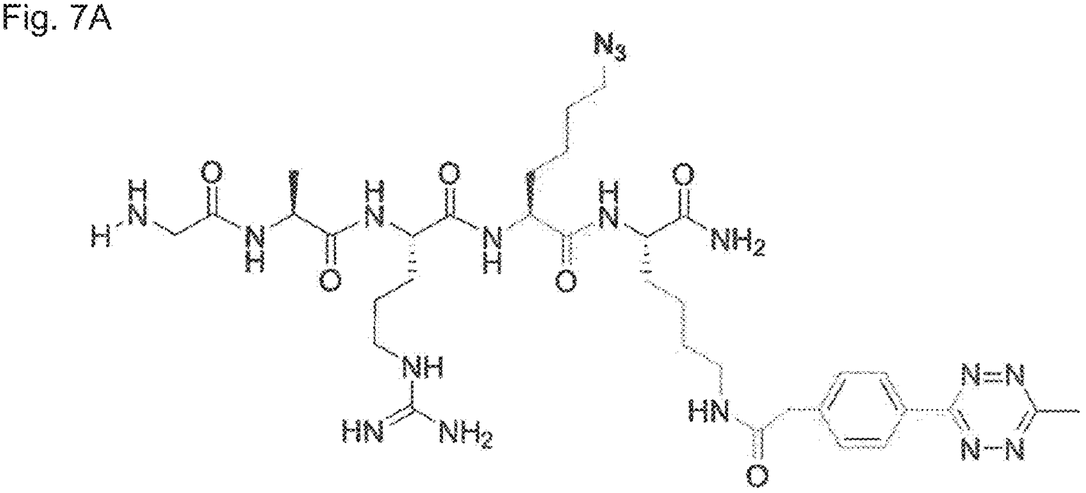
Figure 7B:
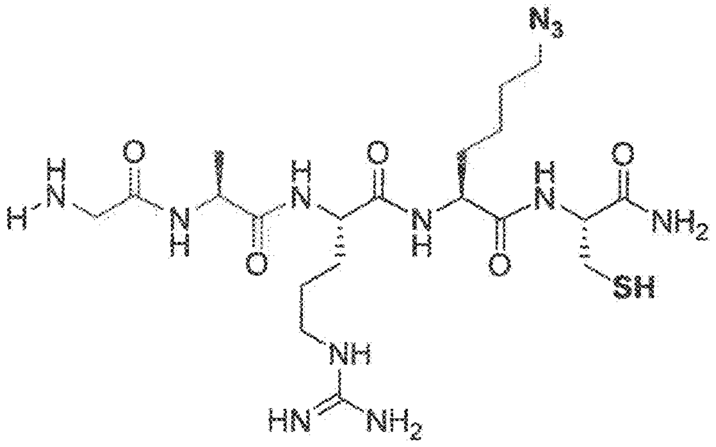

FIGS. 7A-7B show two examples of linkers comprising a linker suitable for dual-payload attachment.

FIG. 7A shows a peptide that has a first linking moiety which is an azide (N3), while a second linking moiety is a tetrazine (both bio-orthogonal). The structure of the oligopeptide is GlyAlaArgLys($N_3$)Lys(Tetrazine) (GARK$_1$K$_2$, with $K_1$=Lys($N_3$), $K_2$=Lys(Tetrazine)).

FIG. 7B shows a peptide carrying an azide ($N_3$) and a free sulfhydryl-group from the Cys-moiety. The structure of the oliogopeptide is GlyAlaArgLys($N_3$)Cys ($GARK_1C$, with $K_1$=Lys($N_3$)).

Each of the linking moieties are bio-orthogonally compatible groups that can be clicked simultaneously.

These linkers thus allow to conjugate two different payloads to the Q295 of the $C_H2$ domain of an antibody. Using a second payload allows for the development of a completely new class of antibody-payload conjugates that go beyond current therapeutic approaches with respect to efficacy and potency. Also new application fields are envisioned, for example, dual-type imaging for imaging and therapy or intra-/postoperative surgery (cf. Azhdarinia A. et al., Molec Imaging and Biology, 2012). For example, dual-labeled antibodies encompassing a molecular imaging agent for preoperative positron emission tomography (PET) and a near-infrared fluorescent (NIRF)-dye for guided delineation of surgical margins could greatly enhance the diagnosis, staging, and resection of cancer (cf. Houghton J L. et al., PNAS 2015). PET and NIRF optical imaging offer complementary clinical applications, enabling the non-invasive whole-body imaging to localize disease and identification of tumor margins during surgery, respectively. However, the generation of such dual-labeled probes up to date has been difficult due to a lack of suitable site-specific methods; attaching two different probes by chemical means results in an almost impossible analysis and reproducibility due to the random conjugation of the probes. Furthermore, in a study of Levengood M. et al., (Angewandte Chemie, 2016) a dual-drug labeled antibody, having attached two different auristatin toxins (having differing physiochemical properties and exerting complementary anti-cancer activities) imparted activity in cell line and xenograft models that were refractory to ADCs comprised of the individual auristatin components. This suggests that dual-labeled ADCs enable to address cancer heterogeneity and resistance more effectively than the single, conventional ADCs alone. Since one resistance mechanism towards ADCs include the active pumping-out of the cytotoxic moiety from the cancer cell, another dual-drug application may include the additional and simultaneous delivery of a drug that specifically blocks the efflux mechanism of the cytotoxic drug. Such a dual-labeled ADC could thus help to overcome cancer resistance to the ADC more effectively than conventional ADCs.

Similar structures in which alkynes or tetrazine/trans-cyclooctenes are being used as linker are equally suitable and covered by the scope and gist of the present invention.

It is important to understand that in some linker peptides shown herein, the moiety at the C-terminus is simply designated as $N_3$. However, this should be understood as an abbreviation of Lys($N_3$). For example, GAR($N_3$) or GARK ($N_3$) does actually mean $GARK_1$, with $K_1$=Lys($N_3$), or GlyAlaArgLys($N_3$).

It is furthermore important to understand that in different linker peptides shown herein, the C-terminus may or may not be protected, even if shown otherwise. Protection may be accomplished by amidation of the C-terminus. Since conjugation of the linker to an antibody is achieved via the primary amine of the N-terminal glycine residue of the linker, the N-terminus of the linker is preferably unprotected. In the context of the present invention, both the protected and unprotected linker peptides are encompassed. For example, GARK($N_3$) does indeed encompass two variants, with a) both termini unprotected as discussed above, or b) only the C-terminus protected as discussed above.

The question whether or not the C-terminus is amidated is a practical question, depending on the conjugation conditions (buffer, medium, reactivity of the other reaction components, etc).

Figure 8A:
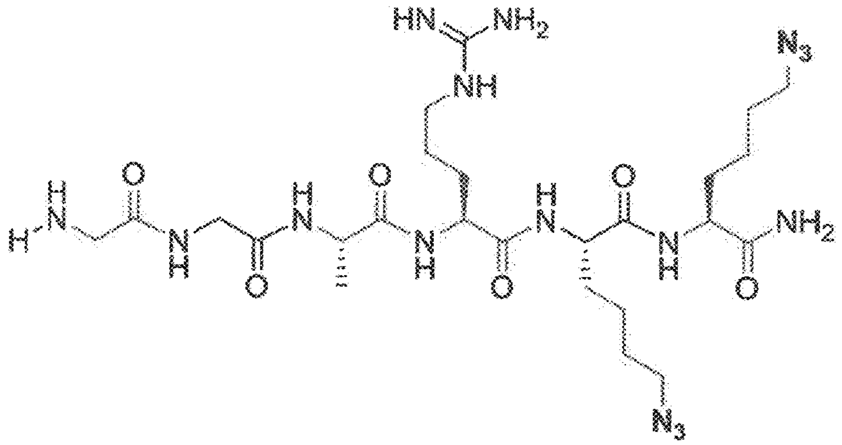
Figure 8B:
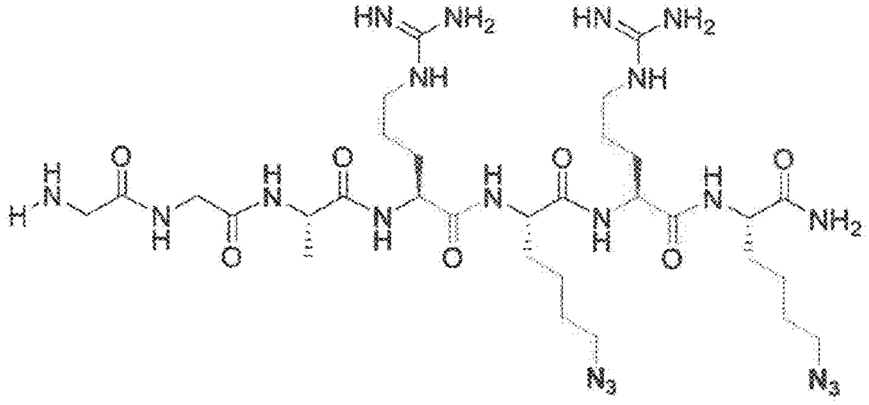

FIGS. 8A and 8B show two possible linker structures with two Azide linker moieties, respectively. FIG. 8A shows GlyGlyAlaArgLys($N_3$)Lys($N_3$) ($GGARK_1K_2$, with $K_1$ and $K_2$=Lys($N_3$)). FIG. 8B shows GlyGlyAlaArgLys($N_3$)ArgLys ($N_3$) ($GGARK_1RK_2$; with $K_1$ and $K_2$=Lys($N_3$)). In such way, an antibody payload ratio of 4 can be obtained. The presence of the charged Arg residues helps to keep hydrophobic payloads in solution.

It is important to understand that in some linker peptides shown herein, the moiety at the C-terminus is simply designated as $N_3$. However, this should be understood as an abbreviation of Lys($N_3$). For example, GAR($N_3$) or GARK ($N_3$) does actually mean $GARK_1$, with $K_1$=Lys($N_3$), or GlyAlaArgLys($N_3$).

FIG. 9 shows further linkers that are suitable for MTG-mediated conjugation to native antibodies. These linker structures contain a linking moiety (azide, $N_3$) suitable for click-chemistry based attachment of the functional payload in a second step, or a Cys-residue which provides a thiol group suitable for attachment to a maleimide. Since these structures are based on peptides, that chemistry is well-understood and which is assembled from building blocks of single amino acids, new linkers can rapidly and easily be synthesized and evaluated. The following table 2 gives an overview:

TABLE 2

| Structure | Sequence, residue for transglutaminase reaction in bold print | | Linking moiety B |
|---|---|---|---|
| 1 | GlyAlaArgLys($N_3$) | $GARK_1$ with $K_1$ = Lys($N_3$) | Lys($N_3$) |
| 2 | GlyAlaArgXaa($N_3$) | GARX, with X = Xaa($N_3$), Xaa is 4-Azido-L-homoalanine | Xaa($N_3$) |
| 3 | GlyAlaArg[PEG]$_3$($N_3$) | GAR[PEG]$_3$$N_3$, with [PEG]$_3$ = triethylenglycol | [PEG]$_3$$N_3$ |
| 4 | GlyAlaArgCys | GARC | Cysteine |
| 5 | GlyGlyAlaArgLys(PEG)$_n$ArgLys($N_3$) | GGAR[PEG]$_n$RK$_1$ with $K_1$ = Lys($N_3$) | Lys($N_3$) |

Figure 10:
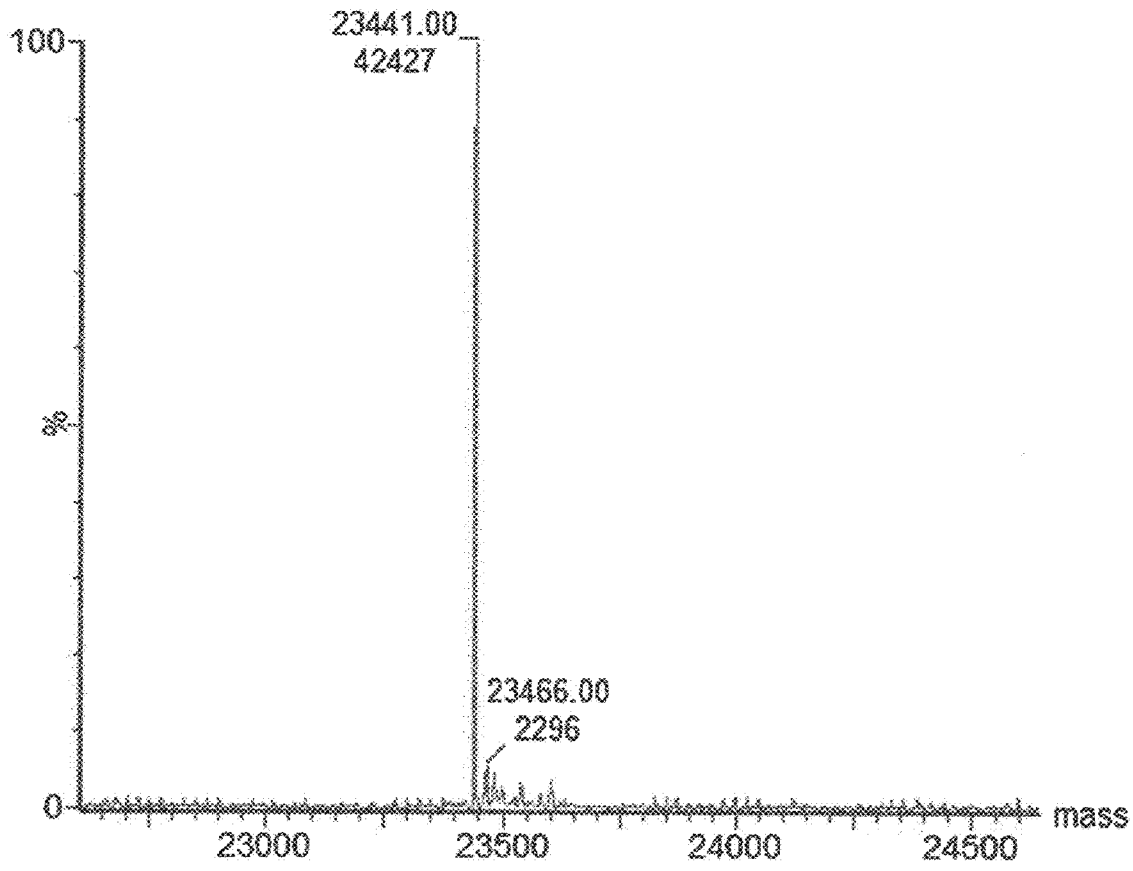

FIG. 10 shows that the light chain of IgG1 antibodies is not modified by the conjugation. Shown is the deconvoluted LC-MS spectra of a IgG1 light chain.

Figure 11A:
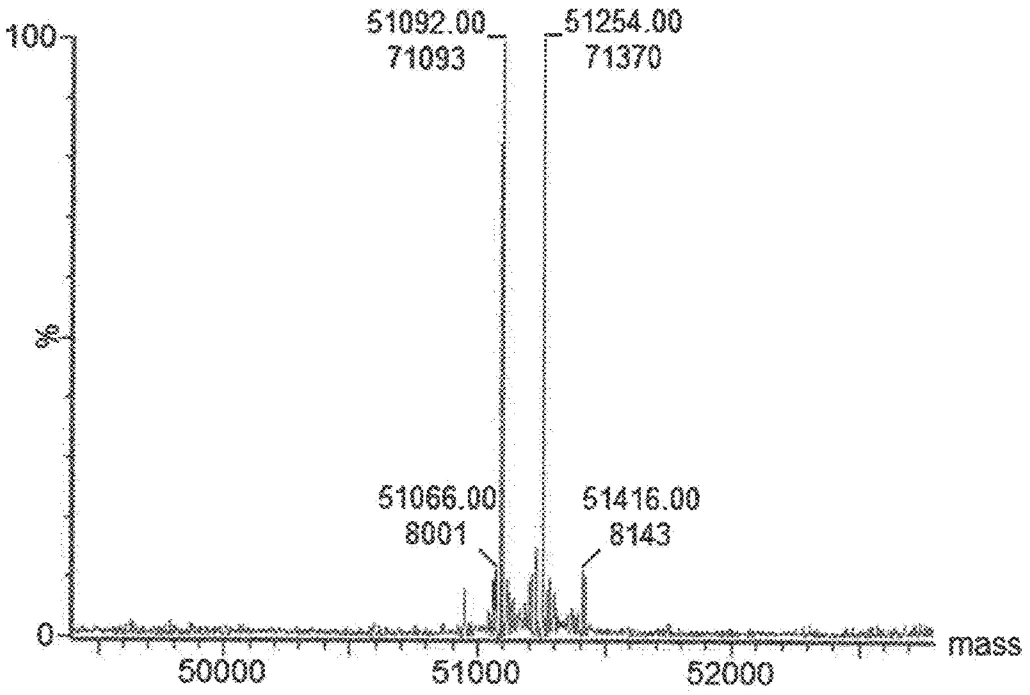

FIG. 11A shows deconvoluted LC-MS spectra of Trastuzumab native IgG1 heavy chain selectively modified with the $N_3$-functional linker GGARK($N_3$). From the spectra it can be seen that the heavy chain got selectively and quantitatively (>95%) modified with only one peptide-linker since the observed mass difference corresponds to the expected peptide mass shift (Mw unmodified heavy chain=50595 Da, expected Mw=51091 Da, measured Mw=51092 Da)

Figure 11B:
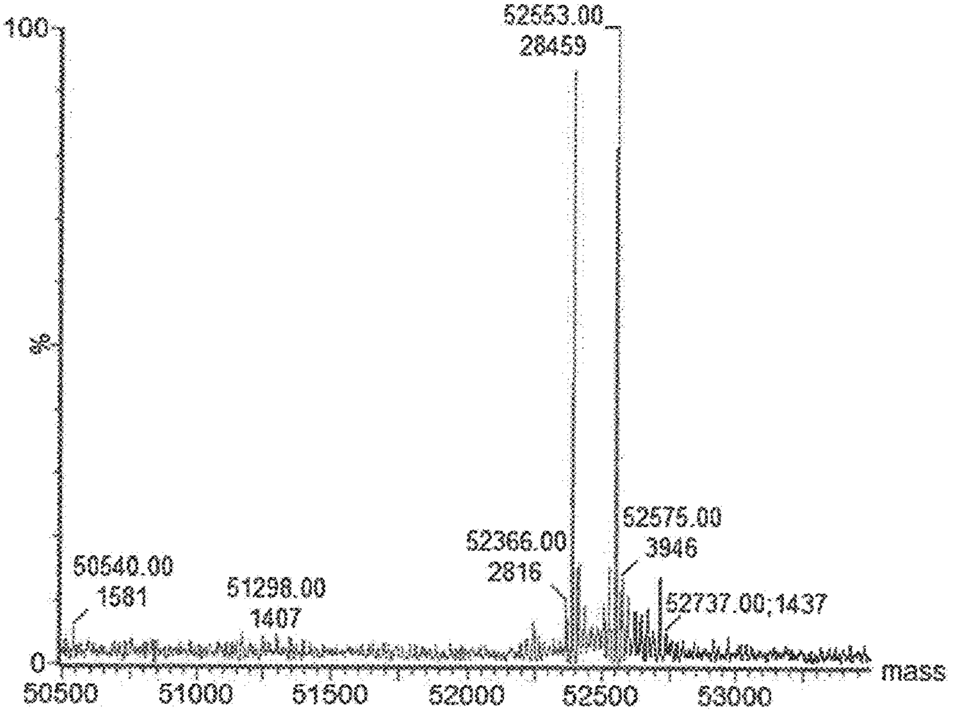

FIG. 11B shows deconvoluted LC-MS spectra of Trastuzumab native IgG1 heavy chain selectively clicked with DBCO-PEG4-Ahx-DM1 to the $N_3$-functional linker GGARK($N_3$) pre-installed on the heavy chain. From the spectra, it can be seen that the heavy chain got selectively and quantitatively (>95%) clicked.

Figure 11C:
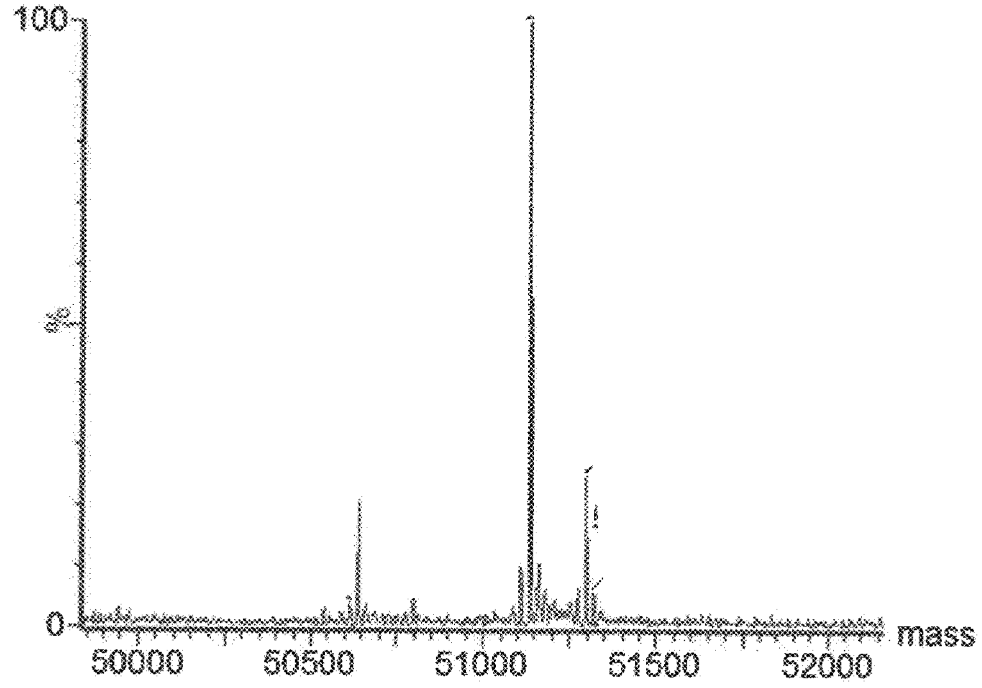

FIG. 11C shows the deconvoluted LC-MS of another IgG1 heavy chain modified with GGARK($N_3$) under non-optimized conjugation conditions. Conjugation ratio: 83%

Figure 12A:
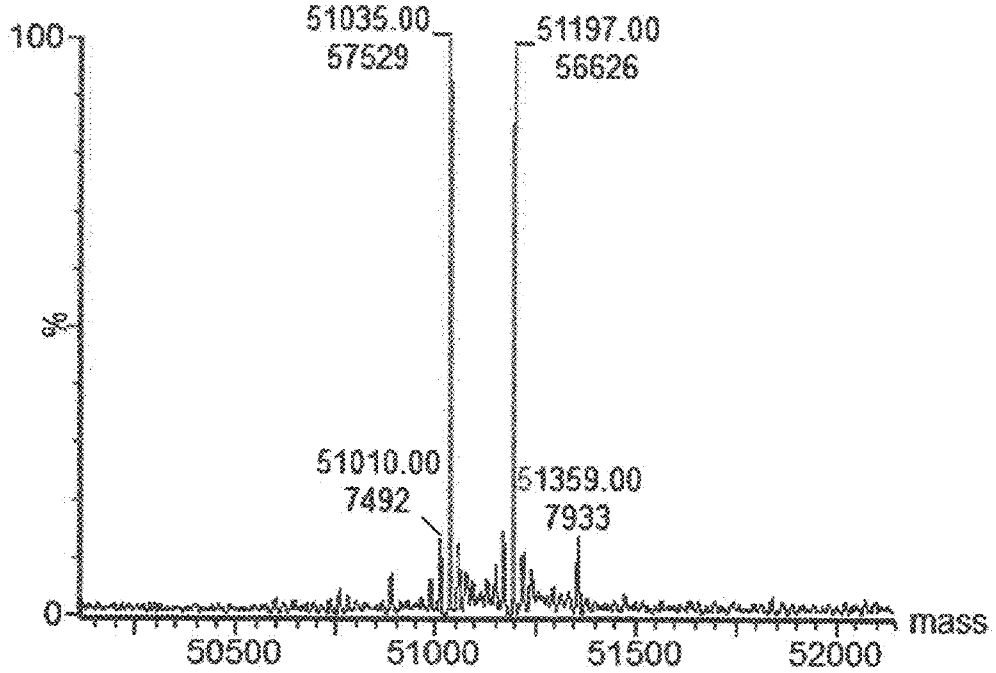

FIG. 12A shows the deconvoluted LC-MS of Trastuzumab heavy chain modified with GARK($N_3$). >95% conjugation efficiency was achieved.

Figure 12B:
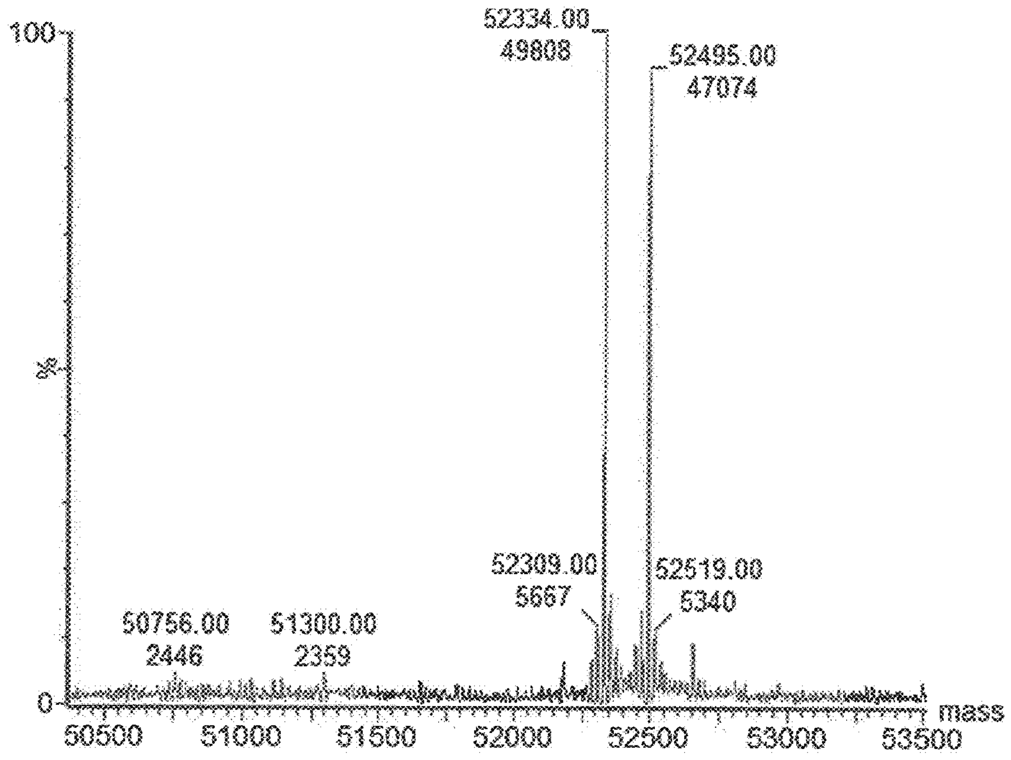

FIG. 12B shows the deconvoluted LC-MS of Trastuzumab heavy chain modified with GARK($N_3$), clicked with DBCO-PEG4-Ahx-DM1>95% clicking efficiency was achieved, resulting in an ADC with DAR 2.

FIG. 13 shows an overview of the Ig $C_H2$ domain with the different numbering schemes. For the purposes of the present invention, the EU numbering is being used.

Figure 14:
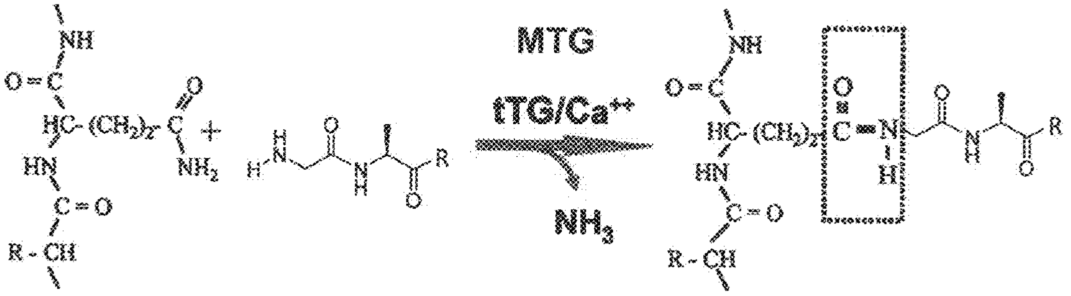

FIG. 14 shows a transglutaminase reaction to conjugate a linker having an N-terminal Gly residue with a free primary amine to the free primary amine of the Q295 residue of an antibody.

Figure 15:
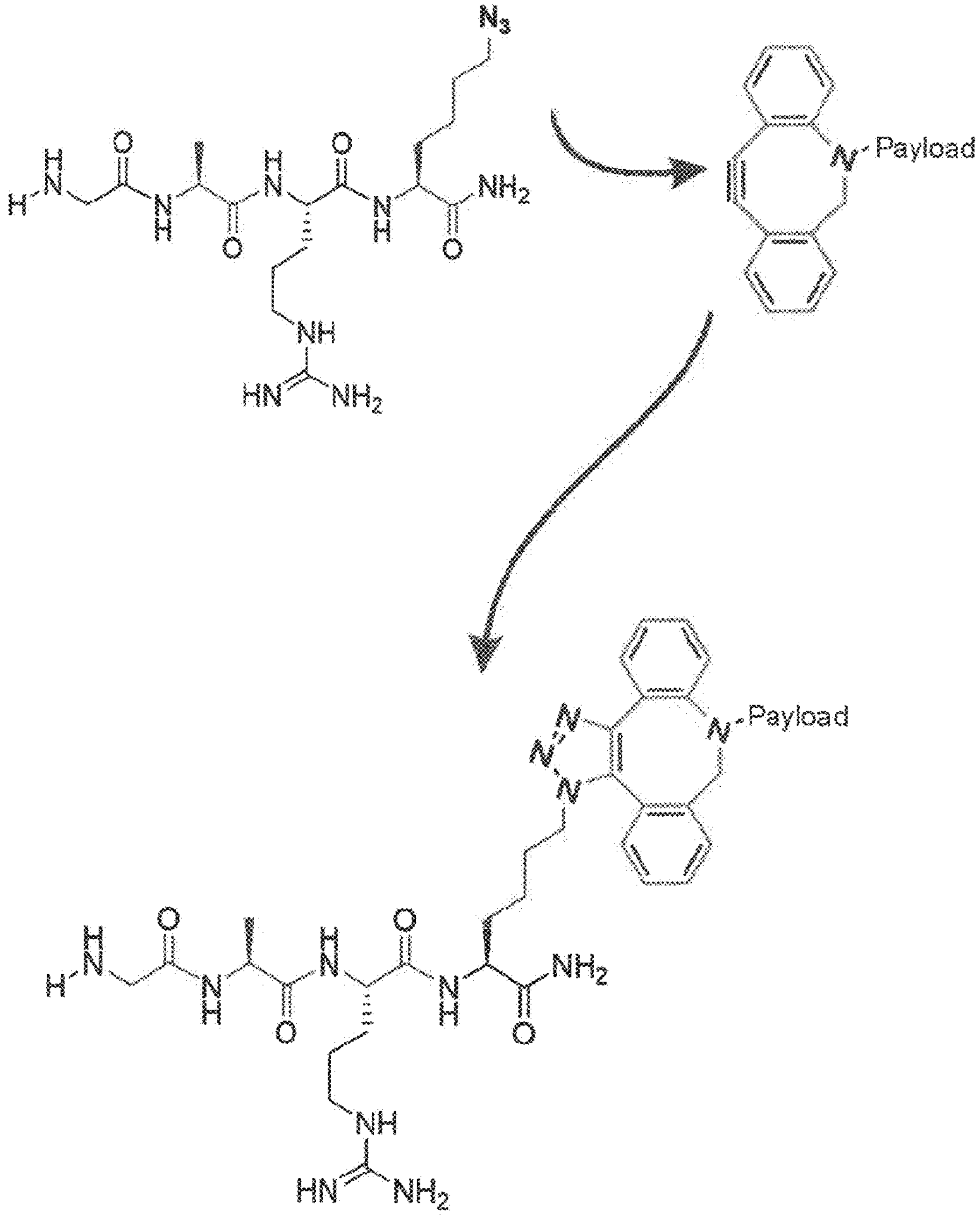

FIG. 15. Click chemistry reaction scheme (strain-promoted alkyne-azide cycloaddition (SPAAC) to conjugate the linker GlyAlaArgLys($N_3$) (GARK$_1$ with K$_1$=Lys($N_3$)) to dibenzocyclooctyne labelled with a payload.

FIG. 16 shows different peptide linkers that can be used in the context of the present invention, comprising a non-natural amino acid each.

FIGS. 17A-17D show different linker toxin constructs that can be conjugated to an antibody according to the method described herein. In all cases, the Gly residues carry the primary amine for transglutaminase conjugation FIG. 17A This Figure shows the non-cleavable GGARR-Ahx-May peptide-toxin conjugate with two arginine-groups serving to increase the solubility of the hydrophobic payload Maytansine (May). The primary amine of the N-terminal glycine residue serves for the conjugation to the antibody via MTG. The Ahx-spacer serves to decouple the positively-charged arginine from the May, helping the latter to more efficiently bind its target since the linker is not cleavable.

Figure 17A:
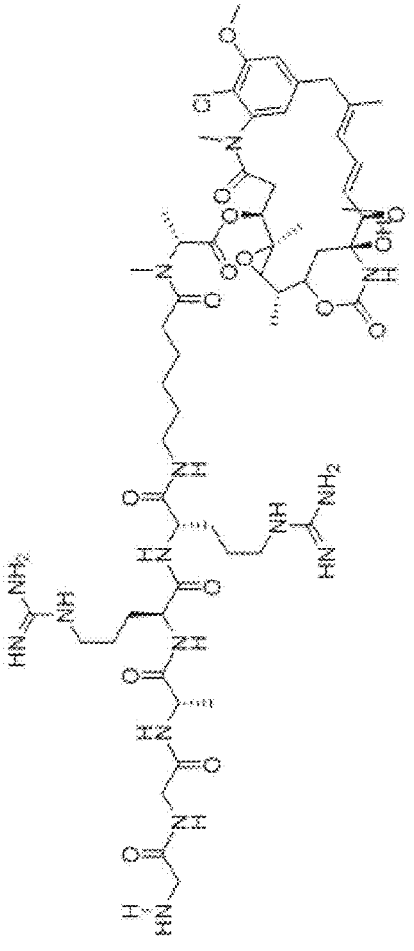
Figure 17B:
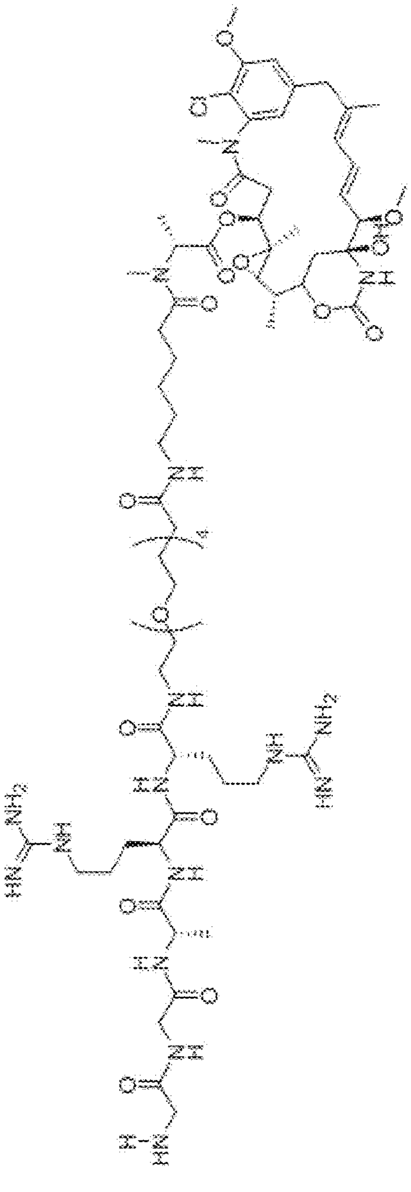

FIG. 17B This Figure shows the non-cleavable GGARR-PEG4-May peptide-toxin conjugate with two arginine-groups and a PEG4-spacer, all three moieties serving to increase the solubility of the hydrophobic payload May. The primary amine of the N-terminal glycine residue serves for the conjugation to the antibody via MTG. The PEG4 furthermore helps to decouple the positively-charged arginine from the May, helping the latter to more efficiently bind its target since the linker is not cleavable.

Figure 17C:
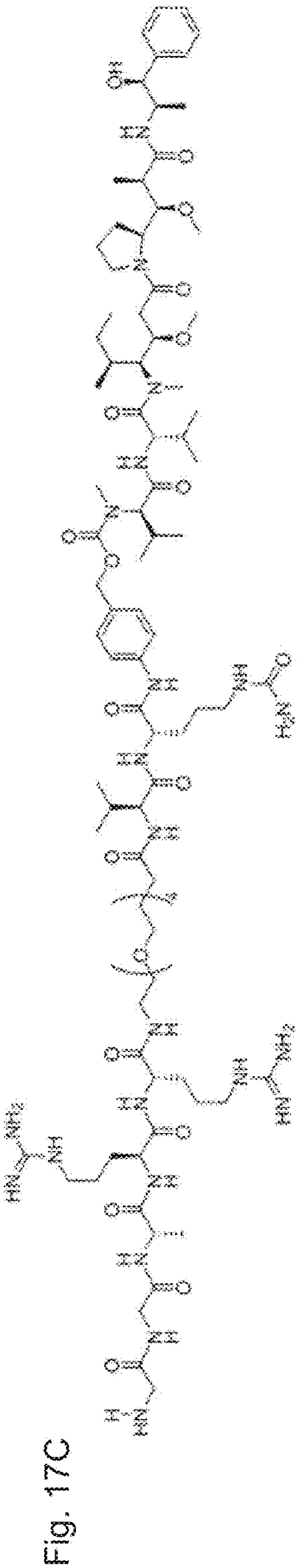

FIG. 17C This Figure shows the cleavable GGARR-PEG4-VC-MMAE peptide-toxin conjugate with two arginine-groups, a PEG4-spacer, a PABC-group and a val-cit sequence (VC). The primary amine of the N-terminal glycine residue serves for the conjugation to the antibody via MTG, the arginine-groups and the PEG4-spacer to increase the solubility and the PABC-group and the val-cit sequence help to release the toxin.

Figure 17D:
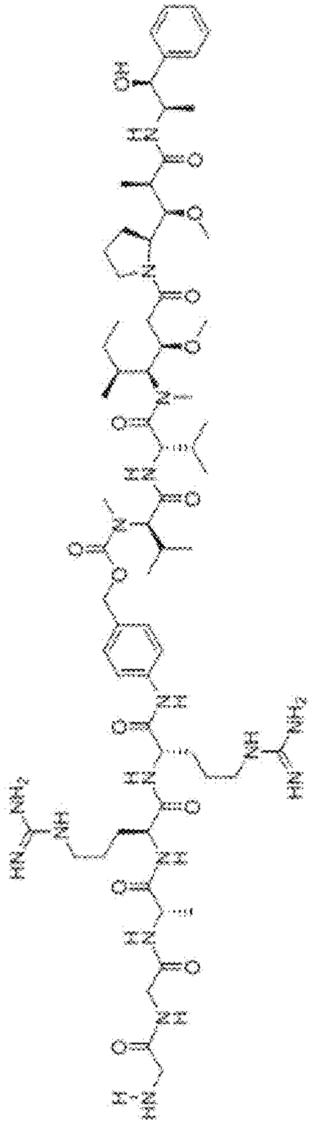

FIG. 17D This Figure shows the cleavable GGARR-MMAE peptide-toxin conjugate with two arginine-groups and a PABC-group with no PEG-spacer and val-cit sequence. Since the GGARR-group is intrinsically degradable by peptidases, no val-cit sequence might be necessary for toxin release through the self-immolative PABC-moiety, and as the two arginine-groups are very hydrophilic no PEG-spacer may be needed, keeping thus the whole peptide-toxin conjugate as small as possible to minimize undesired interactions with other molecules while in blood circulation.

Figure 18:
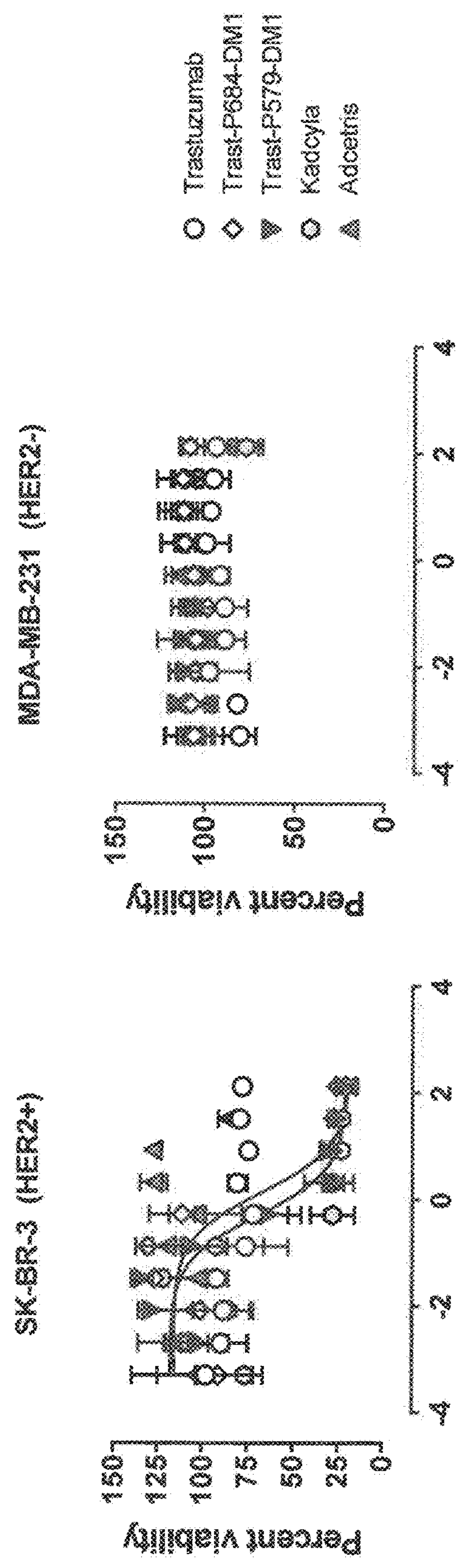

FIG. 18 shows results of a cellular toxicity assay as performed according to example 3. The Her-GARK($N_3$) (P684) and Her-GGARK($N_3$) (P579) N-terminal Glycine ADCs which have been generated with the method according to the invention and comprise a May-moiety click-attached to each linker have similar potency against SK-BR3 cells as Kadcyla. Hence, the advantages provided by the novel linker technology (ease of manufacture, site specificity, stable stoichiometry, no need to deglycosylate that antibody) do not come at any disadvantage regarding the cellular toxicity.

Figure 19:
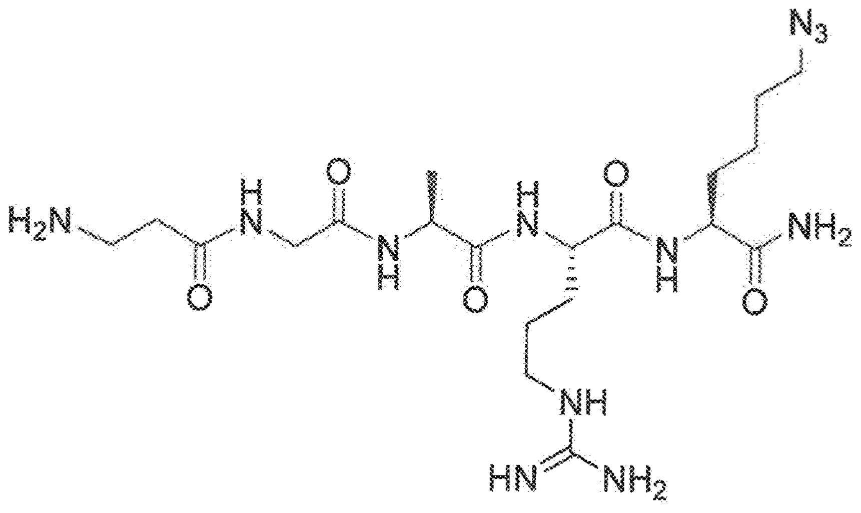

FIG. 19: Structure of βAla-Gly-Ala-Arg-Lys($N_3$). βAla designates β-alanine, which is structurally similar to glycine. However the said linker has inferior conjugation efficiency compared to GGARK($N_3$) (see example 2), which has an N-terminal glycine.

DETAILED DESCRIPTION OF THE INVENTION

Before the invention is described in detail, it is to be understood that this invention is not limited to the particular components or process steps of the methods described as such devices and methods may vary. It is also to be understood that the terminology used herein is for purposes of describing particular embodiments only, and is not intended to be limiting. It must be noted that, as used in the specification and the appended claims, the singular forms “a”, “an”, and “the” include singular and/or plural referents unless the context clearly dictates otherwise. It is moreover to be understood that, in case parameter ranges are given which are delimited by numeric values, the ranges are deemed to include these limitation values.

It is further to be understood that embodiments disclosed herein are not meant to be understood as individual embodiments which would not relate to one another. Features discussed with one embodiment are meant to be disclosed also in connection with other embodiments shown herein. If, in one case, a specific feature is not disclosed with one embodiment, but with another, the skilled person would understand that does not necessarily mean that said feature is not meant to be disclosed with said other embodiment. The skilled person would understand that it is the gist of this application to disclose said feature also for the other embodiment, but that just for purposes of clarity and to keep the specification in a manageable volume this has not been done.

Furthermore, the content of the documents referred to herein is incorporated by reference. This refers, particularly, for documents that disclose standard or routine methods. In that case, the incorporation by reference has mainly the purpose to provide sufficient enabling disclosure, and avoid lengthy repetitions.

According to a first aspect, a method for generating an antibody-payload conjugate or an antibody-linker conjugate by means of a microbial transglutaminase (MTG) is provided, which method comprises the step of conjugating a linker comprising the peptide structure (shown in N->C direction)

$$\text{Gly-(Aax)}_m\text{-B-(Aax)}_n$$

via the N-terminal primary amine of the N-terminal glycine (Gly) residue to a glutamine (Gln) residue comprised in the heavy or light chain of an antibody, wherein m is an integer between ≥0 and ≤12, n is an integer between ≥0 and ≤12, m+n≥0, Aax is an amino acid or an amino acid derivative, and B is a payload or a linking moiety.

As used herein, the term "primary amine" relates to an amine substituted with two hydrogen atoms, of the general formula R—$NH_2$.

In certain embodiments, the peptide linker may comprise two or more linking moieties and/or payloads. That is, the linker may have the peptide structure (shown in N->C direction)

Gly-$(Aax)_m$-B1-$(Aax)_n$-B2-$(Aax)_o$ wherein m, n and o are integers between ≥0 and ≤12, m+n+o≥0, Aax is an amino acid or an amino acid derivative, and $B_1$ and $B_2$ are payloads and/or linking moieties, wherein $B_1$ and $B_2$ may be identical or different from each other.

In other embodiments, the peptide linker may comprise three linking moieties and/or payloads. That is, the linker may have the peptide structure (shown in N->C direction)

Gly-$(Aax)_m$-$B_1$-$(Aax)_n$-$B_2$-$(Aax)_o$-$B_3$-$(Aax)_p$ wherein m, n, o and p are integers between ≥0 and ≤12, m+n+o+p≥0, Aax is an amino acid or an amino acid derivative, and $B_1$, $B_2$ and $B_3$ are payloads and/or linking moieties, wherein $B_1$, $B_2$ and $B_3$ may be identical or different from each other.

It is to be understood, that the invention also encompasses linkers comprising more than three linking moieties and/or payloads, such as 4, 5 or 6 linking moieties and/or payloads. In this case, the peptide structure of the linkers follows the same pattern as described above for the linkers comprising 2 or 3 linking moieties and/or payloads.

In certain embodiments, a method for generating an antibody-payload conjugate by means of a microbial transglutaminase (MTG) is provided, which method comprises the step of conjugating a linker having the peptide structure (shown in N->C direction)

Gly-$(Aax)_m$-B-$(Aax)_n$ via the N-terminal primary amine of the N-terminal glycine (Gly) residue to a glutamine (Gln) residue comprised in the heavy or light chain of an antibody, wherein m is an integer between ≥0 and ≤12 n is an integer between ≥0 and ≤12 m+n≥0,

Aax can be any naturally or non-naturally occurring L- or D-amino acid, or amino acid derivative or mimetic, and B is a payload or a linking moiety.

In certain embodiments, the invention relates to a method for generating an antibody-payload conjugate or an antibody-linker conjugate by means of a microbial transglutaminase (MTG), which method comprises the step of conjugating a linker having the peptide structure (shown in N->C direction)

Gly-$(Aax)_m$-B-$(Aax)_n$ via the N-terminal primary amine of the N-terminal glycine (Gly) residue to a glutamine (GM) residue comprised in the heavy or light chain of an antibody. In this case, it is to be understood that the moiety B may comprise more than one payload and/or linking moiety. For example, B may stand for (B'-$(Aax)_o$-B"), wherein B' and B" are payloads and/or linking moieties and wherein o is an integer between ≥0 and ≤12. Alternatively, B may stand for (B'-$(Aax)_o$-B"-$(Aax)_p$-B'"), wherein B', B" and B'" are payloads and/or linking moieties and wherein o and p are integers between ≥0 and ≤12.

Thus, in a particular embodiment, the invention relates to a method according to the invention, wherein the linker comprises two or more payloads and/or linking moieties. In another embodiment, the invention relates to a method according to the invention, wherein the two or more payloads and/or linking moieties B differ from one another.

That is, the linker according to the invention may comprise a single payload or linking moiety. In certain embodiments, the linker comprises two linking moieties, wherein the two linking moieties are identical. In other embodiments, the linker comprises two linking moieties, wherein the two linking moieties are different. In yet another embodiment, the linker comprises two identical or different payloads. The invention further encompasses linkers comprising one or more payload and one or more linking moiety.

It is further to be understood that not all payloads or linking moieties can function as an intrachain payload or linking moiety, for example, because they do not have the functional groups to form peptide or amide bonds with the C-terminal carboxyl group of a first Aax moiety and the N-terminal amine group of a second Aax moiety. In this case, it is preferred that such payload or linking moieties are located at the C-terminal end of the linker, where they preferably are attached to the carboxyl group of the C-terminal Aax moiety of the linker. In cases where the payload or linking moiety are at an intrachain position of the linker, it is preferred that the payload or linking moiety is an amino acid, an amino acid derivative or attached to a molecule having the general structure —NH—CHR—CO—.

In preferred embodiments, m and/or n is ≥1, ≥2, ≥3, ≥4, ≥5, ≥6, ≥7, ≥8, ≥9, ≥10, or ≥11. In other preferred embodiments, m and/or n is ≤12, ≤11, ≤10, ≤9, ≤8, ≤7, ≤6, ≤5, ≤4, ≤3, ≤2, or ≤1. In further preferred embodiments, m+n is ≥1, ≥2, ≥3, ≥4, ≥5, ≥6, ≥7, ≥8, ≥9, ≥10, or ≥11. In still further preferred embodiments m+n is ≤12, ≤11, ≤10, ≤9, ≤8, ≤7, ≤6, ≤5, ≤4, ≤3, ≤2, or ≤1.

Members of both ranges can be combined with another to disclose a preferred length range with lower and upper limit.

Accordingly, in a particular embodiment, the invention relates to a method according to the invention, wherein m+n, and optionally m+n+o and m+n+o+p, is ≤12, ≤11, ≤10, ≤9, ≤8, ≤7, ≤6, ≤5 or ≤4.

It is important to understand that in different linker peptides shown herein, the C-terminus may or may not be protected, even if shown otherwise. Protection can be accomplished by amidation of the former. In the context of the present invention, both the protected and unprotected linker peptides are encompassed.

The inventors have shown that this process is suitable to very cost effectively and quickly produce site-specific antibody-payload conjugates (24-36 hrs, or optionally 48 hrs), and hence allows the production of large libraries of such molecules, and subsequent screening thereof in high throughput screening systems.

In contrast thereto, a Cys engineering process in which an antibody payload conjugate is produced where the payload is conjugated to the antibody via a genetically (molecularly) engineered Cys residue needs at least about 3-4 weeks.

In general, the method allows conjugation of a large number of payloads to an antibody. For each payload, a suitable peptide linker structure can be identified from a large linker pool to deliver optimal clinical and non-clinical characteristics. This is not possible in other methods where the linker structure is fixed. In addition, the method according to the invention allows to generate antibody-payload conjugates comprising two or more different payloads, wherein each payload is conjugated to the antibody in a site-specific manner. Thus, the method according to the invention may be used to generate antibodies with novel and/or superior therapeutic or diagnostic capacities.

The linker may comprise any amino acid, including, without limitation, α-, β-, γ-, δ- and ε-amino acids. In the case of α-amino acids, the linker may comprise any naturally occurring L- or D-amino acid. A naturally occurring L- or D-amino acid encompasses any L- or D-amino acid that can be found in nature. That is, the term "naturally occurring L- or D-amino" acid encompasses all canonical or proteogenic amino acids that are used as building blocks in naturally-occurring proteins. In addition, the term "naturally occurring L- or D-amino" acid encompasses all non-canonical L- or D-amino acids that can be found in nature, for example as metabolic intermediates or degradation products or as building blocks for other non-proteogenic macromolecules.

Further, the linker may comprise non-naturally occurring L- or D-amino acids. A non-naturally occurring L- or D-amino acid encompasses any molecule having the general structure $H_2N—CHR—COOH$, which has not previously been found in nature.

The skilled person is aware of resources and databases to consult when determining whether an L- or D-amino acid is naturally or non-naturally occurring. However, in cases of doubt, it is to be understood that the term "naturally or non-naturally occurring L- or D-amino acid" encompasses the L- and D-isomer of any molecule having the general structure $H_2N—CHR—COOH$, irrespective of the origin of said molecule.

In certain embodiments, the linker of the invention may also comprise naturally or non-naturally occurring, non-chiral amino acids having the general structure $H_2N—CR_1R_2—COOH$.

Furthermore, the linker of the invention may comprise amino acid derivatives. An amino acid derivative is a compound that has been derived from a naturally or non-naturally occurring amino acid by one or more chemical reactions, such as chemical reactions of the α-amino group, the α-carboxylic acid group and/or the amino acid side chain. That is, the term amino acid derivative encompasses any molecule having the structure —NH—CHR—CO—, which has been derived from a naturally or non-naturally occurring L- or D-amino acid. Since it is envisioned that the amino acid derivative of the invention is part of a peptide-based linker, it is preferred that the amino acid derivative has been obtained by one or more chemical reactions of the amino acid side chain of a naturally or non-naturally occurring L- or D-amino acid, or, in cases where the amino acid derivative is located at the C-terminal end of the peptide, the alpha-carboxylic acid group of a naturally or non-naturally occurring L- or D-amino acid. It is to be noted that naturally and non-naturally occurring amino acids can be amino acid derivatives and vice versa.

Examples of non-canonical amino acids, non-naturally occurring amino acids and amino acid derivatives that may be comprised in the linker of the invention include, but are not limited to, α-aminobutyric acid, α-aminoisobutyric acid, ornithine, hydroxyproline, agmatine, {S)-2-amino-4-((2-amino)pyrimidinyl)butanoic acid, alpha-aminoisobutyric acid, p-benzoyl-L-phenylalanine, t-butylglycine, citruiline, cyclohexylalanine, desamino tyrosine, L-(4-guanidino)phenylalanine, homoarginine, homocysteine, homoserine, homolysine, n-formyl tryptophan, norleucine, norvaline, phenylglycine, (S)-4-piperidyl-(N-amidino)glycine, para-benzoyl-L-phenylalanine, sarcosine and 2-thienyl alanine.

Besides alpha-amino acids as described above, the linker of the invention may also comprise one or more β-, γ-, δ- or ε-amino acids. Thus, in certain embodiments, the linker may be a peptidomimetic. The peptidomimetic may not exclusively contain classical peptide bonds that are formed between two α-amino acids but may additionally or instead comprise one or more amide bonds that are formed between an alpha amino acid and a β-, γ-, δ- or ε-amino acid, or between two β-, γ-, δ- or ε-amino acids. An example of a linker that is a peptidomimetic and comprises an amide bond between an α-amino acid and a β-amino acid is shown in FIG. 16 (Gly-β-Ala-Arg-Lys($N_3$)). Accordingly, in any instance of the present invention where the linker is described as a peptide, it is to be understood that the linker may also be a peptidomimetic and thus not exclusively consist of α-amino acids, but may instead comprise one or more β-, γ-, δ- or ε-amino acids or molecules that are not classified as an amino acid. Examples of β-, γ-, δ- or ε-amino acids that may be comprised in the linker of the present invention include, but are not limited to, β-alanine, γ-aminobutyric acid, 4-amino-3-hydroxy-5-phenylpentanoic acid, 4-amino-3-hydroxy-6-methylheptanoic acid, 6-aminohexanoic acid and statine.

The term "D-amino acid" is understood to comprise the D-counterparts of both naturally occurring amino acids as well as of non-naturally occurring amino acids.

Since the peptide linkers of the present invention are peptide-based, they are likely to be hydrolyzed by a host cell peptidase once the antibody-payload conjugate has been internalized into a target cell. Accordingly, in certain embodiments, the linker does not necessarily need to comprise a cathepsin cleavage site. Thus, in one embodiment, the linker comprising or having the peptide structure is not cleavable by cathepsin. This includes, in particular, cathepsin B. In one further embodiment, the linker comprising or having the peptide structure does not comprise a valine-alanine motif or a valine-citrulline motif. However, it is to be understood that the invention also encompasses linkers that comprise a cathepsin cleavage site, such as valine-alanine or valine-citrulline. For example, linkers comprising non-canonical or D-amino acids may not be cleaved efficiently by host cell peptidases. In this case, a cathepsin cleavage site in the linker may improve the release of the payload after internalization into the host cell. The linker may further comprise other motifs or self-immolative groups that allow efficient release of the payload inside a target cell if required.

One typical dipeptide structure used in ADC linkers, yet devoid of a Lys residue, is the valine-citrulline motif, as e.g. provided in Brentuximab Vedotin, and discussed in Dubowchik and Firestone 2002. This linker can be cleaved by cathepsin B to release the toxin at the site of disease. The same applies to the valine-alanine motif, which is for example provided in SGN-CD33A.

In one further embodiment, the linker does not comprise polyethylene glycol or a polyethylene glycol derivative.

Polyethylene glycol (PEG) is a polyether compound with many applications from industrial manufacturing to medicine. PEG is also known as polyethylene oxide (PEO) or polyoxyethylene (POE), depending on its molecular weight.

The structure of PEG is commonly expressed as H—(O—$CH_2$—$CH_2$)$_n$—OH. However, it is to be understood that the linkers of the invention may comprise PEG or a PEG-derivative.

It is hence important to understand that, because B can either be a payload or a linking moiety, the method according to the invention has two major embodiments, as shown in the following table 3:

TABLE 3

| Linker peptide | Process type | Steps |
|---|---|---|
| Gly-(Aax)$_m$-Payload-(Aax)$_n$ | One-step conjugation | step 1: conjugation of linker comprising the payload to Gln residue in antibody |
| Gly-(Aax)$_m$-linking moiety-(Aax)$_n$ | Two-step conjugation | step 1: conjugation of linker comprising the linking moiety to Gln residue in antibody<br>step 2: conjugation of payload to Linking moiety |

That is, in certain embodiments, the payload is coupled to the linker by chemical synthesis. Accordingly, the linker may have the structure Gly-(Aax)$_m$-Payload or Gly-(Aax)$_m$-Payload-(Aax)$_n$. For example, the payload may be coupled to the C-terminus of a peptide by chemical synthesis. Thus, in certain embodiments the linker may have the structure Gly-Ala-Arg-Payload, Gly-Ala-Arg-Arg-Payload, Gly-Gly-Ala-Arg-Payload, Gly-Gly-Ala-Arg-Arg-Payload or Gly-Gly-Gly-Payload.

According to one further embodiment of the invention, the antibody is at least one selected from the group consisting of IgG, IgE, IgM, IgD, IgA and IgY IgG1, IgG2, IgG3, IgG4, IgA1 and IgA, and/or a fragment or recombinant variant thereof retaining target binding properties and comprising the $C_H2$ domain The antibody is preferably a monoclonal antibody.

The antibody can be of human origin, but likewise from mouse, rat, goat, donkey, hamster, or rabbit. In case the conjugate is for therapy, a murine or rabbit antibody can optionally be chimerized or humanized.

Fragment or recombinant variants of antibodies comprising the $C_H2$ domain are, for example, antibody formats comprising mere heavy chain domains (shark antibodies/IgNAR ($V_H$-$C_H$1-$C_H$2-$C_H$3-$C_H$4-$C_H$5)$_2$ or camelid antibodies/hcIgG ($V_H$-$C_H$2-$C_H$3)$_2$)

scFv-Fc (VH-VL-CH2-CH3)2

Fc fusion peptides, comprising an Fc domain and one or more receptor domains.

The antibody can also be bispecific (e.g., DVD-IgG, crossMab, appended IgG-HC fusion) or biparatopic. See Brinkmann and Kontermann (2017) for an overview.

Accordingly, in a particular embodiment, the invention relates to the method according to the invention, wherein the antibody is an IgG, IgE, IgM, IgD, IgA or IgY antibody, or a fragment or recombinant variant thereof, wherein the fragment or recombinant variant thereof retains target binding properties and comprises a $C_H2$ domain.

In a preferred embodiment, the antibody is an IgG antibody. That is, the antibody may be an IgG antibody that is glycosylated, preferably at residue N297. Alternatively, the antibody may be a deglycosylated antibody, preferably wherein the glycan at residue N297 has been cleaved off with the enzyme PNGase F. Further, the antibody may be an aglycosylated antibody, preferably wherein residue N297 has been replaced with a non-asparagine residue. Methods for deglycosylating antibodies and for generating aglycosylated antibodies are known in the art.

As discussed herein, IgG antibodies that are glycosylated at residue N297 have several advantages over non-glycosylated antibodies. In addition, it has been demonstrated that the linkers of the invention can be conjugated to antibodies that are glycosylated at residue N297 with unexpectedly high efficiency. Accordingly, in an even more preferred embodiment, the antibody is an IgG antibody that is glycosylated at residue N297 (EU numbering) of the $C_H2$ domain.

In a particular embodiment, the invention relates to the method according to the invention, wherein (a) the linker including the payload or linking moiety B is conjugated to a Gln residue which has been introduced into the heavy or light chain of the antibody by molecular engineering or (b) the linker including the payload or linking moiety B is conjugated to a Gln residue in the Fc domain of the antibody.

According to one further embodiment of the invention, the payload or linking moiety is conjugated to a Gln residue which was introduced into the heavy or light chain of the antibody by molecular engineering.

The term "molecular engineering," as used herein, refers to the use of molecular biology methods to manipulate nucleic acid sequences. Within the present invention, molecular engineering may be used to introduce Gln residues into the heavy or light chain of an antibody. In general, two different strategies to introduce Gln residues into the heavy or light chain of an antibody are envisioned within the present invention. First, single residues of the heavy or light chain of an antibody may be substituted with a Gln residue. Second, Gln-containing peptide tags consisting of two or more amino acid residues may be integrated into the heavy or light chain of an antibody. For that, the peptide tag may either be integrated into an internal position of the heavy or light chain, that is, between two existing amino acid residues of the heavy or light chain or by replacing them, or the peptide tag may be fused (appended) to the N- or C-terminal end of the heavy or light chain of the antibody.

In the first case, any amino residue of the heavy or light chain of an antibody may be substituted with a Gln residue, provided that the resulting antibody can be conjugated with the linkers of the invention by a microbial transglutaminase. In certain embodiments, the antibody is an antibody wherein amino acid residue N297 (EU numbering) of the $C_H2$ domain of an IgG antibody is substituted, in particular wherein the substitution is an N297Q substitution. Antibodies comprising an N297Q mutation may be conjugated to more than one linker per heavy chain of the antibody. For example, antibodies comprising an N297Q mutation may be conjugated to four linkers, wherein a one linker is conjugated to residue Q295 of the first heavy chain of the antibody, one linker is conjugated to residue N297Q of the first heavy chain of the antibody, one linker is conjugated to residue Q295 of the second heavy chain of the antibody and one linker is conjugated to residue N297Q of the second heavy chain of the antibody. The skilled person is aware that replacement of residue N297 of an IgG antibody with a Gln residue results in an aglycosylated antibody.

In a particular embodiment, the invention relates to the method according to the invention, wherein the Gln residue that has been introduced into the heavy or light chain of the antibody by molecular engineering is comprised in a peptide that has been (a) integrated into the heavy or light chain of the antibody or (b) fused to the N- or C-terminal end of the heavy or light chain of the antibody.

Thus, instead of substituting single amino acid residues of an antibody, peptide tags comprising a Gin residue that is accessible for a transglutaminase may be introduced into the heavy or light chain of the antibody. Such peptide tags may be fused to the N- or C-terminus of the heavy or light chain of the antibody. Preferably, peptide tags comprising a transglutaminase-accessible Gln residue are based to the C-terminus of the heavy chain of the antibody. Even more preferably, the peptide tags comprising a transglutaminase-accessible Gin residue are fused to the C-terminus of the heavy chain of an IgG antibody. Several peptide tags that may be fused to the C-terminus of the heavy chain of an antibody and serve as substrate for a microbial transglutaminase are described in WO 2012/059882, WO 2016/144608, WO 2016/100735, WO 2016/096785 and by Steffen et al. (JBC, 2017) and Malesevic et al. (Chembiochem, 2015).

Exemplary peptide linkers that may be introduced into the heavy or light chain of an antibody, in particular fused to the C-terminus of the heavy chain of the antibody, are LLQGG, LLQG, LSLSQG, GGGLLQGG, GLLQG, LLQ, GSPLAQSHGG, GLLQGGG, GLLQGG, GLLQ, LLQLLQGA, LLQGA, LLQYQGA, LLQGSG, LLQYQG, LLQLLQG, SLLQG, LLQLQ, LLQLLQ, LLQGR, EEQYASTY, EEQYQSTY, EEQYNSTY, EEQYQS, EEQYQST, EQYQSTY, QYQS, QYQSTY, YRYRQ, DYALQ, FGLQRPY, EQKLISEEDL, LQR and YQR.

The skilled person is aware of methods to substitute amino acid residues of antibodies or to introduce peptide tags into antibodies, for example by methods of molecular cloning as described in Sambrook, Joseph. (2001). Molecular cloning: a laboratory manual. Cold Spring Harbor, N.Y. Cold Spring Harbor Laboratory Press.

According to one further embodiment of the invention, the payload or linking moiety is conjugated to a Gln in the Fc domain of the antibody.

That is, the linkers of the invention may be conjugated to any Gln residue in the Fc domain of the antibody that can serve as a substrate for a microbial transglutaminase.

Typically, the term Fc domain as used herein refers to the last two constant region immunoglobulin domains of IgA, IgD and IgG ($C_H2$ and $C_H3$) and the last three constant region domains of IgE, IgY and IgM ($C_H2$, $C_H3$ and $C_H4$). That is, the linker comprising the payload or linking moiety B may be conjugated to the $C_H2$, $C_H3$ and, where applicable, $C_H4$ domains of the antibody.

According to one further embodiment of the invention, the payload or linking moiety is conjugated to the Gln residue Q295 (EU numbering) of the $C_H2$ domain of the antibody. In a particular embodiment, the invention relates to the method according to the invention, wherein the Gln residue in the Fc domain of the antibody is Gln residue Q295 (EU numbering) of the $C_H2$ domain of an IgG.

It is important to understand that Q295 is an extremely conserved amino acid residue in IgG type antibodies. It is conserved in human IgG1, 2, 3, 4, as well as in rabbit and rat antibodies amongst others. Hence, being able to use Q295 is a considerable advantage for making therapeutic antibody-payload conjugates, or diagnostic conjugates where the antibody is often of non-human origin. The method according to the invention does hence provide an extremely versatile and broadly applicable tool. Even though residue Q295 is extremely conserved among IgG type antibodies, some IgG type antibodies do not possess this residue, such as mouse IgG2a or IgG2b. Thus, it is to be understood that the antibody used in the method of the present invention is preferably an IgG type antibody comprising residue Q295 (EU numbering) of the $C_H2$ domain.

Further, it has been shown that engineered conjugates using Q295 for payload attachment demonstrate good pharmacokinetics and efficacy (Lhospice et al. 2015), and are capable of carrying even unstable toxins prone for degradation (Dorywalska et al. 2015). It is thus expected that similar effects will be seen with this site-specific method since the same residue is modified, but of glycosylated antibodies. Glycosylation may further contribute to overall ADC stability, removal of the glycan moieties as with the mentioned approaches has been shown to result in less-stable antibodies (Zheng et al. 2011).

According to one further embodiment of the invention, the antibody to which the payload or linking moiety is conjugated is glycosylated.

Typical IgG shaped antibodies are N-glycosylated in position N297 (Asp-X-Ser/Thr-motif) of the $C_H2$ domain.

Accordingly, in a particular embodiment, the invention relates to the method according to the invention, wherein the Gln residue in the Fc domain of the antibody is Gln residue Q295 (EU numbering) of the $C_H2$ domain of an IgG antibody that is glycosylated at residue N297 (EU numbering) of the $C_H2$ domain.

In the literature discussing the conjugation of linkers to a $C_H2$ Gln residue by means of a transglutaminase, the focus has been on small, low-molecular weight substrates. However, in the prior art literature, to accomplish such conjugation, a deglycosylation step in position N297, or the use of an aglycosylated antibody, is always described as necessary (WO 2015/015448; WO 2017/025179; WO 2013/092998).

Quite surprisingly, and against all expectations, however, site-specific conjugation to Q295 of glycosylated antibodies is indeed efficiently possible by using the above discussed oligopeptide structure.

Though Q295 is very close to N297, which is, in its native state, glycosylated, the method according to the invention, using the specified linker, still allows the conjugation of the linker or payload thereto.

However, as shown, the method according to the invention does not require an upfront enzymatic deglycosylation of Q295, nor the use of an aglycosylated antibody, nor a substitution of N297 against another amino acid, nor the introduction of a T299A mutation to prevent glycosylation.

These two points provide significant advantages under manufacturing aspects. An enzymatic deglycosylation step is undesired under GMP aspects, because it has to be made sure that the both the deglycosylation enzyme (e.g., PNGase F) as well as the cleaved glycan have to be removed from the medium.

Furthermore, no genetic engineering of the antibody for payload attachment is necessary, so that sequence insertions which may increase immunogenicity and decrease the overall stability of the antibody can be avoided.

The substitution of N297 against another amino acid has unwanted effects, too, because it may affect the overall stability of the entire Fc domain (Subedi et al, 2015), and the efficacy of the entire conjugate as a consequence that can lead to increased antibody aggregation and a decreased solubility (Zheng et al. 2011) that particularly gets important for hydrophobic payloads such as PBDs. Further, the glycan that is present at N297 has important immunomodulatory effects, as it triggers antibody dependent cellular cytotoxicity (ADCC) and the like. These immunomodulatory effects would get lost upon deglycosylation or any of the other approaches discussed above to obtain an aglycosylated antibody. Further, any sequence modification of an established antibody can also lead to regulatory problems, which is problematic because often times an accepted and clinically validated antibody is used as a starting point for ADC conjugation.

Hence, the method according to the invention allows to easily and without disadvantages make stoichiometrically well-defined ADCs with site specific payload binding.

In view of the above, it is stated that the method of the present invention is preferably used for the conjugation of an IgG antibody at residue Q295 (EU numbering) of the $C_H2$ domain of the antibody, wherein the antibody is glycosylated at residue N297 (EU numbering) of the $C_H2$ domain. However, it is expressly stated that the method of the invention also encompasses the conjugation of deglycosylated or aglycosylated antibodies at residue Q295 or any other suitable Gln residue of the antibody, wherein the Gln residue may be an endogenous Gln residue or a Gln residue that has been introduced by molecular engineering.

The invention also encompasses the conjugation of antibodies of other isotypes than IgG antibodies, such as IgA, IgE, IgM, IgD or IgY antibodies. Conjugation of these antibodies may take place at an endogenous Gln residue, for example an endogenous Gln residue in the Fc domain of the antibody, or at a Gln residue that has been introduced into the antibody by molecular engineering.

In general, the skilled person is aware of methods to determine at which position of an antibody a linker is conjugated. For example, the conjugation site may be determined by proteolytic digestion of the antibody-payload conjugate and LC-MS/MS analysis of the resulting fragments. For example, samples may be deglycosylated with GlycINATOR (Genovis) according to the instruction manual and subsequently digested with trypsin gold (mass spectrometry grade, Promega), respectively. Therefore, 1 μg of protein may be incubated with 50 ng trypsin at 37° C. overnight. LC-MS/MS analysis may be performed using a nanoAcquity HPLC system coupled to a Synapt-G2 mass spectrometer (Waters). For that, 100 ng peptide solution may be loaded onto an Acquity UPLC Symmetry C18 trap column (Waters, part no. 186006527) and trapped with 5 μL/min flow rate at 1% buffer A (Water, 0.1% formic acid) and 99% buffer B (acetonitrile, 0.1% formic acid) for 3 min. Peptides may then be eluted with a linear gradient from 3% to 65% Buffer B within 25 min. Data may be acquired in resolution mode with positive polarity and in a mass range from 50 to 2000 m/z. Other instrument settings may be as follows: capillary voltage 3.2 kV, sampling cone 40 V, extraction cone 4.0 V, source temperature 130° C., cone gas 35 L/h, nano flow gas 0.1 bar, and purge gas 150 L/h. The mass spectrometer may be calibrated with [Glu1]-Fibrinopeptide.

Further, the skilled person is aware of methods to determine the drug-to-antibody (DAR) ration or payload-to-antibody ratio of an antibody-payload construct. For example, the DAR may be determined by hydrophobic interaction chromatography (HIC) or LC-MS.

For hydrophobic interaction chromatography (HIC), samples may be adjusted to 0.5 M ammonium sulfate and assessed via a MAB PAK HIC Butyl column (5 μm, 4.6×100 mm, Thermo Scientific) using a full gradient from A (1.5 M ammonium sulfate, 25 mM Tris HCl, pH 7.5) to B (20% isopropanol, 25 mM Tris HCl, pH 7.5) over 20 min at 1 mL/min and 30° C. Typically, 40 μg sample may be used and signals may be recorded at 280 nm. Relative HIC retention times (HIC-RRT) may be calculated by dividing the absolute retention time of the ADC DAR 2 species by the retention time of the respective unconjugated mAb.

For LC-MS DAR determination, ADCs may be diluted with $NH_4HCO_3$ to a final concentration of 0.025 mg/mL. Subsequently, 40 μL of this solution may be reduced with 1 μL TCEP (500 mM) for 5 min at room temperature and then alkylated by adding 10 μL chloroacetamide (200 mM), followed by overnight incubation at 37° C. in the dark. For reversed phase chromatography, a Dionex U3000 system in combination with the software Chromeleon may be used. The system may be equipped with a RP-1000 column (1000 Å, 5 μm, 1.0×100 mm, Sepax) heated to 70° C., and an UV-detector set to a wavelength of 214 nm. Solvent A may consist of water with 0.1% formic acid and solvent B may comprise 85% acetonitrile with 0.1% formic acid. The reduced and alkylated sample may be loaded onto the column and separated by a gradient from 30-55% solvent B over the course of 14 min. The liquid chromatography system may be coupled to a Synapt-G2 mass spectrometer for identification of the DAR species. The capillary voltage of the mass spectrometer may be set to 3 kV, the sampling cone to 30 V and the extraction cone may add up to a value of 5 V. The source temperature may be set to 150° C., the desolvation temperature to 500° C., the cone gas to 20 l/h, the desolvation gas to 600 l/h, and the acquisition may be made in positive mode in a mass range from 600-5000 Da with 1 s scan time. The instrument may be calibrated with sodium iodide. Deconvolution of the spectra may be performed with the MaxEnt1 algorithm of MassLynx until convergence. After assignment of the DAR species to the chromatographic peaks, the DAR may be calculated based on the integrated peak areas of the reversed phase chromatogram.

According to one further embodiment of the invention, the net charge of the linker is neutral or positive.

The net charge of a peptide is usually calculated at neutral pH (7.0). In the simplest approach, the net charge is determined by adding the number of positively charged amino acid residues (Arg and Lys and optionally His) and the number of negatively charged ones (Asp and Glu), and calculate the difference of the two groups. In cases where the linker comprises non-canonical amino acids, the skilled person is aware of methods to determine the charge of the non-canonical amino acid at neutral pH.

According to one further embodiment of the invention, the linker does not comprise negatively charged amino acid residues.

Preferably, the oligopeptide does not comprise the negatively charged amino acid residues Glu and Asp or negatively charged non-canonical amino acids.

According to one further embodiment of the invention, the linker comprises positively charged amino acid residues.

According to one embodiment of the invention, the linker comprises at least two amino acid residues selected from the group consisting of Lysine or a Lysine derivative or a Lysine mimetic,
Arginine, and/or
Histidine.

In certain embodiments, the linker comprises at least one amino acid residue selected from the group consisting of Lysine or a Lysine derivative or a Lysine mimetic, Arginine, and Histidine.

In certain embodiments, the linker comprises at least one amino acid residue selected from the group consisting of Lysine, Arginine, and Histidine.

In certain embodiments, the linker comprises at least one amino acid residue selected from the group consisting of Arginine, and Histidine.

In certain embodiments, the linker comprises at least one arginine residue.

Table 8 shows that linkers with negative, neutral and positive net charge can be conjugated to a glycosylated antibody with the method of the invention. In particular, linkers comprising a positively charged arginine residue can be conjugated to the glycosylated antibody with high efficiency.

That is, in certain embodiments, the linker according to the invention has a neutral or positive net charge. In certain embodiments, the linker according to the invention has a neutral or positive net charge and comprises at least one arginine and/or histidine residue. In certain embodiments, the linker according to the invention has a neutral or positive net charge and comprises at least one arginine residue. In certain embodiments, the linker according to the invention does not comprise a lysine residue. In certain embodiments, the linker according to the invention has a neutral or positive net charge and does not comprise a lysine residue.

Table 8 further shows that linkers with the amino acid sequence Gly-[Gly/Ala]-Arg-B can be efficiently conjugated to a glycosylated antibody. Accordingly, in certain embodiments, the linker according to the invention has the sequence Gly-[Gly/Ala]-Arg-B or Gly-[Gly/Ala]-Arg-B-$(Aax)_n$.

In certain embodiments, the linker comprising one or more linking moiety B is selected from a group consisting of: GDC, GRCD, GRDC, GGDC, GGCD, GGEC, GGK$(N_3)$D, GGRCD, GGGDC, GC, GRC, GGRC, GRAC, GARC, GGHK$(N_3)$, GGK$(N_3)$RC, GARK$(N_3)$ and GGARK$(N_3)$. In a preferred embodiment, the linker comprising one or more linking moiety B is selected from a group consisting of: GGK$(N_3)$D, GGRCD, GC, GRC, GGRC, GARC, GGK$(N_3)$RC, GARK$(N_3)$ and GGARK$(N_3)$. In a more preferred embodiment, the linker comprising one or more linking moiety B is selected from a group consisting of: GGRCD, GC, GGRC, GARC, GGK$(N_3)$RC, GARK$(N_3)$ and GGARK$(N_3)$. In a most preferred embodiment, the linker comprising one or more linking moiety B is selected from a group consisting of: GC, GGRC, GARC and GGARK$(N_3)$. In certain embodiments, the linker comprising one or more linking moiety B is GGGK$(N_3)$.

According to one further embodiment of the invention, the antibody comprises the Asn residue N297 (EU numbering) in the $C_H2$ domain of the antibody.

According to one further embodiment of the invention, the N297 residue is glycosylated.

According to one further embodiment of the invention, the linker including the payload or linking moiety B is conjugated to the amide side chain of the Gln residue. That is, the amide side chain of the Gln residue of the antibody is conjugated to the N-terminal amino group of the linker via an isopeptide bond.

According to one further embodiment of the invention, the microbial transglutaminase is derived from a *Streptomyces* species, in particular from *Streptomyces mobaraensis*, preferentially with a sequence identity of 80% to the native enzyme. Accordingly, the MTG may be a native enzyme or may be an engineered variant of a native enzyme. As shown in FIGS. 8A-8B, high conjugation efficiencies have been obtained with a native MTG variant that has not been optimized for the conjugation of glycosylated antibodies.

One such microbial transglutaminase is commercially available from Zedira (Germany). It is recombinantly produced in *E. coli. Streptomyces mobaraensis* transglutaminase has an amino acid sequence as disclosed in SEQ ID NO 48. *S. mobaraensis* MTG variants with other amino acid sequences have been reported and are also encompassed by this invention (SEQ ID NO:28 and 49).

In another embodiment, a microbial transglutaminase *Streptomyces ladakanum* (formerly known as *Streptoverticillium ladakanum*) is being used. *Streptomyces ladakanum* transglutaminase (U.S. Pat. No. 6,660,510 B2) has an amino acid sequence as disclosed in SEQ ID NO 27.

Both the above transglutaminases can be sequence modified. In several embodiments, transglutaminases can be used which have 80% or more sequence identity with SEQ ID NOs 27, 28, 48 and 49.

Another suitable microbial transglutaminase is commercially from Ajinomoto, called ACTIVA TG. In comparison to the transglutaminase from Zedira, ACTIVA TG lacks 4 N terminal amino acids, but has similar activity.

Further microbial transglutaminases which can be used in the context of the present invention are disclosed in Kieliszek and Misiewicz 2014, WO 2015/191883 A1, WO 2008/102007 A1 and US 2010/0143970, the content of which is fully incorporated herein by reference.

In certain embodiments, a mutant variant of a microbial transglutaminase is used for the conjugation of a linker to an antibody. That is, the microbial transglutaminase that is used in the method of the present invention may be a variant of *S. mobaraensis* transgluatminase as set forth in SEQ ID NOs: 27 or 29. In certain embodiments, the recombinant *S. morabaensis* transglutaminase as set forth in SEQ ID NO:29 comprises the mutation G250D. In certain embodiments, the recombinant *S. morabaensis* transglutaminase as set forth in SEQ ID NO:29 comprises the mutations G250D and E300D. In certain embodiments, the recombinant *S. morabaensis* transglutaminase as set forth in SEQ ID NO:29 comprises the mutations D4E and G250D. In certain embodiments, the recombinant *S. morabaensis* transglutaminase as set forth in SEQ ID NO:29 comprises the mutations E120A and G250D. In certain embodiments, the recombinant *S. morabaensis* transglutaminase as set forth in SEQ ID NO:29 comprises the mutations A212D and G250D. In certain embodiments, the recombinant *S. morabaensis* transglutaminase as set forth in SEQ ID NO:29 comprises the mutations G250D and K327T.

Microbial transglutaminase may be added to the conjugation reaction at any concentration that allows efficient conjugation of an antibody with a linker. In certain embodiments, microbial transglutaminase may be added to the conjugation reaction at a concentration of less than 100 U/mL, 90 U/mL, 80 U/ml, 70 U/mL, 60 U/mL, 50 U/mL, 40 U/mL, 30 U/mL, 20 U/mL, 10 U/mL or 7 U/mL.

The method according to the invention comprises the use of a microbial transglutaminase. However, it is to be noted that an equivalent reaction may be carried out by an enzyme comprising transglutaminase activity that is of a non-microbial origin. Accordingly, also the antibody-payload conjugates according to the invention may be generated with an enzyme comprising transglutaminase activity that is of a non-microbial origin.

To obtain efficient conjugation, it is preferred that the linker is added to the antibody in molar excess. That is, in certain embodiments, the antibody is mixed with at least 5, 10, 20, 30, 40, 50, 60, 70, 80, 90 or 100 molar equivalents excess of peptide linker versus the antibody.

The method according to the invention is preferably carried out at a pH ranging from 6 to 8.5. Examples 1 and 2 show that the conjugation efficiency is highest at an pH of 7.6. Thus, in a preferred embodiment, the invention relates to a method according to the invention, wherein the conjugation of the linker to the antibody is achieved at a pH ranging from 6 to 8.5, more preferably at a pH ranging from 7 to 8. In a most preferred embodiment, the invention relates to a method according to the invention, wherein the conjugation of the linker to the antibody is achieved at pH 7.6.

The method of the invention may be carried out in any buffer that is suitable for the conjugation of a linker or linker-payload construct to an antibody with the method of the invention. Buffers that are suitable for the method of the invention include, without limitation, Tris, MOPS, HEPES, PBS or BisTris. Further, the buffer may comprise any salt concentration that is suitable for carrying out the method of the invention. For example, the buffer used in the method of the invention may have a salt concentration ≤150 mM, ≤140 mM, ≤130 mM, ≤120 mM, ≤110 mM, ≤100 mM, ≤90 mM, ≤80 mM, ≤70 mM, ≤60 mM, ≤50 mM, ≤40 mM, ≤30 mM, ≤20 mM, ≤10 mM or 1 mM. In certain embodiments, the buffer may be salt free.

It is to be noted that the optimal reaction conditions (e.g. pH, buffer, salt concentration) may vary between payloads and to some degree depend on the physicochemical properties of the linkers and/or payloads. However, no undue experimentation is required by the skilled person to identify reaction conditions that are suitable for carrying out the method of the invention.

According to one further embodiment of the invention, the linking moiety B is at least one selected from the group consisting of bioorthogonal marker group, or
other non-bio-orthogonal entities for crosslinking In certain embodiments of the invention, the linking moiety B comprises a bioorthogonal marker group, or
a non-bio-orthogonal entity for crosslinking.

The term "bioorthogonal marker group" has been established by Sletten and Bertozzi (2011) to designate reactive groups that can lead to chemical reactions to occur inside of living systems without interfering with native biochemical processes. A "non-bio-orthogonal entity for crosslinking" may be any molecule that comprises or consists of a first functional group, wherein the first functional group can be chemically or enzymatically crosslinked to a payload comprising a compatible second functional group. Even in cases where the crosslinking reaction is a non-bio-orthogonal reaction, it is preferred that the reaction does not introduce additional modifications to the antibody other than the crosslinking of the payload to the linker. In view of the above, the linking moiety B may either consist of the "bioorthogonal marker group" or the "non-bio-orthogonal entity" or may comprise the "bioorthogonal marker group" or the "non-bio-orthogonal entity". For example, in case of the linking moiety Lys($N_3$), both the entire Lys($N_3$) and the azide group alone may be seen as a bioorthogonal marker group within the present invention.

According to one further embodiment of the invention, the bioorthogonal marker group or the non-bio-orthogonal entity is at least one selected from the group consisting of:

—N—N≡N, or —$N_3$
Lys($N_3$)
Tetrazine
Alkyne
DBCO
BCN
Norborene
Transcyclooctene
RCOH (aldehyde),
Acyltrifluoroborates,
—SH, and
Cysteine These groups can for example engage in any of the binding reactions shown in table 4:

TABLE 4

| binding partner 1 | binding partner 2 | reaction type |
|---|---|---|
| —N—N≡N | cyclooctyne derivatives (e.g. DIFO, BCN, DIBAC, DIBO, ADIBO/DBCO) | SPAAC |
| —N—N≡N | Alkyne | CuAAC |
| —N—N≡N | Triarylphosphines | Staudinger ligation |
| tetrazine | Cyclopropene<br>Norborene<br>Cyclooctyne<br>(BCN) | tetrazine ligation |
| —SH, e.g., of a Cys residue | Maleimide | Thiol-Maleimide conjugation |
| Amine | N-hydroxysuccinimid | |
| —O-carbamoylhydroxylamines | Acyltrifluoroborates | KAT-ligation (potassium acyl-trifluoroborate) |
| 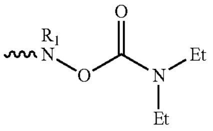 | 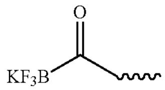 | |
| $R_x$—S—S—$R_y$ | $R_2$—SH + reducing agent (e.g., TCEP, DTT) | Direct disulfide bioconjugation |
| —CHO (aldehyde) | HIPS-probe | Hydrazino-iso-Pictet-Spengler (HIPS) |

TABLE 4-continued

| binding partner 1 | binding partner 2 | reaction type |
| --- | --- | --- |
| | 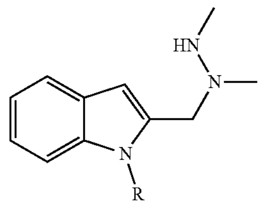 | |
| —CHO (aldehyde) | N-pyrrolyl alanine derivative | pyrrolyl alanine Pictet-Spengler (PAPS) |
| —CHO (aldehyde) | $R_1$—N—N—$R_2$ | Hydrazone-ligation |
| | HO—N—$R_1$ | Oxime-ligation |
| | H2N—CH$R_1$—CH2—SH | Thiazolidine-Ligation |
| maleimide | —SH, e.g., of a Cys residue | Thiol-Maleimide conjugation |

In the above table 4, the said linking moieties can either be or comprise what is called therein "binding partner 1" or "binding partner 2".

According to one further embodiment of the invention, the linking moiety B is a Cys residue with a free sulfhydryl group.

The free sulfhydryl group of such Cys residue (or derivative) can be used to conjugate a maleimide-comprising linker toxin construct thereto. See FIG. 5 for some more details of the conjugation reaction, and some potential linker constructs.

Toxins comprising a maleimide linker have frequently been used, and also approved by medical authorities, like Adcetris. Thus drugs comprising a MMAE toxin are conjugated to a linker comprising (i) a p-aminobenzyl spacer, (ii) a dipeptide and (iii) a maleimidocaproyl linker, which enables the conjugation of the construct to the free sulfhydryl group of a Cys residue in the antibody.

Providing a Cys-residue in the linker according to the present invention does therefore have the advantage to be able to use off-the-shelf-toxin-maleimide constructs to create antibody-payload conjugates, or, more generally, to be able to fully exploit the advantages of Cys-maleimide binding chemistry. At the same time, off-the-shelf antibodies can be used, which do not have to be deglycosylated.

In specific embodiments, the Cys residue is C-terminal, or intrachain in the peptide linker.

In another embodiment, the linking moiety B comprises an azide group. The skilled person is aware of molecules comprising an azide group which may be incorporated into a linker according to the invention, such as 6-azido-lysine (Lys($N_3$)) or 4-azido-homoalanine (Xaa($N_3$)). Linking moieties comprising an azide group may be used as substrates in various bio-orthogonal reactions, such as strain-promoted azide-alkyne cycloaddition (SPAAC), copper-catalyzed azide-alkyne cycloaddition (CuAAC) or Staudinger ligation. For example, in certain embodiments, payloads comprising a cyclooctene derivative, such as DBCO, may be coupled to a linker comprising an azide group by SPAAC (see FIG. 15).

In yet another embodiment, the linking moiety B comprises a tetrazine. The skilled person is aware of tetrazine-comprising molecules which may be incorporated into a linker according to the invention, preferably amino acid derivatives comprising a tetrazine group (see for example FIG. 7A). Linking moieties comprising a tetrazine may be used as substrates in a bio-orthogonal tetrazine ligation. For example, in certain embodiments, payloads comprising a cyclopropene, a norborene or a cyclooctyne group, such as bicyclo[6.1.0]nonyne (BCN), may be coupled to a linker comprising a tetrazine group.

The invention further encompasses linkers comprising two different bio-orthogonal marker groups and/or non-bio-orthogonal entities. For example, a linker according to the invention may comprise an azide-comprising linking moiety, such as Lys($N_3$) or Xaa($N_3$), and a sulfhydryl-comprising linking moiety, such as cysteine. In certain embodiments, the linker according to the invention may comprise an azide-comprising linking moiety, such as Lys($N_3$) or Xaa($N_3$), and a tetrazine-comprising linking moiety, such as a tetrazine-modified amino acid. In certain embodiments, the linker according to the invention may comprise a sulfhydryl-comprising linking moiety, such as cysteine, and a tetrazine-comprising linking moiety, such as a tetrazine-modified amino acid. Linkers comprising two different bio-orthogonal marker groups and/or non-bio-orthogonal entities have the advantage that they can accept two distinct payloads and thus result in antibody-payload conjugates comprising more than one payload.

According to one further embodiment of the invention, it is provided that, in case B is a linking moiety, a further step of linking the actual payload to the linking moiety is carried out. A number of chemical ligation strategies have been developed that fulfill the requirements of bio-orthogonality, including the 1,3-dipolar cycloaddition between azides and cyclooctynes (also termed copper-free click chemistry, Baskin et al (2007)), between nitrones and cyclooctynes (Ning et al (2010)), oxime/hydrazone formation from aldehydes and ketones (Yarema, et al (1998)), the tetrazine ligation (Blackman et al (2008)), the isonitrile-based click reaction (Stockmann et al (2011)), and most recently, the quadricyclane ligation (Sletten & Bertozzi (JACS, 2011)), Copper(I)-catalyzed azide-alkyne cycloaddition (CuAAC, Kolb & Sharpless (2003)), Strain-promoted azide-alkyne cycloaddition (SPAAC, Agard et al (2004)), or Strain-promoted alkyne-nitrone cycloaddition (SPANC, MacKenzie et al (2014)).

All these documents are incorporated by reference herein to provide sufficient enabling disclosure, and avoid lengthy repetitions.

It is to be understood that the payload is preferably coupled to the bio-orthogonal marker group or the non-bio-orthogonal entity of the linker according to the invention after said linker has been conjugated to a Gln residue of an antibody by means of a microbial transglutaminase. However, the invention also encompasses antibody-payload conjugates wherein a payload has been coupled to a linker comprising a linking moiety in a first step and wherein the resulting linker-payload construct is conjugated to the antibody by a microbial transglutaminase in a second step.

In a particular embodiment, the invention relates to the method according to the invention, wherein the payload is linked to the linking moiety B of the antibody-linker conjugate via a click-reaction, for example any one of the click reactions mentioned above. In a preferred embodiment, the click reaction is SPAAC.

According to one further embodiment of the invention, the payload B is at least one selected from the group consisting of:

- toxin
- cytokine
- growth factor
- radionuclide
- hormone
- anti-viral agent
- anti-bacterial agent
- fluorescent dye
- immunoregulatory/immunostimulatory agent
- half-life increasing moiety
- solubility increasing moiety
- a polymer-toxin conjugate
- a nucleic acid
- a biotin or streptavidin moiety
- a vitamin
- a target binding moiety, and
- anti-inflammatory agent.

Half-life increasing moieties are, for example, PEG-moieties (polyethylenglycol moieties; PEGylation), other polymer moieties, PAS moieties (oliogopeptides comprising Proline, Alanine and Serine; PASylation), or Serum albumin binders. Solubility increasing moieties are, for example PEG-moieties (PEGylation) or PAS moieties (PASylation).

Polymer-toxin conjugates are polymers that are capable of carrying many payload molecules. Such conjugates are sometimes also called fleximers, as e.g. marketed by Mersana therapeutics.

One example of a nucleic acid payload is MCT-485, which is a very small non-coding double stranded RNA which has oncolytic and immune activating properties, developed by MultiCell Technologies, Inc.

Anti-inflammatory agents are for example anti-inflammatory cytokines, which, when conjugated to a target specific antibody, can ameliorate inflammations caused, e.g., by autoimmune diseases.

The term "fluorescent dye" as used herein refers to a dye that absorbs light at a first wavelength and emits at second wavelength that is longer than the first wavelength. In certain embodiment, the fluorescent dye is a near-infrared fluorescent dye, which emits light at a wavelength between 650 and 900 nm. In this region, tissue autofluorescence is lower, and less fluorescence extinction enhances deep tissue penetration with minimal background interference. Accordingly, near-infrared fluorescent imaging may be used to make tissues that are bound by the antibody-payload conjugate of the invention visible during surgery. "Near-infrared fluorescent dyes" are known in the art and commercially available. In certain embodiments, the near-infrared fluorescent dye may be IRDye 800CW, Cy7, Cy7.5, NIR CF750/770/790, DyLight 800 or Alexa Fluor 750.

The term "radionuclide", as used herein, relates to medically useful radionuclides, including, for example, positively charged ions of radiometals such as Y, In, Tb, Ac, Cu, Lu, Tc, Re, Co, Fe and the like, such as $^{90}Y$, $^{111}In$, $^{67}Cu$, $^{77}Lu$, $^{99}Tc$, $^{161}Tb$, $^{225}Ac$ and the like. The radionuclide may be comprised in a chelating agent. Further, the radionuclide may be a therapeutic radionuclide or a radionuclide that can be used as contrast agent in imaging techniques as discussed below. Radionuclides or molecules comprising radionuclides are known in the art and commercially available.

The term "toxin" as used herein relates to any compound that is poisonous to a cell or organism. A toxin, thus can be, e.g. small molecules, nucleic acids, peptides, or proteins. Specific examples are neurotoxins, necrotoxins, hemotoxins and cyclotoxins. According to one further embodiment of the invention, the toxin is at least one selected from the group consisting of

- Pyrrolobenzodiazepines (PBD)
- Auristatins (e.g., MMAE, MMAF)
- Maytansinoids (Maytansine, DM1, DM4, DM21)
- Duocarmycins
- Tubulysins
- Enediyenes (e.g. Calicheamicin)
- PNUs, doxorubicins
- Pyrrole-based kinesin spindle protein (KSP) inhibitors
- Calicheamicins
- Amanitins (e.g. α-Amanitin), and/or
- Camptothecins (e.g. exatecans, deruxtecans)

In certain embodiments, the payload is an auristatin. As used herein, the term "auristatin" refers to a family of anti-mitotic agents. Auristatin derivatives are also included within the definition of the term "auristatin". Examples of auristatin include, but are not limited to, synthetic analogues of auristatin E (AE), monomethyl auristatin E (MMAE), monomethyl auristatin F (MMAF) and dolastatin.

In certain embodiments, the payload is a maytansinoid. In the context of the present invention, the term "maytansinoid" refers to a class of highly cytotoxic drugs originally isolated from the African shrub *Maytenus ovatus* and further maytansinol (Maytansinol) and C-3 ester of natural maytansinol (U.S. Pat. No. 4,151,042); C-3 ester analog of synthetic maytansinol (Kupchan et al., J. Med. Chem. 21: 31-37, 1978; Higashide et al., Nature 270: 721-722, 1977; Kawai et al., Chem. Farm. Bull. 32: 3441-3451; and U.S. Pat. No. 5,416,064); C-3 esters of simple carboxylic acids (U.S. Pat. Nos. 4,248,870; 4,265,814; 4,308,268; 4,308,269; 4,309,428; 4,317,821; 4,322,348; and 4,331,598); and C-3 esters with derivatives of N-methyl-L-alanine (U.S. Pat. Nos. 4,137,230; 4,260,608; and Kawai et al., Chem. Pharm Bull. 12: 3441, 1984). Exemplary maytansinoids that may be used in the method of the invention or that may be comprised in the antibody-payload conjugate of the invention are DM1, DM3, DM4 and/or DM21.

In certain embodiments, the toxic payload molecule is duocarmycin. Suitable duocarmycins may be e.g. duocarmycin A, duocarmycin BL duocarmycin B2, duocarmycin CI, duocarmycin C2, duocarmycin D, duocarmycin SA, duocarmycin MA, and CC-1065. The term "duocarmycin" should be understood as referring also to synthetic analogs of duocarmycins, such as adozelesin, bizelesin, carzelesin, KW-2189 and CBI-TMI.

The toxin, in the sense of the present invention may also be an inhibitor of a drug efflux transporter. Antibody-payload conjugates comprising a toxin and an inhibitor of a drug efflux transporter may have the advantage that, when internalized into a cell, the inhibitor of the drug efflux transporter prevents efflux of the toxin out of the cell. Within the present invention, the drug efflux transporter may be P-glycoprotein. Some common pharmacological inhibitors of P-glycoprotein include: amiodarone, clarithromycin, ciclosporin, colchicine, diltiazem, erythromycin, felodipine, ketoconazole, lansoprazole, omeprazole and other proton-pump inhibitors, nifedipine, paroxetine, reserpine, saquinavir, sertraline, quinidine, tamoxifen, verapamil, and duloxetine. Elacridar and CP 100356 are other common P-gp inhibitors. Zosuquidar and tariquidar were also developed with this in mind. Lastly, valspodar and reversan are other examples of such agents.

The vitamin can be selected from the group consisting of folates, including folic acid, folacin, and vitamin B9.

The target binding moiety can be a protein or small molecule being capable of specifically binding to a protein or non-protein target. In one embodiment, such target binding moiety is a scFv shaped antibody, a Fab fragment, a F(ab)2 fragment, a nanobody, affibody, a diabody, a VHH shaped antibody, or an antibody mimetic, including a DARPIN.

It is to be understood that the payload can be coupled to a linking moiety of a linker by any suitable reaction, such as a click reaction, or may be attached to the linker by chemical synthesis.

According to one further embodiment of the invention, the linker has two or more linking moieties B.

In such embodiment, an antibody-payload conjugate can be created with, for example, an antibody to payload ratio of 4, with two payloads conjugated to each Q295 residue.

According to one further embodiment of the invention, the two or more linking moieties B differ from one another.

In such embodiment, a first linking moiety could for example be or comprise an azide (N3), while a second linking moiety could be or comprise a tetrazine. Such oligopeptide linker thus allows to conjugate two different payloads to two Gln residues of the antibody, i.e., the Q295 residues of the two $C_H2$ domains of the antibody.

In such way, an antibody payload ratio of 2+2 can be obtained. Using a second payload allows for the development of a completely new class of antibody payload conjugates that go beyond current therapeutic approaches with respect to efficacy and potency.

Such embodiment allows, inter alia, to target two different structures in a cell, like, e.g., the DNA and microtubule. Because some cancers can be resistant to one drug, like e.g., a mirobutule toxin, the DNA-toxin can still kill the cancer cells.

According to another embodiment, two drugs could be used that are only fully potent when they are released at the same time and in the same tissue. This may lead to reduced off-target toxicity in case the antibody is partially degraded in healthy tissues or one drug is pre-maturely lost.

Furthermore, dual-labeled probes can be used for non-invasive imaging and therapy or intra/post-operative imaging/surgery. In such embodiment, a tumor patient can be selected by means of the non-invasive imaging. Then, the tumor can be removed surgically using the other imaging agent (e.g., a fluorescent dye), which helps the surgeon or robot to identify all cancerous tissue.

According to another aspect of the invention, an antibody-payload conjugate is provided which has been generated with a method according to any one of the aforementioned steps.

According to another aspect of the invention, a linker is provided comprising the peptide structure (shown in N->C direction)

$$\text{Gly-(Aax)}_m\text{-B-(Aax)}_n$$

wherein Gly comprises an N-terminal primary amine, and wherein m is an integer between ≥0 and ≤12 n is an integer between ≥0 and ≤12 m+n≥0,

Aax is an amino acid or an amino acid derivative, and

B is a payload or a linking moiety, and wherein the linker can be conjugated to an antibody by a microbial transglutaminase via the N-terminal primary amine of the N-terminal Gly of the linker.

Said linker is suitable to be conjugated, via the N-terminal primary amine of the N-terminal glycine (Gly) residue, to a glutamine (Gln) residue comprised in the heavy or light chain of an antibody, by means of a transglutaminase enzyme.

Generally, the advantages and embodiments discussed above in accordance with the method of the present invention do also apply to this aspect. i.e., the linker as composition of matter. Hence, those embodiments shall be deemed disclosed also with the linker as composition of matter.

It is important to understand that in different linker peptides shown herein, the C-terminus may or may not be protected, even if shown otherwise. Protection can be accomplished by amidation. In the context of the present invention, linker peptides that are protected and unprotected at the C-terminus are encompassed.

In a particular embodiment, the invention relates to the linker according to the invention, wherein the linker comprises two or more payloads and/or linking moieties B.

In certain embodiments, the linker may comprise two or more linking moieties and/or payloads. That is the linker may have the peptide structure (shown in N->C direction)

$$\text{Gly-(Aax)}_m\text{-B}_1\text{-(Aax)}_n\text{-B}_2\text{-(Aax)}_o$$

wherein m, n and o are integers between ≥0 and ≤12, m+n+o≥0,

Aax is an amino acid or an amino acid derivative, and $B_1$ and $B_2$ are payloads and/or linking moieties, wherein $B_1$ and $B_2$ may be identical or different from each other and wherein the linker can be conjugated to an antibody by a microbial transglutaminase via the N-terminal primary amine of the N-terminal Gly of the linker.

In other embodiments, the linker may comprise three linking moieties and/or payloads. That is the linker may have the peptide structure (shown in N->C direction)

$$\text{Gly-(Aax)}_m\text{-B}_1\text{-(Aax)}_n\text{-B}_2\text{-(Aax)}_o\text{-B}_3\text{-(Aax)}_p$$

wherein m, n, o and p are integers between ≥0 and ≤12, m+n+o+p≥0,

Aax is an amino acid or an amino acid derivative, and $B_1$, $B_2$ and $B_3$ are payloads and/or linking moieties, wherein $B_1$, $B_2$ and $B_3$ may be identical or different from each other and wherein the linker can be conjugated to an antibody by a microbial transglutaminase via the N-terminal primary amine of the N-terminal Gly of the linker.

It is to be understood, that the invention also encompasses linkers comprising more than three linking moieties and/or payloads, such as 4, 5 or 6 linking moieties and/or payloads. In this case, the peptide structure of the linkers follows the same pattern as described above for the linkers comprising 2 or 3 linking moieties and/or payloads.

In certain embodiments, the invention relates to a linker having the peptide structure (shown in N->C direction)

$$\text{Gly-(Aax)}_m\text{-B-(Aax)}_n$$

wherein m is an integer between ≥0 and ≤12 n is an integer between ≥0 and ≤12 m+n≥0,

Aax is an amino acid or an amino acid derivative, and

B is a payload or a linking moiety, and wherein the linker can be conjugated to an antibody by a microbial transglutaminase via the N-terminal primary amine of the N-terminal Gly of the linker.

In this case, it is to be understood that the moiety B may comprise more than one payload and/or linking moiety. For example, B may stand for (B'-$(Aax)_o$-B"), wherein B' and B" are payloads and/or linking moieties and wherein o is an integer between ≥0 and ≤12. Alternatively, B may stand for (B'-$(Aax)_o$-B"-$(Aax)_p$-B'"), wherein B', B" and B'" are payloads and/or linking moieties and wherein o and p are integers between ≥0 and ≤12.

In preferred embodiments, m and/or n is ≥1, ≥2, ≥3, ≥4, ≥5, ≥6, ≥7, ≥8, ≥9, ≥10, or ≥11. In other preferred embodiments, m and/or n is ≤12, ≤11, ≤10, ≤9, ≤8, ≤7, ≤6, ≤5, ≤4, ≤3, ≤2, or ≤1. In further preferred embodiments, m+n is ≥1, ≥2, ≥3, ≥4, ≥5, ≥6, ≥7, ≥8, ≥9, ≥10, or ≥11. In still further preferred embodiments m+n is ≤12, ≤11, ≤10, ≤9, ≤8, ≤7, ≤6, ≤5, ≤4, ≤3, ≤2, or ≤1.

Members of both ranges can be combined with another to disclose a preferred length range with lower and upper limit.

Accordingly, in a particular embodiment, the invention relates to a linker according to the invention, wherein m+n is ≤12, ≤11, ≤10, ≤9, ≤8, ≤7, ≤6, ≤5 or ≤4.

In further embodiments, the linker is not cleavable by cathepsin B, and/or the linker does not comprise a valine-alanine motif or a valine-citrulline motif, and/or the linker does not comprise Polyethylenglycol or a Polyethylenglycol derivative.

According to one embodiment, the linking moiety B is at least one selected from the group consisting of bioorthogonal marker group other non-bio-orthogonal entities for crosslinking.

In certain embodiments, at least one linking moiety B of the linker comprises or consists of a bioorthogonal marker group; or a non-bio-orthogonal entity for crosslinking.

According to one embodiment, the bioorthogonal marker group or the non-bio-orthogonal entity is at least one selected from the group consisting of —N—N≡N, or —$N_3$ Lys($N_3$)

tetrazine alkyne

DBCO

BCN norborene transcyclooctene

—RCOH (aldehyde), acyltrifluoroborates,

—SH, and cysteine.

In further embodiments, the net charge of the linker is neutral or positive, and/or the linker does not comprise negatively charged amino acid residues, and/or the linker comprises positively charged amino acid residues, and/or the linker comprises at least two amino acid residues selected from the group consisting of Lysine, Arginine, and/or Histidine.

In certain embodiments, the linker comprises at least one amino acid residue selected from the group consisting of Lysine, Arginine, and Histidine.

In certain embodiments, the linker comprises at least one amino acid residue selected from the group consisting of Arginine, and Histidine.

That is, in certain embodiments, the linker according to the invention has a neutral or positive net charge. In certain embodiments, the linker according to the invention has a neutral or positive net charge and comprises at least one arginine and/or histidine residue. In certain embodiments, the linker according to the invention does not comprise a lysine residue. In certain embodiments, the linker has a neutral or positive net charge and does not comprises a lysine residue.

According to one embodiment, the primary amine group is suitable to serve as the substrate of a microbial transglutaminase (MTG).

According to one further embodiment, the linker is suitable for generating an antibody-payload conjugate by means of a microbial transglutaminase (MTG).

According to one further embodiment, the linker is selected from a) the list as shown in table 5 and/or b) any one of SEQ ID NO 1-25

In a particular embodiment, the invention relates to a linker according to the invention, wherein the linker is selected from the list as shown in table 5.

According to yet another aspect of the invention, a linker-payload construct is provided, comprising at least a) a linker according to the above description, and b) one or more payloads, wherein, in said construct, the linker and/or the payload have optionally been chemically modified during binding to allow covalent or non-covalent binding, to form said construct.

In certain embodiments, a linker-payload construct is provided, comprising at least a) a linker according to the above description, and b) one or more payloads, wherein the one or more payloads are covalently or non-covalently bound to the linker.

In a particular embodiment, the invention relates to the linker-payload construct according to the invention, wherein in said construct, the one or more payloads have been covalently bound to the linking moiety B of the linker with a click reaction. That is, the one or more payloads may be attached to a linking moiety B by any of the click reactions discussed above, such as, without limitation, SPAAC, tetrazine ligation or thiol-maleimide conjugation.

Besides a click reaction between the linking moiety in the linker and the payload, the payload may be covalently bound to the linker by any enzymatic or non-enzymatic reaction known in the art. For that, the payload may be bound to the C-terminus of the linker or to an amino acid side chain of the linker.

In certain embodiments, the payload is coupled to a linker by chemical synthesis. The skilled person is aware of methods to couple a payload to a peptide linker by chemical synthesis. For example, an amine-comprising payload, or a thiol-comprising payload (for e.g. maytansine analogs), or an hydroxyl-containing payload (for e.g. SN-38 analogs) may be attached to the C-terminus of a peptide linker by chemical synthesis to obtain, for example, the linkers shown in FIGS. 17A-17D. However, the skilled person is aware of further reactions and reactive groups that may be utilized for coupling a payload to the C-terminus or the side chain of an amino acid or amino acid derivative by chemical synthesis. Typical reactions that may be used to couple a payload to a peptide linker by chemical synthesis include, without limitation: peptide coupling, activated ester coupling (NHS ester, PFP ester), click reaction (CuAAC, SPAAC), michael addition (thiol maleimide conjugation). The coupling of payloads to peptides has been extensively described in the prior art, for example by Costoplus et al. (ACS Med Chem, 2019), Sonzini et al. (Bioconj Chem, 2019), Bodero et al. (Belstein, 2018), Nunes et al. (RSC Adv, 2017), Doronina et al. (Bioconj Chem, 2006), Nakada et al. (Bioorg Med Chem, 2016) and Dickgiesser et al. (Bioconj Chem, 2020).

In a particular embodiment, the invention relates to the linker-payload construct according to the invention, wherein in said construct, the linker and/or the payload have optionally been chemically modified during binding to allow covalent or non-covalent binding, to form said construct.

In case two or more payloads are being used, the latter can be identical or different from one another.

In one embodiment, the payload is at least one selected from the group consisting of a toxin
a cytokine
a growth factor
a radionuclide
a hormone
an anti-viral agent
an anti-bacterial agent
a fluorescent dye
an immunoregulatory/immunostimulatory agent
a half-life increasing moiety
a solubility increasing moiety
a polymer-toxin conjugate
a nucleic acid
a biotin or streptavidin moiety
a vitamin
a target binding moiety, and
an anti-inflammatory agent.
a protein degrader (PROTACs)

In another embodiment, the toxin is at least one selected from the group consisting of pyrrolobenzodiazepines (PBD)
auristatins (e.g., MMAE, MMAF)
maytansinoids (Maytansine, DM1, DM4, DM21)
duocarmycins
tubulysins
enediyenes (e.g. Calicheamicin)
PNUs, doxorubicins
pyrrole-based kinesin spindle protein (KSP) inhibitors
calicheamicins
amanitins (e.g. α-amanitin), and/or
camptothecins (e.g. exatecans, deruxtecans)

According to another aspect of the invention, an antibody-payload conjugate is provided comprising a) one or more linker-payload constructs according to the above description, and
b) an antibody comprising at least one Gln residue in the heavy or light chain, wherein, in said conjugate, the linker-payload constructs and/or the antibody have optionally been chemically modified during conjugation to allow covalent or non-covalent conjugation, to form said conjugate.

In a particular embodiment, the invention relates to an antibody payload conjugate comprising a) one or more linker-payload constructs according to the above description, and
b) an antibody comprising at least one Gln residue in the heavy or light chain, wherein, the linker-payload construct is conjugated to the amide side chain of a Gln residue in the heavy or light chain of the antibody via an N-terminal primary amine of the N-terminal glycine residue comprised in the linker-payload construct In a particular embodiment, the invention relates to the antibody-payload conjugate according to the invention, wherein the conjugation has been achieved with a microbial transglutaminase (MTG).

In a particular embodiment, the invention relates to the antibody-payload conjugate according to the invention, wherein the conjugation has been achieved before or after formation of the linker-payload construct. That is, the invention encompasses antibody-payload conjugates wherein the linkers have been conjugated to the antibody in a first step before the one or more payloads are coupled to the linking moieties of the linkers in a second step. However, the invention also encompasses antibody-payload conjugates, wherein the one or more payloads are coupled to the linking moieties of the linkers in a first step, and wherein the resulting linker-payload constructs are then conjugated to the antibody in a second step. Further, the one or more payloads may be attached to a peptide linker by means of chemical synthesis and the resulting linker-payload construct may then be conjugated to the antibody in a one-step reaction.

In a particular embodiment, the invention relates to the antibody-payload conjugate according to the invention, wherein the antibody is an IgG, IgE, IgM, IgD, IgA or IgY antibody, or a fragment or recombinant variant thereof, wherein the fragment or recombinant variant thereof retains target binding properties and comprises a $C_H2$ domain.

In a particular embodiment, the invention relates to the antibody-payload conjugate according to the invention, wherein the antibody is an IgG antibody.

In a particular embodiment, the invention relates to the antibody-payload conjugate according to the invention, wherein the antibody is a glycosylated antibody, a deglycosylated antibody or an aglycosylated antibody.

In a particular embodiment, the invention relates to the antibody-payload conjugate according to the invention, wherein the glycosylated antibody is an IgG antibody that is glycosylated at residue N297 (EU numbering) of the $C_H2$ domain or wherein the glycosylated antibody is an antibody of a different isotype that is glycosylated at a residue that is homologous to residue N297 (EU numbering) of the $C_H2$ domain of an IgG antibody.

In a particular embodiment, the invention relates to the antibody-payload conjugate according to the invention, wherein (a) the linker-payload construct is conjugated to a Gln residue which has been introduced into the heavy or light chain of the antibody by molecular engineering or (b) the linker-payload construct is conjugated to a Gln residue in the Fc domain of the antibody.

In a particular embodiment, the invention relates to the antibody-payload conjugate according to the invention, wherein the Gln residue in the Fc domain of the antibody is Gln residue Q295 (EU numbering) of the $C_H2$ domain of an IgG antibody or a homologous Gln residue of an antibody of a different isotype.

In a particular embodiment, the invention relates to the antibody-payload conjugate according to the invention, wherein the Gln residue in the Fc domain of the antibody is Gln residue Q295 (EU numbering) of the $C_H2$ domain of an IgG antibody that is glycosylated at residue N297 (EU numbering) of the $C_H2$ domain.

The antibody of the method or the antibody-payload conjugate of the invention may be any antibody, preferably any IgG type antibody. For example, the antibody may be, without limitation Brentuximab, Trastuzumab, Gemtuzumab, Inotuzumab, Avelumab, Cetuximab, Rituximab, Daratumumab, Pertuzumab, Vedolizumab, Ocrelizumab, Tocilizumab, Ustekinumab, Golimumab, Obinutuzumab, Polatuzumab or Enfortumab.

That is, in certain embodiments, the invention relates to an antibody-payload conjugate according to the invention, wherein the antibody is Brentuximab. In a further embodiment, the invention relates to an antibody-payload conjugate according to the invention, wherein the antibody is Trastuzumab. In a further embodiment, the invention relates to an antibody-payload conjugate according to the invention, wherein the antibody is Gemtuzumab. In a further embodiment, the invention relates to an antibody-payload conjugate according to the invention, wherein the antibody is Inotuzumab. In a further embodiment, the invention relates to an antibody-payload conjugate according to the invention, wherein the antibody is Avelumab. In a further embodiment, the invention relates to an antibody-payload conjugate according to the invention, wherein the antibody is Cetuximab. In a further embodiment, the invention relates to an antibody-payload conjugate according to the invention, wherein the antibody is Rituximab. In a further embodiment, the invention relates to an antibody-payload conjugate according to the invention, wherein the antibody is Daratumumbab. In a further embodiment, the invention relates to an antibody-payload conjugate according to the invention, wherein the antibody is Pertuzumab. In a further embodiment, the invention relates to an antibody-payload conjugate according to the invention, wherein the antibody is Vedolizumab. In a further embodiment, the invention relates to an antibody-payload conjugate according to the invention, wherein the antibody is Ocrelizumab. In a further embodiment, the invention relates to an antibody-payload conjugate according to the invention, wherein the antibody is Tocilizumab. In a further embodiment, the invention relates to an antibody-payload conjugate according to the invention, wherein the antibody is Ustekinumab. In a further embodiment, the invention relates to an antibody-payload conjugate according to the invention, wherein the antibody is Golimumab. In a further embodiment, the invention relates to an antibody-payload conjugate according to the invention, wherein the antibody is Obinutuzumab. In a further embodiment, the invention relates to an antibody-payload conjugate according to the invention, wherein the antibody is Polatuzumab. In a further embodiment, the invention relates to an antibody-payload conjugate according to the invention, wherein the antibody is Enfortumab.

In a particular embodiment, the invention relates to the antibody-payload conjugate according to the invention, wherein the Gln residue that has been introduced into the heavy or light chain of the antibody by molecular engineering is N297Q (EU numbering) of the $C_H2$ domain of an aglycosylated IgG antibody.

In a particular embodiment, the invention relates to the antibody-payload conjugate according to the invention, wherein the Gln residue that has been introduced into the heavy or light chain of the antibody by molecular engineering is comprised in a peptide that has been (a) integrated into the heavy or light chain of the antibody or (b) fused to the N- or C-terminal end of the heavy or light chain of the antibody.

In a particular embodiment, the invention relates to the antibody-payload conjugate according to the invention, wherein the peptide comprising the Gln residue has been fused to the C-terminal end of the heavy chain of the antibody.

In a particular embodiment, the invention relates to the antibody-payload conjugate according to the invention, wherein the peptide comprising the Gln residue is selected from a group consisting of: LLQGG, LLQG, LSLSQG, GGGLLQGG, GLLQG, LLQ, GSPLAQSHGG, GLLQGGG, GLLQGG, GLLQ, LLQLLQGA, LLQGA, LLQYQGA, LLQGSG, LLQYQG, LLQLLQG, SLLQG, LLQLQ, LLQLLQ, LLQGR, EEQYASTY, EEQYQSTY, EEQYNSTY, EEQYQS, EEQYQST, EQYQSTY, QYQS, QYQSTY, YRYRQ, DYALQ, FGLQRPY, EQKLISEEDL, LQR and YQR.

In a particular embodiment, the invention relates to the antibody-payload conjugate according to the invention, wherein the antibody-payload conjugate comprises at least on toxin.

That is, the antibody-payload conjugate of the invention comprises an antibody that is conjugated to at least one linker, wherein the one linker comprises at least one toxin. In certain embodiments, the antibody-payload conjugate comprises two linkers, wherein each heavy chain of the antibody is conjugated to one linker, respectively. In certain embodiments, the antibody-payload conjugate comprises four linkers, wherein each heavy chain of the antibody is conjugated to two linkers, respectively. In such cases, each linker may contain one or more payloads, such as toxins.

In certain embodiments, the antibody-payload conjugate according to the invention comprises two linkers, wherein each linker comprises one payload, for example a toxin. In other embodiments, the antibody-payload conjugate according to the invention comprises two linkers, wherein each linker comprises two payloads, for example one toxin and one other payload or two identical or different toxins. In embodiments where the antibody-payload conjugate comprises two linkers, it is preferred that the linkers are conjugated to residue Q295 of the two heavy chains of an IgG antibody. Even more preferably, the antibody is an IgG antibody that is glycosylated at residue N297.

In certain embodiments, the antibody-payload conjugate according to the invention comprises four linkers, wherein each linker comprises one payload, for example a toxin. In other embodiments, the antibody-payload conjugate according to the invention comprises four linkers, wherein each linker comprises two payloads, for example one toxin and one other payload or two identical or different toxins. In embodiments where the antibody-payload conjugate comprises four linkers, it is preferred that the linkers are conjugated to residues Q295 and N297Q of the two heavy chains of an IgG antibody.

In a particular embodiment, the invention relates to the antibody-payload conjugate according to the invention, wherein the antibody-payload conjugate comprises two different toxins.

In certain embodiments, the antibody-payload conjugate according to the invention comprises two different toxins. That is, in certain embodiments, the antibody-payload conjugate may comprise two linkers, wherein each linker comprises two different toxins. Antibody-payload conjugates comprising two different toxins have the advantage that they may have increased cytotoxic activity. Such increased cytotoxic activity may be achieved by combining two toxins that target two different cellular mechanisms. For example, the antibody-payload conjugates according to the invention may comprise a first toxin that inhibits cell division and a second toxin is a toxin that interferes with replication and/or transcription of DNA.

Accordingly, in a particular embodiment, the invention relates to the antibody-payload conjugate according to the invention, wherein a first toxin is a toxin that inhibits cell division and a second toxin is a toxin that interferes with replication and/or transcription of DNA.

A toxin that inhibits cell division, such as an anti-mitotic agent or a spindle poison, is an agent that has the potential to inhibit or prevent mitotic division of a cell. A spindle poison is a poison that disrupts cell division by affecting the protein threads that connect the centromere regions of chromosomes, known as spindles. Spindle poisons effectively cease the production of new cells by interrupting the mitosis phase of cell division at the spindle assembly checkpoint (SAC). The mitotic spindle is composed of microtubules (polymerized tubulin) that aid, along with regulatory proteins; each other in the activity of appropriately segregating replicated chromosomes. Certain compounds affecting the mitotic spindle have proven highly effective against solid tumors and hematological malignancies.

Two specific families of antimitotic agents—vinca alkaloids and taxanes—interrupt the cell's division by the agitation of microtubule dynamics. The vinca alkaloids work by causing the inhibition of the polymerization of tubulin into microtubules, resulting in the G2/M arrest within the cell cycle and eventually cell death. In contrast, the taxanes arrest the mitotic cell cycle by stabilizing microtubules against depolymerization. Even though numerous other spindle proteins exist that could be the target of novel chemotherapeutics, tubulin-binding agents are the only types in clinical use. Agents that affect the motor protein kinesin are beginning to enter clinical trials. Another type, paclitaxel, acts by attaching to tubulin within existing microtubules. Preferred toxins that inhibit cell division within the present invention are auristatins, such as MMAE and MMAF, and maytansinoids, such as DM1, DM3, DM4 and/or DM21.

In a particular embodiment, the invention relates to the antibody-payload conjugate according to the invention, wherein at least one of the toxins is an auristatin or a maytansinoid.

Several agents that prevent the correct replication and/or transcription of DNA molecules and have been shown to be suitable in cancer treatment are known to the person skilled in the art. For example, antimetabolites such as nucleotide or nucleoside analogs which are misincorporated into newly formed DNA and/or RNA molecules are known in the art and have been summarized by Tsesmetzis et al, Cancers (Basel), 2018, 10(7): 240. Other toxins that are known to interfere with the replication and/or transcription of DNA are duoromycins.

Accordingly, in certain embodiments, the antibody-payload conjugate according to the invention comprises two different toxins, wherein the first toxin is a duoromycin and wherein the second payload is an auristatin or a maytansinoid.

In certain embodiments, the invention relates to the antibody-payload conjugate according to the invention, wherein the antibody-payload conjugate comprises two different auristatins.

One main advantage of antibody-payload conjugates comprising two different toxins is that the antibody-payload conjugates may still act against target cells that have escaped the mechanism of action of one of the toxins and/or that the antibody-payload conjugate may have a higher efficacy against heterogenous tumors.

In a particular embodiment, the invention relates to the antibody-payload conjugate according to the invention, wherein the antibody-payload conjugate comprises a toxin and an inhibitor of a drug efflux transporter.

In a particular embodiment, the invention relates to the antibody-payload conjugate according to the invention, wherein the antibody-payload conjugate comprises a toxin and a solubility increasing moiety.

That is, the antibody-payload conjugate may comprise two payloads, wherein the first payload is a toxin and the second payload is a solubility increasing moiety. Structure 5 in FIG. 9 shows a peptide linker comprising a solubility increasing moiety coupled to a lysine side chain. Accordingly, an antibody-payload conjugate comprising a toxin and a solubility increasing moiety may be obtained by clicking a toxin to the azide group of the linker shown in Structure 5 in FIG. 9. Alternatively, an antibody-linker conjugate may be obtained by clicking a toxin to an azide-comprising linking moiety of a linker and by clicking a maleimide-comprising solubility increasing moiety to a cysteine side chain of the same linker. Alternatively, the toxin and/or the solubility increasing moiety may be attached to the linker by chemical synthesis.

In a particular embodiment, the invention relates to the antibody-payload conjugate according to the invention, wherein the antibody-payload conjugate comprises a toxin and an immunostimulatory agent.

As used herein and depending on context, the term "immunostimulatory agent" includes compounds that increase a subject's immune response to an antigen. Examples of immunostimulatory agents include immune stimulants and immune cell activating compounds. Antibody-payload conjugates of the present invention may contain immunostimulatory agents that help program the immune cells to recognize ligands and enhance antigen presentation. Immune cell activating compounds include Toll-like receptor (TLR) agonists. Such agonists include pathogen associated molecular patterns (PAMPs), e.g., an infection-mimicking composition such as a bacterially-derived immunomodulator (a.k.a., danger signal) and damage associated molecular pattern (DAMPs), e.g. a composition mimicking a stressed or damaged cell. TLR agonists include nucleic acid or lipid compositions (e.g., monophosphoryl lipid A (MPLA)). In one example, the TLR agonist comprises a TLR9 agonist such as a cytosine-guanosine oligonucleotide (CpG-ODN), a poly(ethylenimine) (PEI)-condensed oligonucleotide (ODN) such as PEI-CpG-ODN, or double stranded deoxyribonucleic acid (DNA). In another example, the TLR agonist comprises a TLR3 agonist such as polyinosine-polycytidylic acid (poly (I:C)), PEI-poly (I:C), polyadenylic-polyuridylic acid (poly (A:U)), PEI-poly (A:U), or double stranded ribonucleic acid (RNA). Other exemplary vaccine immunostimulatory compounds include lipopolysaccharide (LPS), chemokines/cytokines, fungal beta-glucans (such as lentinan), imiquimod, CRX-527, and OM-174.

In a particular embodiment, the invention relates to the antibody-payload conjugate according to the invention, wherein the antibody-payload conjugate comprises two different immunostimulatory agents.

In a particular embodiment, the invention relates to the antibody-payload conjugate according to the invention, wherein the at least one immunostimulatory agent is a TLR agonist.

The term "TLR agonist", as used herein, refers to a molecule which is capable of causing a signaling response through a TLR signaling pathway, either as a direct ligand or indirectly through generation of endogenous or exogenous. Agonistic ligands of TLR receptors are (i) natural ligands of the actual TLR receptor, or functionally equivalent variants thereof which conserve the capacity to bind to the TLR receptor and induce co-stimulation signals thereon, or (ii) an agonist antibody against the TLR receptor, or a functionally equivalent variant thereof capable of specifically binding to the TLR receptor and, more particularly, to the extracellular domain of said receptor, and inducing some of the immune signals controlled by this receptor and associated proteins. The binding specificity can be for the human TLR receptor or for a TLR receptor homologous to the human one of a different species.

In a particular embodiment, the invention relates to the antibody-payload conjugate according to the invention, wherein the antibody-payload conjugate comprises a radionuclide and a fluorescent dye.

In a particular embodiment, the invention relates to the antibody-payload conjugate according to the invention, wherein the radionuclide is a radionuclide that is suitable for use in tomography, in particular single-photon emission computed tomography (SPECT) or positron emission tomography (PET), and wherein the fluorescent dye is a near-infrared fluorescent dye.

The term "radionuclide" as used herein has the same meaning as radioactive nuclide, radioisotope or radioactive isotope.

The radionuclide is preferably detectable by nuclear medicine molecular imaging technique(s), such as, Positron Emission Tomography (PET), Single Photon Emission Computed Tomography (SPECT), an hybrid of SPECT and/or PET or their combinations. Single Photon Emission Computed Tomography (SPECT) herein includes planar scintigraphy (PS).

An hybrid of SPECT and/or PET is for example SPECT/CT, PET/CT, PET/IRM or SPECT/IRM.

SPECT and PET acquire information on the concentration (or uptake) of radionuclides introduced into a subject's body. PET generates images by detecting pairs of gamma rays emitted indirectly by a positron-emitting radionuclide. A PET analysis results in a series of thin slice images of the body over the region of interest (e.g., brain, breast, liver, . . . ). These thin slice images can be assembled into a three dimensional representation of the examined area. SPECT is similar to PET, but the radioactive substances used in SPECT have longer decay times than those used in PET and emit single instead of double gamma rays. Although SPECT images exhibit less sensitivity and are less detailed than PET images, the SPECT technique is much less expensive than PET and offers the advantage of not requiring the proximity of a particle accelerator. Actual clinical PET presents higher sensitivity and better spatial resolution than SPECT, and presents the advantage of an accurate attenuation correction due to the high energy of photons; so PET provides more accurate quantitative data than SPECT. Planar scintigraphy (PS) is similar to SPECT in that it uses the same radionuclides. However, PS only generates 2D-information.

SPECT produces computer-generated images of local radiotracer uptake, while CT produces 3-D anatomic images of X ray density of the human body. Combined SPECT/CT imaging provides sequentially functional information from SPECT and the anatomic information from CT, obtained during a single examination. CT data are also used for rapid and optimal attenuation correction of the single photon emission data. By precisely localizing areas of abnormal and/or physiological tracer uptake, SPECT/CT improves sensitivity and specificity, but can also aid in achieving accurate dosimetric estimates as well as in guiding interventional procedures or in better defining the target volume for external beam radiation therapy. Gamma camera imaging with single photon emitting radiotracers represents the majority of procedures.

The radionuclide may be selected in the group consisting of technetium-99m ($^{99m}$Tc), gallium-67 ($^{67}$Ga), gallium-68 ($^{68}$Ga) yttrium-90 ($^{90}$Y), indium-111 ($^{111}$In), rhenium-186 ($^{186}$Re), fluorine-18 ($^{18}$F), copper-64 ($^{64}$Cu), terbium-149 ($^{149}$Tb) or thallium-201 ($^{201}$TI). The radionuclide may be comprised in a molecule or bound to a chelating agent.

According to another aspect of the invention, a pharmaceutical composition is provided, the composition comprising the linker according to the above description, the linker-payload construct according to the above description, and/or the antibody-payload conjugate according to the above description.

According to another aspect of the invention, a pharmaceutical product is provided, the product comprising the antibody-payload conjugate according to the above description, or the pharmaceutical composition according to the above description, and at least one further pharmaceutically acceptable carrier.

A pharmaceutically acceptable carrier refers to an ingredient in a pharmaceutical formulation, other than an active ingredient, which is nontoxic to a subject. A pharmaceutically acceptable carrier includes, but is not limited to, a buffer, excipient, stabilizer, or preservative.

Pharmaceutical formulations of the antibody-payload conjugates described herein are prepared by mixing such conjugates having the desired degree of purity with one or more optional pharmaceutically acceptable carriers (Flemington's Pharmaceutical Sciences 16th edition, Oslo, A. Ed, (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes Zn protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

In one embodiment, the invention relates to the antibody-payload conjugate according to the invention, the pharmaceutical composition according to the invention or the pharmaceutical product according to the invention for use in therapy and/or diagnostics.

That is, the antibody-payload conjugates of the invention may be used in the treatment of a subject or in diagnosing a disease or condition in a subject. An individual or subject is a mammal. Mammals include, but are not limited to, domesticated animals (cows, sheep, cats, dogs, and horses), primates (e.g., humans and non human primates such as macaques), rabbits, and rodents (e.g., mice and rats). In certain embodiments, the individual or subject is a human.

According to another aspect of the invention, the pharmaceutical composition according to the above description or the product according to the above description is provided (for the manufacture of a medicament) for the treatment of a patient suffering from, being at risk of developing, and/or being diagnosed for a neoplastic disease, neurological disease, an autoimmune disease, an inflammatory disease or an infectious disease, or the prevention or for the prevention of such condition.

Preferably, the invention relates to the antibody-payload conjugate according to the invention, the pharmaceutical composition according to the invention or the pharmaceutical product according to the invention for use in treatment of a patient suffering from a neoplastic disease.

The term "neoplastic disease" as used herein refers to a condition characterized by uncontrolled, abnormal growth of cells. Neoplastic diseases include cancer. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, ovarian cancer, cervical cancer, gastrointestinal cancer, pancreatic cancer, glioblastoma, liver cancer, bladder cancer, hepatoma, colorectal cancer, uterine cervical cancer, endometrial carcinoma, salivary gland carcinoma, kidney cancer, vulval cancer, thyroid cancer, hepatic carcinoma, skin cancer, melanoma, brain cancer, ovarian cancer, neuroblastoma, myeloma, various types of head and neck cancer, acute lymphoblastic leukemia, acute myeloid leukemia, Ewing sarcoma and peripheral neuroepithelioma. Preferred cancers include liver cancer, lymphoma, acute lymphoblastic leukemia, acute myeloid leukemia, Ewing sarcoma and peripheral neuroepithelioma.

That is, the antibody-payload conjugates of the invention are preferably used for the treatment of cancer. As such, in certain embodiments, the antibody-payload conjugates comprise an antibody that specifically binds to an antigen that is present on a tumor cell. In certain embodiments, the antigen is an antigen on the surface of a tumor cell. In certain embodiments, the antigen on the surface of the tumor cell is internalized into the cell together with the antibody-payload conjugate upon binding of the antibody-payload conjugate to the antigen.

If the antibody-payload conjugate is used in the treatment of cancer, it is preferred that the antibody-payload conjugate comprises at least one payload that has the potential to kill or inhibit the proliferation of the tumor cell to which the antibody-drug conjugate binds to. In certain embodiments, the at least one payload exhibits its cytotoxic activity after the antibody-payload conjugate has been internalized into the tumor cell. In certain embodiments, the at least one payload is a toxin.

According to another aspect of the invention, a method of treating or preventing a neoplastic disease is provided, said method comprising administering to a patient in need thereof the antibody-payload conjugate according to the above description, the pharmaceutical composition according to the above description, or the product according to the above description.

The inflammatory disease can be an autoimmune disease. The infectious disease can be a bacterial infection or a viral infection.

In a particular embodiment, the invention relates to the antibody-payload conjugate according to the invention, the pharmaceutical composition according to the invention or the pharmaceutical product according to the invention for use in pre, intra- and/or postoperative imaging.

That is, the antibody-payload conjugate according to the invention may be used in imaging. For that, the antibody-payload conjugate may be visualized while binding to a specific target molecule, cell or tissue. Different techniques are known in the art to visualize particular payloads. For example, if the payload is a radionuclide, the molecules, cells, or tissues to which the antibody-payload conjugate binds may be visualized by PET or SPECT. If the payload is a fluorescent dye, the molecules, cells, or tissues to which the antibody-payload conjugate binds may be visualized by fluorescence imaging. In certain embodiments, the antibody-payload conjugate according to the invention comprises two different payloads, for example a radionuclide and a fluorescent dye. In this case, the molecule, cell or tissue to which the antibody-payload conjugate binds may be visualized using two different and/or complementary imaging techniques, for example PET/SPECT and fluorescence imaging.

The antibody-payload conjugate may be used for pre- intra- and/or post-operative imaging.

Pre-operative imaging encompasses all imaging techniques that may be performed before a surgery to make specific target molecules, cells or tissues visible when diagnosing a certain disease or condition and, optionally, to provide guidance for a surgery. Preoperative imaging may comprise a step of making a tumor visible by PET or SPECT before a surgery is performed by using an antibody-payload conjugate that comprises an antibody that specifically binds to an antigen on the tumor and is conjugated to a payload that comprises a radionuclide.

Intra-operative imaging encompasses all imaging techniques that may be performed during a surgery to make specific target molecules, cells or tissues visible and thus provide guidance for the surgery. In certain embodiments, an antibody-payload conjugate comprising a near-infrared fluorescent dye may be used to visualize a tumor during surgery by near-infrared fluorescent imaging. Intraoperative imaging allows the surgeon to identify specific tissues, for example tumor tissue, during surgery and thus may allow complete removal of tumor tissue.

Post-operative imaging encompasses all imaging techniques that may be performed after a surgery to make specific target molecules, cells or tissues visible and to evaluate the result of the surgery. Post-operative imaging may be performed similarly as pre-operative surgery.

In certain embodiments, the invention relates to antibody-payload conjugates comprising two or more different payloads. For example, the antibody-payload conjugate may comprise a radionuclide and a near-infrared fluorescent dye. Such an antibody-payload conjugate may be used for imaging by PET/SPECT and near-infrared fluorescent imaging. The advantage of such an antibody is that it may be used to visualize the target tissue, for example a tumor before and after a surgery by PET or SPECT. At the same time, the tumor may be visualized during the surgery by near-fluorescent infrared imaging.

In a particular embodiment, the invention relates to the antibody-payload conjugate according to the invention, the pharmaceutical composition according to the invention or the pharmaceutical product according to the invention for use in intraoperative imaging-guided cancer surgery.

As mentioned above, the antibody-payload conjugate of the invention may be used to visualize a target molecule, cell or tissue and to guide a surgeon or robot during a surgery. That is, the antibody-payload conjugate may be used to visualize tumor tissue during a surgery, for example by near-infrared imaging and to allow complete removal of the tumor tissue.

Said conjugate or product is administered to the human or animal subject in an amount or dosage that efficiently treats the disease. Alternatively, a corresponding method of treatment is provided.

An antibody-payload conjugate of the invention can be administered by any suitable means, including parenteral, intrapulmonary, and intranasal, and, if desired for local treatment, intralesional, intrauterine or intravesical administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibody-payload conjugates of the invention would be formulated, dosed, and administered in a fashion consistent of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody-payload conjugate need not be, but is optionally formulated with one or more agents currently used to prevent or treat the disorder in question. The effective amount of such other agents depends on the amount of antibody-payload conjugate present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody-payload conjugate of the invention (when used alone or in combination with one or more other additional therapeutic agents) will depend on the type of disease to be treated, the type of antibody-payload conjugate, the severity and course of the disease, whether the antibody-payload conjugate is administered for preventive or therapeutic purposes, previous therapy, the patient's clinical history and response to the antibody-payload conjugate, and the discretion of the attending physician. The antibody-payload conjugate is suitably administered to the patient at one time or over a series of treatments.

The following table 5 shows different linkers that can be used in the context of the present invention, and their SEQ ID Numbers. For the avoidance of doubt, if there is a discrepancy with the electronic WIPO ST 25 sequence listing, the sequences of this table are to be deemed the correct ones.

It is important to understand that in some linker peptides shown herein, the moiety at the C-terminus is simply designated as $N_3$. However, this should be understood as an abbreviation of Lys($N_3$). For example, GARK($N_3$) or GlyAlaArgLys($N_3$) does actually mean GARK$_1$ (with $K_1$=Lys($N_3$).

It is furthermore important to understand that in different linker peptides shown herein, the C-terminus may or may not be protected, even if shown otherwise.

Protection can be accomplished by amidation of the former. In the context of the present invention, both the protected and unprotected linker peptides are encompassed.

For example GARK($N_3$) does indeed encompass two variants, with the C-terminus protected or unprotected. On the other hand, GARK($N_3$)—COOH for example explicitly specifies a peptide which is not protected, i.e., has an unprotected C terminus.

The following table 5 shows some linkers that are encompassed, and suitable to be used, in the context of the present invention:

TABLE 5

| Three letter code | One letter code | Linking moiety B | peptide length | number of positive amino acids (Lys/Arg/His) |
|---|---|---|---|---|
| GlyAlaArgLys($N_3$) | GARK$_1$ with $K_1$ = Lys($N_3$) | Lys($N_3$) | 4 | 1 |
| GlyAlaArgLys($N_3$)Lys(Tetrazine) | GARK$_1$K$_2$ with $K_1$ = Lys($N_3$) and $K_2$ = Lys(tetrazine) | Lys($N_3$) and Lys(tetrazine) | 5 | 1 |
| GlyAlaArgLys($N_3$)Cys | GARK$_1$C with $K_1$ = Lys($N_3$) | Lys($N_3$), Cys-SH | 5 | 1 |
| GlyGlyAlaArgLys($N_3$) Lys($N_3$) | GGARK$_1$K$_2$ with $K_{1,\,2}$ = Lys($N_3$) | Lys($N_3$) | 6 | 1 |
| GlyGlyAlaArgLys($N_3$)ArgLys($N_3$) | GGARK$_1$RK$_2$ with $K_{1,\,2}$ = Lys($N_3$) | Lys($N_3$) | 7 | 2 |
| GlyAlaArgXaa($N_3$) | GARX with X = Xaa(N3), Xaa is 4-Azido-Lhomoalanine | Xaa($N_3$) | 4 | 1 |
| GlyAlaArg[PEG]3(N3) | GAR [PEG]3N3, with [PEG]3 = triethylenglycol | N3 | 3 | 1 |
| GlyAlaArgCys | GARC | Cys-SH | 4 | 1 |
| GlyGlyAlaArgLys(PEG)$_n$ArgLys($N_3$) | GGARK(PEG)$_n$RK$_1$ with $K_1$ = Lys($N_3$) | Lys($N_3$) | 7 | 2 |

TABLE 5-continued

| Three letter code | One letter code | Linking moiety B | peptide length | number of positive amino acids (Lys/Arg/His) |
|---|---|---|---|---|
| GlyβAlaArgLys($N_3$) | GβARK$_1$ with K$_1$ = Lys($N_3$) | Lys($N_3$) | 4 | 1 |
| GlyAlahomoArgLys($N_3$) | GAhRK$_1$ with K$_1$ = Lys($N_3$) | Lys($N_3$) | 4 | 1 |
| GlyβAlahomoArgLys($N_3$) | GβAhRK$_1$ with K$_1$ = Lys($N_3$) | Lys($N_3$) | 4 | 1 |
| GlyGlyAlaArgArg-B | GGARR-B | N/A | 5 | 2 |
| GlyArgAlaLys($N_3$) | GRAK$_1$ with K$_1$ = Lys($N_3$) | Lys($N_3$) | 4 | 1 |
| GlyArgAlaCys | GRAC | Cys-SH | 4 | 1 |
| GlyGlyArgLys($N_3$) | GGRK$_1$ with K$_1$ = Lys($N_3$) | Lys($N_3$) | 4 | 1 |
| GlyArgLys($N_3$) | GRK$_1$ with K$_1$ = Lys($N_3$) | Lys($N_3$) | 3 | 1 |
| GlyGlyArgLys($N_3$)Arg | GGRK$_1$R with K$_1$ = Lys($N_3$) | Lys($N_3$) | 4 | 1 |
| GlyGlyLys($N_3$)ArgCys | GGK$_1$RC with K$_1$ = Lys($N_3$) | Lys($N_3$), Cys-SH | 5 | 1 |
| GlyGlyArgArgLys($N_3$) | GGRRK$_1$ with K$_1$ = Lys($N_3$) | Lys($N_3$) | 5 | 2 |
| GlyGlyArgLys($N_3$)Arg | GGRK$_1$R with K$_1$ = Lys($N_3$) | Lys($N_3$) | 5 | 2 |
| GlyAlaHisLys($N_3$) | GAHK$_1$ with K1 = Lys($N_3$) | Lys($N_3$) | 4 | 1 |
| GlyGlyHisLys($N_3$) | GGHK$_1$ with K$_1$ = Lys($N_3$) | Lys($N_3$) | 4 | 1 |
| GlyCys | GC | Cys-SH | 2 | 0 |
| GlyGlyArgCys | GGRC | Cys-SH | 4 | 1 |
| GlyArgCys | GRC | Cys-SH | 3 | 1 |
| GlyGlyArgLys($N_3$) | GGRK$_1$ with K$_1$ = Lys($N_3$) | Lys($N_3$) | 4 | 1 |
| GlyGlyAlaLysLys($N_3$) | GGAKK$_1$ with K$_1$ = Lys($N_3$) | Lys($N_3$) | 5 | 1 |

EXAMPLES

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

All amino acid sequences disclosed herein are shown from N-terminus to C-terminus; all nucleic acid sequences disclosed herein are shown 5'->3'.

Example 1: Conjugation Efficiency

Peptides were used as obtained and dissolved at a suitable stock concentration (e.g. 25 mM) following the manufacturers instruction, aliquots were prepared and stored at −20° C. Two antibodies of IgG-subclass (antibody 1: anti Her2 IgG1, antibody 2: anti CD38 IgG1) were modified as follows: 1 mg/mL of non-deglycosylated antibody (~6.67 μM) was mixed with 80 molar equivalents of peptide linker (i.e. ~533 μM), 6 U/mL MTG and buffer. The reaction mixture was incubated for 20 h at 37° C. and then subjected for LC-MS analysis under reducing conditions.

The following table 6 shows the conjugation efficiency of a linker according to the present invention (marked with a (*) vs other linkers:

TABLE 6

| Linker (one letter code) | pH 6 | pH 7.6 | pH 8.5 |
|---|---|---|---|
| GARK(N3)* | 0 | 77.3 | 34.2 |
| AARK(N3) | 0 | 10.7 | 8.1 |
| SARK(N3) | 0 | 5.2 | 3.6 |
| AGRK(N3) | 3.6 | 22.3 | 14.7 |

It is clearly visible that the peptide comprising a N-terminal Gly residue, with no further primary amine except the N-terminal primary amine, has by far the best conjugation efficiency with the Q295 residue in the glycosylated antibody, even though the other peptides likewise comprise N-terminal primary amines, yet not comprised in a Gly residue

Example 2: Conjugation Efficiency

Peptides were used as obtained and dissolved at a suitable stock concentration (e.g. 25 mM) following the manufacturers instruction, aliquots were prepared and stored at −20° C. Two antibodies of IgG-subclass (antibody 1: anti Her2 IgG1, antibody 2: anti CD38 IgG1) were modified as follows: 1 mg/mL of non-deglycosylated antibody (~6.67 μM) was mixed with 80 molar equivalents of peptide linker (i.e. ~533 μM), 6 U/mL MTG and buffer. The reaction mixture was incubated for 20 h at 37° C. and then subjected for LC-MS analysis under reducing conditions.

The following table 7 shows the conjugation efficiency of a linker according to the present invention (marked with a (*) vs another linker βAGARK(N3) is shown in FIG. 19 (note that βA designates β-Alanine).

TABLE 7

| Linker (One letter code) | Buffer 1 (pH 6) | Buffer 2 (pH 7.6) | Buffer 3 (pH 8.5) | Buffer 4 (pH 7.6) | Buffer 5 (pH 7.6) |
|---|---|---|---|---|---|
| βAGARK(N3) | 10 | 57 | 0 | 67 | 63 |
| GGARK(N3)* | 50 | 84 | 0 | 86 | 85 |

It is clearly visible that the peptide comprising a N-terminal Gly residue, with no further primary amine except the N-terminal primary amine, has by far the better conjugation efficiency with the Q295 residue in the glycosylated antibody, compared to the structurally similar linker which has an N-terminal β-Ala residue.

Example 3: Cell Toxicity Assay

Cell lines and culture: MDA-MB-231, and SK-BR-3 were obtained from the American Type Culture Collection (ATCC) and cultured in RPMI-1640 following standard cell-culture protocols.

SK-BR-3 is a breast cancer cell line isolated by the Memorial Sloan-Kettering Cancer Center in 1970 that is used in therapeutic research, especially in context of HER2 targeting. MDA-MB-231 cells are derived from human breast adenocarcinoma of the "basal" type, and are triple negative (ER, PR and HER2 negative). Adcetris (Brentuximab Vedotin) is a commercially available antibody drug conjugate that targets CD30 and is hence expected to not be active against cells which do not express CD30, e.g., MDA-MB-231, and SK-BR-3. Kadcyla (Trastuzumab emtansine) is a commercially available antibody drug conjugate that targets Her2 and is hence expected to be active against cells which express Her2 (e.g., SK-BR-3), and not active against cells which do not express Her2 (e.g., MDA-MB-231). p684 and p579 are antibody drug conjugates produced with the linker technology as specified herein, with linkers having an N-terminal glycine (GARK($N_3$) (P684) and GGARK($N_3$) (P579)). To generate the antibody-payload conjugate, a May (Maytansine) molecule coupled to a DBCO group (see below) has been clicked to the azide groups of the linkers. Both conjugates use a non-deglycosylated antibody, and target Her2, having a Drug to Antibody Ratio of 2, hence bearing two May (Maytansine) molecules. Herceptin is a non-deglycosylated, unconjugated antibody, targeting Her2.

Cell viability was assessed by Cell Titer-Glo® (Promega) following manufacturer's instructions and as briefly outlined here. Plates were equilibrated to room temperature for 30 minutes. Cell Titer-Glo® reagent was made by addition of Cell Titer-Glo buffer to substrate. 50 μL per well of Cell Titer-Glo® reagent was added and incubated at room temperature with shaking for two minutes followed by an additional 30 minutes incubation at room temperature. Luminescence was detected on a Perkin Elmer 2030 Multilabel Reader Victor™ X3 plate reader using an integration time of 1 second.

The data were processed as follows: luminescence values of wells treated with media only were averaged and served as the reference for 100% viability. Percent viability of mAb/ADC treated wells was calculated using the following equation:

$$\%\ \text{viability} = \left(\frac{\text{Luminescenee of treated well}}{\text{Average luminescence of media treated wells}}\right) * 100\%$$

Normalized percent viability was plotted versus the logarithm of mAb/ADC concentration and the data were fit using GraphPad Prism 7.00.

As can be seen in FIG. 18, P684 and P579 have the same potency against SK-BR3 cells as Kadcyla. Hence, the advantages provided by the novel linker technology (ease of manufacture, site specificity, stable stoichiometry, no need to deglycosylate that antibody) do not come at any disadvantage regarding the cellular toxicity. This is even more important as P684 and P579 have a DAR of 2, while Kadcyla has an average DAR of 3.53±0.05, hence is capable to deliver more toxin to the target cells. The following table show the potencies (IC50):

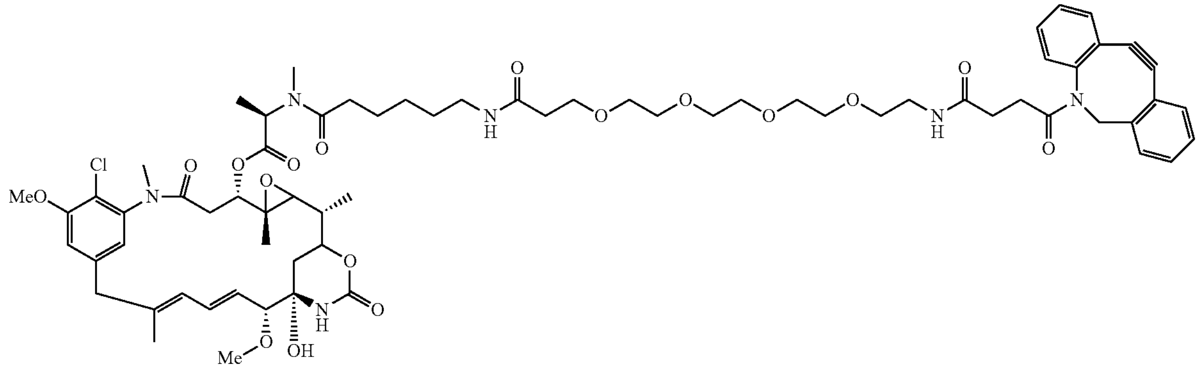 [SMILES: COc1cc2cc(c1Cl)N(C)C(=O)C[C@H](OC(=O)[C@@H](C)N(C)C(=O)CCCCCNC(=O)CCOCCOCCOCCOCCNC(=O)CCC(=O)N1Cc3ccccc3C#Cc3ccccc31)[C@]1(C)OC1[C@H](C)C1C[C@@](O)(NC(=O)O1)[C@H](OC)/C=C/C=C(\C)C2]

Cell toxicity assay: Cells were seeded into 96 well plates (white walled, clear flat bottom plates) at densities of 10,000 cells per well and incubated overnight at 37° C. and 5% $CO_2$. Monoclonal antibodies (mAbs) and antibody-drug conjugates (ADCs) were serially diluted 1:4 in media at a starting concentration of 10 μg/mL (66.7 nM). Media was removed from cells, and mAb/ADC dilutions were added. Cells treated with media only served as the reference for 100% viability. Cells were incubated with antibodies for three days at 37° C. and 5% $CO_2$.

| | |
|---|---|
| Her-P684-May | 1.4 nM |
| Her-P579-May | 0.50 nM |
| Kadcyla | 0.33 nM |

Example 4: Conjugation Efficiency

Peptides were used as obtained and dissolved at a suitable stock concentration (e.g. 25 mM) following the manufacturers instruction, aliquots were prepared and stored at −20°

C. The anti-Her2 IgG1 antibody (Trastuzumab) was modified as follows: 1 mg/mL of non-deglycosylated antibody (~6.67 μM) was mixed with 80 molar equivalents of peptide linker (i.e. ~533 μM), 6 U/mL MTG and buffer. The reaction mixture was incubated for 20 h at 37° C. and then subjected for LC-MS analysis under reducing conditions.

The following table 8 shows the conjugation efficiencies (CE in %) of various linkers falling within the scope of the present invention.

| Sequence | Charge | C-Terminal | Formula | MW | CE in % |
|---|---|---|---|---|---|
| GDC | negative | amidation | $C_9H_{16}N_4O_5S_1$ | 292.31 | 9.7 |
| GRCD | neutral | amidation | $C_{15}H_{28}N_8O_6S_1$ | 448.49 | 11.2 |
| GRDC | neutral | amidation | $C_{15}H_{28}N_8O_6S_1$ | 448.49 | 4.4 |
| GGDC | negative | amidation | $C_{11}H_{19}N_5O_6S_1$ | 349.36 | 25.1 |
| GGCD | negative | amidation | $C_{11}H_{19}N_5O_6S_1$ | 349.36 | 49.1 |
| GGEC | negative | amidation | $C_{12}H_{21}N_5O_6S_1$ | 363.39 | 23.7 |
| GGK($N_3$)D | negative | amidation | $C_{14}H_{24}N_8O_6$ | 400.4 | 68.4 |
| GGRCD | neutral | amidation | $C_{17}H_{31}N_9O_7S_1$ | 505.54 | 78.8 |
| GGGDC | negative | amidation | $C_{13}H_{22}N_6O_7S_1$ | 406.41 | 35.6 |
| GC | neutral | amidation | $C_5H_{10}N_2O_3S_1$ | 178.21 | 92 |
| GRC | positive | amidation | $C_{11}H_{23}N_7O_3S_1$ | 333.41 | 51.7 |
| GGRC | positive | amidation | $C_{13}H_{26}N_8O_4S_1$ | 390.46 | 91.4 |
| GRAC | positive | amidation | $C_{14}H_{28}N_8O_4S_1$ | 404.49 | 47.7 |
| GARC | positive | amidation | $C_{14}H_{28}N_8O_4S_1$ | 404.49 | 88.5 |
| GGHK($N_3$) | positive | amidation | $C_{16}H_{26}N_{10}O_4$ | 422.45 | 16.1 |
| GGK($N_3$)RC | positive | amidation | $C_{19}H_{36}N_{12}O_5S_1$ | 544.63 | 79.5 |
| GARK($N_3$) | positive | amidation | $C_{19}H_{37}N_9O_4$ | 455.56 | 77.3 |
| AARK($N_3$) | positive | amidation | $C_{20}H_{39}N_9O_4$ | 469.59 | 10.7 |
| SARK($N_3$) | positive | amidation | $C_{20}H_{39}N_9O_5$ | 485.59 | 5.2 |
| AGRK($N_3$) | positive | amidation | $C_{19}H_{37}N_9O_4$ | 455.56 | 22.3 |
| βAGARK($N_3$) | positive | amidation | $C_{20}H_{38}N_{12}O_5$ | 526.6 | 57 |
| GGARK($N_3$) | positive | amidation | $C_{19}H_{36}N_{12}O_5$ | 512.58 | 84 |

REFERENCES

Dorywalska et al (2015), Site-Dependent Degradation of a Non-Cleavable Auristatin-Based Linker-Payload in Rodent Plasma and Its Effect on ADC Efficacy. PLoS ONE 10(7): e0132282

Sletten & Bertozzi, A Bioorthogonal Quadricyclane Ligation. J Am Chem Soc 2011,133 (44), 17570-17573.

Agard et al, J Am Chem Soc. 2004 Nov. 24; 126(46): 15046-7.

Stöckmann et al (2011). "Exploring isonitrile-based click chemistry for ligation with biomolecules". Organic & Biomolecular Chemistry. 9 (21): 7303.

Blackman et al (2008). "The Tetrazine Ligation: Fast Bioconjugation based on Inverse-electron-demand Diels-Alder Reactivity". Journal of the American Chemical Society. 130 (41): 13518-9.

Yarema, et al (1998). "Metabolic Delivery of Ketone Groups to Sialic Acid Residues. Application To Cell Surface Glycoform Engineering". Journal of Biological Chemistry. 273 (47): 31168-79.

Ning et al (2010). "Protein Modification by Strain-Promoted Alkyne-Nitrone Cycloaddition". Angewandte Chemie International Edition. 49 (17): 3065.

Baskin et al (2007). "Copper-free click chemistry for dynamic in vivo imaging". Proceedings of the National Academy of Sciences. 104 (43): 16793-7.

MacKenzie, D A; Sherratt, A R; Chigrinova, M; Cheung, L L; Pezacki, J P (August 2014). "Strain-promoted cycloadditions involving nitrones and alkynes—rapid tunable reactions for bioorthogonal labeling". Curr Opin Chem Biol. 21: 81-8.

Agard, N. J.; Baskin, J. M.; Prescher, J. A.; Lo, A.; Bertozzi, C. R. (2006). "A Comparative Study of Bioorthogonal Reactions with Azides". ACS Chem. Biol. 1: 644-648

Kolb, H. C.; Sharpless, B. K. (2003). "The growing impact of click chemistry on drug discovery". Drug Discov Today. 8 (24): 1128-1137.

Lhospice et al., Site-Specific Conjugation of Monomethyl Auristatin E to Anti-Cd30 Antibodies Improves Their Pharmacokinetics and Therapeutic Index in Rodent Models, Mol Pharm 12 (6), 1863-1871. 2015

Jeger et al, Site-specific and stoichiometric modification of antibodies by bacterial transglutaminase. Angew Chem Int Ed Engl. 2010 Dec. 17; 49(51):9995-7

Strop, et al., Versatility of Microbial Transglutaminase. Bioconjugate Chemistry 2014, 25 (5), 855-862.

Spycher et al., Dual Site-Specifically Modified Antibodies With Solid-Phase Immobilized Microbial Transglutaminase. Chembiochem. 2017 Aug. 3; 18(19): 1923-1927

Dennler et al., Transglutaminase-based chemo-enzymatic conjugation approach yields homogeneous antibody-drug conjugates. Bioconjug Chem. 2014 Mar. 19; 25(3):569-78

Dennler et al. Microbial transglutaminase and c-myc-tag: a strong couple for the functionalization of antibody-like protein scaffolds from discovery platforms. Chembiochem. 2015 Mar. 23; 16(5):861-7

Mindt, et al., Modification of different IgG1 antibodies via glutamine and lysine using bacterial and human tissue transglutaminase. Bioconjugate chemistry 2008, 19 (1), 271-8.

Dubowchik et al., Cathepsin B-labile dipeptide linkers for lysosomal release of doxorubicin from internalizing immunoconjugates: model studies of enzymatic drug release and antigen-specific in vitro anticancer activity. Bioconjug Chem. 2002 July-August; 13(4):855-69.

Zheng, et al., The impact of glycosylation on monoclonal antibody conformation and stability. Mabs-Austin 2011, 3 (6), 568-576.

Subedi, et al., The Structural Role of Antibody N-Glycosylation in Receptor Interactions. Structure 2015, 23 (9), 1573-1583.

Kieliszek and Misiewicz, Folia Microbiol (Praha). 2014; 59(3): 241-250

Brinkmann and Kontermann, The making of bispecific antibodies. MAbs. 2017 February-March; 9(2): 182-212.

Azhdarinia A. et al., Dual-Labeling Strategies for Nuclear and Fluorescence Molecular Imaging: A Review and Analysis. Mol Imaging Biol. 2012 June; 14(3): 261-276.

Houghton J L. et al., Site-specifically labeled CA19.9-targeted immunoconjugates for the PET, NIRF, and multimodal PET/NIRF imaging of pancreatic cancer. Proc Natl Acad Sci USA. 2015 Dec. 29; 112(52): 15850-5

Levengood M. et al., Orthogonal Cysteine Protection Enables Homogeneous Multi-Drug Antibody—Drug Conjugates. Angewandte Chemie, Volume 56, Issue 3, Jan. 16, 2017

Costoplus J A. et al., Peptide-Cleavable Self-immolative Maytansinoid Antibody-Drug Conjugates Designed To Provide Improved Bystander Killing. ACS Med Chem Lett. 2019 Sep. 27; 10(10):1393-1399.

Sonzini S. et al., Improved Physical Stability of an Antibody-Drug Conjugate Using Host-Guest Chemistry. Bioconjug Chem. 2020 Jan. 15; 31(1):123-129.

Bodero L. et al., Synthesis and biological evaluation of RGD and isoDGR peptidomimetic-α-amanitin conjugates for tumor-targeting. Beilstein J. Org. Chem. 2018, 14, 407-415.

Nunes J P M. et al., Use of a next generation maleimide in combination with THIOMAB™ antibody technology delivers a highly stable, potent and near homogeneous THIOMAB™ antibody-drug conjugate (TDC). RSC Adv., 2017, 7, 24828-24832.

Doronina S O. et al., Enhanced activity of monomethylauristatin F through monoclonal antibody delivery: effects of linker technology on efficacy and toxicity. Bioconjug Chem. 2006 January-February; 17(1):114-24.

Nakada T. et al., Novel antibody drug conjugates containing exatecan derivative-based cytotoxic payloads. Bioorg Med Chem Lett. 2016 Mar. 15; 26(6):1542-1545.

Dickgiesser S. et al., Site-Specific Conjugation of Native Antibodies Using Engineered Microbial Transglutaminases. Bioconjug Chem. 2020 Mar. 12. doi: 10.1021/acs.bioconjchem.0c00061.

Steffen W. et al., Discovery of a microbial transglutaminase enabling highly site-specific labeling of proteins. The Journal of Biological Chemistry. Jul. 27, 2017 doi: 10.1074/jbc.M117.797811.

Malesevic M. et al., A fluorescence-based array screen for transglutaminase substrates. Chembiochem. 2015 May 26; 16(8):1169-74.

DISCLAIMER

It is important to understand that in some linker peptides shown herein, the moiety at the C-terminus is simply designated as $N_3$. However, this should be understood as an abbreviation of Lys($N_3$). For example, GAR($N_3$) does actually mean $GARK_1$, with $K_1$=Lys($N_3$), or GlyAlaArgLys ($N_3$).

It is furthermore important to understand that in different linker peptides shown herein, the C-terminus may or may not be protected, even if shown otherwise. Protection can be accomplished by amidation. In the context of the present invention, both the protected and unprotected linker peptides are encompassed. For example GARK($N_3$) does indeed encompass two variants, with the C-terminus protected or unprotected.

The invention claimed is:

1. An antibody-payload conjugate comprising a) an antibody comprising at least one Gln residue in the heavy or light chain; and b) one or more linker-payload constructs comprising the peptide structure (shown in N->C direction)

Gly-$(Aax)_m$-B-$(Aax)_n$ wherein Gly comprises an N-terminal primary amine, and wherein m is an integer between ≥0 and ≤12 n is an integer between ≥0 and ≤12 m+n≥0,

Aax is an amino acid, and wherein either (i) B is a payload; or (ii) B is a linking moiety, wherein the linker-payload construct further comprises a payload that is covalently or non-covalently bound to the linking moiety;

wherein the linker-payload construct is conjugated to the heavy or light chain of the antibody via an isopeptide bond between the amide side chain of the at least one Gln residue in the heavy or light chain of the antibody and the N-terminal primary amine of the N-terminal glycine residue comprised in the linker-payload construct.

2. The antibody-payload conjugate according to claim 1, wherein the conjugation has been achieved with a microbial transglutaminase (MTG).

3. A pharmaceutical composition comprising the antibody-payload conjugate according to claim 1.

4. A pharmaceutical product comprising the antibody-payload conjugate according to claim 1 and at least one further pharmaceutically acceptable ingredient.

5. The antibody-payload conjugate according to claim 1, wherein the Gln residue is Gln residue Q295 (EU numbering) of the CH2 domain of an IgG antibody.

6. The antibody-payload conjugate according to claim 1, wherein the linker comprises two or more payloads and/or linking moieties B.

7. The antibody-payload conjugate according to claim 1, wherein at least one of the one or more linking moieties B comprises a bioorthogonal marker group or a non-bioorthogonal entity for crosslinking.

8. The antibody-payload conjugate according to claim 7, wherein the bioorthogonal marker group or the non-bioorthogonal entity is at least one selected from a group consisting of:

—N—N≡N, or $—N_3$ $Lys(N_3)$ tetrazine alkyne

DBCO

BCN norborene transcyclooctene

—RCOH (aldehyde),
acyltrifluoroborates,
—SH, and
cysteine.

9. The antibody-payload conjugate according to claim 1, wherein the one or more payloads is selected from a group consisting of:
a toxin
a cytokine
a growth factor
a radionuclide
a hormone
an anti-viral agent
an anti-bacterial agent
a fluorescent dye
an immunoregulatory/immunostimulatory agent
a half-life increasing moiety
a solubility increasing moiety
a polymer-toxin conjugate
a nucleic acid
a biotin or streptavidin moiety
a vitamin
a target binding moiety, and
an anti-inflammatory agent.

10. The antibody-payload conjugate according to claim 1, wherein antibody-payload conjugate comprises at least one toxin.

11. The antibody-payload conjugate according to claim 10, wherein the toxin is at least one selected from the group consisting of:
pyrrolobenzodiazepines (PBD)
auristatins (e.g., MMAE, MMAF)
maytansinoids (maytansine, DM1, DM4, DM21)
duocarmycins
tubulysins
enediyenes (e.g. calicheamicin)
PNUs, doxorubicins
pyrrole-based kinesin spindle protein (KSP) inhibitors
calicheamicins
amanitins (e.g. α-amanitin), and
camptothecins (e.g. exatecans, deruxtecans).

12. The antibody-payload conjugate according to claim 10, wherein at least one of the toxins is an auristatin or a maytansinoid.

13. The antibody-payload conjugate according to claim 10, wherein the antibody-payload conjugate comprises
i) a toxin and an inhibitor of a drug efflux transporter; or
ii) a toxin and a solubility increasing moiety; or
iii) a toxin and an immunostimulatory agent; or
iv) two different toxins.

14. The antibody-payload conjugate according to claim 10, comprising two different toxins, wherein a first toxin is a toxin that inhibits cell division and a second toxin is a toxin that interferes with replication and/or transcription of DNA.

15. The antibody-payload conjugate according to claim 1, wherein the antibody-payload conjugate comprises two immunostimulatory agents.

16. The antibody-payload conjugate according to claim 15, wherein the at least one immunostimulatory agent is a TLR agonist.

17. The antibody-payload conjugate according to claim 1, wherein the antibody-payload conjugate comprises a radionuclide and a fluorescent dye.

18. The antibody-payload conjugate according to claim 17, wherein the radionuclide is a radionuclide that is suitable for use in tomography.

19. The antibody-payload conjugate according to claim 18, wherein the tomography is single-photon emission computed tomography (SPECT) or positron emission tomography (PET).

20. The antibody-payload conjugate according to claim 17 wherein the fluorescent dye is a near-infrared fluorescent dye.

21. The antibody-payload conjugate according to claim 1, wherein the linker does not comprise a cathepsin cleavable site.

22. The antibody-payload conjugate according to claim 1, wherein the linker does not comprise a valine-alanine motif or a valine-citrulline motif.

23. The antibody-payload conjugate according to claim 1, wherein m+n≤12.

24. The antibody-payload conjugate according to claim 1, wherein the net charge of the linker is neutral or positive.

25. The antibody-payload conjugate according to claim 1, wherein the linker does not comprise negatively charged amino acid residues.

26. The antibody-payload conjugate according to claim 1, wherein the linker comprises at least one positively charged amino acid residue.

27. The antibody-payload conjugate according to claim 1, wherein the linker comprises at least one amino acid residue selected from a group consisting of lysine, arginine, and histidine.

28. The antibody-payload conjugate according to claim 1, wherein the linker-payload construct is selected from following list:

| |
|---|
| Gly-Ala-Arg-Lys($N_3$) |
| Gly-Ala-Arg-Lys($N_3$)-Lys(Tetrazine) |
| Gly-Ala-Arg-Lys($N_3$)-Cys |
| Gly-Gly-Ala-Arg-Lys($N_3$)-Lys($N_3$) |
| Gly-Gly-Ala-Arg-Lys($N_3$)-Arg-Lys($N_3$) |
| Gly-Ala-Arg-Xaa($N_3$) |
| Gly-Ala-Arg-[PEG]3(N3) |
| Gly-Ala-Arg-Cys |
| Gly-Gly-Ala-Arg-Lys(PEG)$_n$-Arg-Lys($N_3$) |
| Gly-βAla-Arg-Lys($N_3$) |
| Gly-Ala-homoArg-Lys($N_3$) |
| Gly-βAla-homoArg-Lys($N_3$) |
| Gly-Gly-Ala-Arg-Arg-B |
| Gly-Arg-Ala-Lys($N_3$) |
| Gly-Arg-Ala-Cys |
| Gly-Gly-Arg-Lys($N_3$) |
| Gly-Arg-Lys($N_3$) |
| Gly-Gly-Arg-Lys($N_3$)-Arg |
| Gly-Gly-Lys($N_3$)-Arg-Cys |
| Gly-Gly-Arg-Arg-Lys($N_3$) |
| Gly-Gly-Arg-Lys($N_3$)-Arg |
| Gly-Ala-His-Lys($N_3$) |
| Gly-Gly-His-Lys($N_3$) |
| Gly-Cys |
| Gly-Gly-Arg-Cys |
| Gly-Arg-Cys |
| Gly-Gly-Arg-Lys($N_3$) |
| Gly-Gly-Ala-Lys-Lys($N_3$) |

wherein Lys($N_3$) is 6-azido-L-lysine; Xaa($N_3$) is 4-Azido-L-homoalanine; Lys(Tetrazine) is a tetrazine-modified L-lysine, and $[PEG]_3(N_3)$ is an azido-terminated triethylene glycol moiety; and
wherein when the linker-payload construct comprises an azide group ($N_3$), the payload comprises an alkyne or a cyclooctyne, and the azide is ligated to the alkyne or cyclooctyne via a 1,3-dipolar cycloaddition reaction.

29. The antibody-payload conjugate according to claim 1, wherein in said construct, the one or more payloads have been covalently bound to the linking moiety B of the linker with a click reaction.

30. The antibody-payload conjugate according to claim 1, wherein the linker-payload construct has been obtained by chemical synthesis.

31. The antibody-payload conjugate according to claim 1, wherein the one or more payloads have been chemically modified during binding to allow covalent or non-covalent binding to form said construct.

32. The antibody-payload conjugate according to claim 1, wherein the conjugation has been achieved before or after formation of the linker-payload construct.

33. The antibody-payload conjugate according to claim 1, wherein in said conjugate, the linker-payload constructs and/or the antibody have been chemically modified during conjugation to allow covalent conjugation, to form said conjugate.

34. The antibody-payload conjugate according to claim 1, wherein the antibody is an IgG or a fragment or recombinant variant thereof, wherein the fragment or recombinant variant thereof retains target binding properties and comprises a $C_H2$ domain.

35. The antibody-payload conjugate according to claim 1, wherein the antibody is a glycosylated antibody.

36. The antibody-payload conjugate according to claim 35, wherein the antibody is an IgG antibody that is glycosylated at residue N297 (EU numbering) of the $C_H2$ domain.

37. The antibody-payload conjugate according to claim 36, wherein the Gln residue is Gln residue Q295 (EU numbering) of the CH2 domain of an IgG antibody.

* * * * *